(12) United States Patent
Irlapati et al.

(10) Patent No.: US 9,399,638 B2
(45) Date of Patent: Jul. 26, 2016

(54) SUBSTITUTED PYRIDINE COMPOUNDS AS CRAC MODULATORS

(71) Applicant: LUPIN LIMITED, Mumbai, Maharashtra (IN)

(72) Inventors: Nageswara Rao Irlapati, Maharashtra (IN); Zubair Abdul Wajid Shaikh, Maharashtra (IN); Vijay Pandurang Karche, Maharashtra (IN); Gokul Keruji Deshmukh, Maharashtra (IN); Neelima Sinha, Maharashtra (IN); Venkata P. Palle, Maharashtra (IN); Rajender Kumar Kamboj, Maharashtra (IN)

(73) Assignee: LUPIN LIMITED, Mumbai, Maharashtra (IN)

( * ) Notice: Subject to any disclaimer, the term of this patent is extended or adjusted under 35 U.S.C. 154(b) by 0 days.

(21) Appl. No.: 14/398,154

(22) PCT Filed: May 1, 2013

(86) PCT No.: PCT/IB2013/053440
§ 371 (c)(1),
(2) Date: Oct. 31, 2014

(87) PCT Pub. No.: WO2013/164769
PCT Pub. Date: Nov. 7, 2013

(65) Prior Publication Data
US 2015/0111900 A1    Apr. 23, 2015

(30) Foreign Application Priority Data
May 2, 2012    (IN) .................... 6/KOL/2012

(51) Int. Cl.
*C07D 413/04* (2006.01)
*C07D 417/14* (2006.01)
*C07D 413/14* (2006.01)

(52) U.S. Cl.
CPC ............ *C07D 417/14* (2013.01); *C07D 413/04* (2013.01); *C07D 413/14* (2013.01)

(58) Field of Classification Search
CPC .................................................. C07D 413/04
USPC ....................................... 546/269.4; 514/340
See application file for complete search history.

(56) References Cited

U.S. PATENT DOCUMENTS

| 2010/0152241 | A1 | 6/2010 | Whitten |
| 2011/0212998 | A1 | 9/2011 | Bolli et al. |

FOREIGN PATENT DOCUMENTS

| WO | WO2005/009539 A2 | 2/2005 |
| WO | WO 2005/009954 A2 | 2/2005 |
| WO | WO 2006/034402 A2 | 3/2006 |
| WO | WO 2006/081389 A1 | 8/2006 |
| WO | WO 2006/081391 A2 | 8/2006 |
| WO | WO 2006/083477 A2 | 8/2006 |
| WO | WO 2007/087429 A2 | 8/2007 |
| WO | WO 2007/087441 A2 | 8/2007 |
| WO | WO 2007/087442 A2 | 8/2007 |
| WO | WO 2007/089904 A2 | 8/2007 |
| WO | WO 2008/024724 A1 | 2/2008 |
| WO | WO 2009/017819 A1 | 2/2009 |
| WO | WO 2009/035818 A1 | 3/2009 |
| WO | WO 2009/076454 A2 | 6/2009 |
| WO | WO 2009/141398 A1 | 11/2009 |
| WO | WO 2010/000475 A1 | 1/2010 |
| WO | WO 2010/025295 A2 | 3/2010 |
| WO | WO 2010/027875 A2 | 3/2010 |
| WO | WO 2010/039238 A1 | 4/2010 |
| WO | WO 2011/024004 A1 | 3/2011 |
| WO | WO 2011/034962 A2 | 3/2011 |
| WO | WO 2012/056478 A1 | 5/2012 |
| WO | WO 2012/151355 A1 | 11/2012 |
| WO | WO 2013/059666 A1 | 4/2013 |
| WO | WO 2013/059677 A1 | 4/2013 |

OTHER PUBLICATIONS

International Search Report for corresponding International Patent Application No. PCT/IB2013/053440 mailed Jun. 21, 2013.
Di Sabatino, A. et al., "Targeting Gut T Cell $Ca^{2+}$ Release-Activated $Ca^{2+}$ Channels Inhibits T Cell Cytokine Production and T-Box Transcription Factor T-Bet in Inflammatory Bowel Disease", *J. Immunol.*, 183: 3454-3462 (2009).
Parakh, A. et al., "Store-Operated Calcium Channels", *Physiol. Rev.*, 85: 757-810 (2005).
Fahrner, M. et al., "Mechanistic view on domains mediating STIM1-Orai coupling", *Immuno. Rev.*, 231: 99-112 (2009).

(Continued)

*Primary Examiner* — Patricia L Morris
(74) *Attorney, Agent, or Firm* — Merchant & Gould P.C.

(57) ABSTRACT

The present invention relates to compounds described herein Formula (I) and pharmaceutical acceptable salts thereof, which modulate the activity of calcium release-activated calcium (CRAC) channel. The invention also describes the compounds of Formula (I) and pharmaceutical compositions containing such compounds thereof for treating, managing, and/or lessening the severity of diseases, disorders, syndromes or conditions associated with the modulation of calcium release-activated calcium (CRAC) channel.

(I)

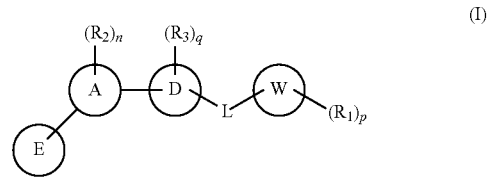

11 Claims, No Drawings

(56) References Cited

OTHER PUBLICATIONS

Parekh, A., "Store-operated CRAC channels: function in health and disease", *Nat. Rev.*, 9: 399-410 (2010).

Yang, S. et al., "Orail and STIM1 Are Critical for Breast Tumor Cell Migration and Metastasis", *Cancer Cell*, 15: 124-134 (2009).

Abeele, F. et al., "Bcl-2-dependent modulation of $Ca^{2+}$ homeostasis and store-operated channels in prostate cancer cells", *Cancer Cell*, 1: 169-179 (2002).

Motiani, R. et al., "A Novel Native Store-operated Calcium Channel Encoded by Orai3", *J. Biol. Chem.*, 285(25): 19173-19183 (2010).

Varga-Szabo, D. et al., "The calcium sensor STIM1 is an essential mediator of arterial thrombosis and ischemic brain infarction", *J. Exp. Med.*, 205(7): 1583-1591 (2008).

Braun, A. et al., "Orai 1 (CRACM1) is the platelet SOC channel and essential for pathological thrombus formation", *Blood*, 113(9): 2056-2063 (2009).

Gillo, K. et al., "Roles of Platelet STIM1 and Orail in Glycoprotein VI- and Thrombin-dependent Procoagulant Activity and Thrombus Formation", *J. Bio. Chem.*, 285 (31): 23629-23638 (2010).

Ziener, U. et al., "Recognition-Directed Supramolecular Assemblies of Metal Complexes of Terpyridine Derived Lignads with Self-Complementary Hydrogen Bonding Sites", *Chem. Euro. J.*, 6(22): 4132-4139 (2000).

Morisue, M. et al., Ligand-assisted J-type aggregates of zinc porphyrin: anticooperative molecular organization in self-assembled bolaamphiphile *Org. Biomol. Chem.*, 8: 3457-3463 (2010).

Uchiyama, M. et al., "Generation and Suppression of 3-/4-Functionalized Benzynes Using Zinc Ate Base (TMP-Zn-ate): New Approaches to Multisubstituted Benzenes", *J. Am. Chem. Soc.*, 130: 472-480 (2008).

Wuts, P. et al., Ed., "Greene's Protective Groups in Organic Synthesis", $4^{th}$ Ed., John Wiley & Sons, NY (2007).

SUBSTITUTED PYRIDINE COMPOUNDS AS CRAC MODULATORS

RELATED APPLICATIONS

The present application is a National Stage Application of PCT/IB2013/053440, filed May 1, 2013, which claims the benefit of priority to Indian Provisional Patent Application No. 0006/KOL/2012, filed on May 2, 2012 and which applications are incorporated herein by reference. To the extent appropriate, a claim of priority is made to each of the above disclosed applications.

TECHNICAL FIELD OF THE INVENTION

The invention relates to substituted pyridine compounds, pharmaceutically acceptable salts thereof and pharmaceutical compositions for the treatment, management, and/or lessening of severity of diseases, disorders, syndromes or conditions associated with the modulation of calcium release-activated calcium (CRAC) channel. The invention also relates to methods of treating, managing and/or lessening the severity of the diseases disorders, syndromes or conditions associated with the modulation of CRAC. The invention also relates to processes for the preparation of the compounds of the invention.

BACKGROUND OF THE INVENTION

Inflammation is the response by the body to infection, irritation or injury; wherein the immune cells of the body are activated in response to any of these stimuli. Inflammation plays a key role in many diseases not only of the immune cells such as allergy, asthma, arthritis, dermatitis, multiple sclerosis, systemic lupus but also organ transplant, diabetes, cardiovascular disease, Alzheimer's disease, Parkinson's disease, inflammatory and/or irritable bowel syndrome (Di Sabatino et. al., J. Immunol., 183, 3454-3462, 2009), psoriasis, and cancer. An initial inflammatory response to pathogens or injury is necessary and required to fight infection or heal the wound, but sustained or persistent inflammation can lead to any of the chronic disorders; characterized by the production of inflammatory cytokines as, specified above.

Inflammation is characterized by the production of different cytokines such as IL-2, IL-4, IL-10. IL-13, IL-17, IL-21, IL-23, IL-28, IFN-γ, TNF-α, etc., that have been implicated in playing a role in different diseases. Any drug which can modulate the production of these cytokines would help alleviate the disease symptoms and may also cure it. $Ca^{+2}$ signals have been shown to be essential for diverse cellular functions in different cell types including differentiation, effector functions, and gene transcription in cells of the immune system as well as regulating the cytokine signaling pathway through calcineurin and nuclear factor of activated T cells (NFAT).

In immune cells, sustained $Ca^{+2}$ influx has been shown to be necessary for complete and long-lasting activation of calcineurin-NFAT pathways, essential for cytokine production. Engagement of receptors such as T-cell antigen receptor (TCR), the B-cell antigen receptor (BCR), and the Fc receptors (FcR) on mast cells, macrophages, and NK cells, leads to the tyrosine phosphorylation and activation of phospholipase C-γ (PLC-γ). PLC-γ hydrolyzes phosphatidylinositol-3,4-biphosphate ($PIP_2$) to the second messengers, inositol-1,4,5-triphosphate ($IP_3$) and diacylglycerol (DAG). $IP_3$ binds to $IP_3$ receptors ($IP_3R$) in the membrane of the endoplasmic reticulum (ER) and induces the release of ER $Ca^{+2}$ stores into the cytoplasma. The decrease in the $Ca^{+2}$ concentration in the ER induces store-operated $Ca^{+2}$ entry (SOCE) through plasma membrane $Ca^{+2}$ channels. SOCE through highly $Ca^{+2}$-selective $Ca^{+2}$ release-activated $Ca^{+2}$ (hereinafter, CRAC) channels constitutes the major pathway of intracellular $Ca^{+2}$ entry in T cells, B cells, macrophages, mast cells, and other cell types (Parekh and Putney, Physiol. Rev., 85, 757-810, 2005).

The CRAC channel is comprised of two family proteins, one which functions in sensing $Ca^{+2}$ levels in the ER—the stromal interacting molecules (STIM)-1 and -2 and the other which is a pore-forming protein—Orai1, 2 and 3. The STIM proteins are single transmembrane proteins localized on the ER membrane with their N-termini oriented toward the lumen and containing an EF-hand $Ca^{+2}$ binding motif. Depletion of $Ca^{+2}$ from the ER causes $Ca^{+2}$ to dissociate from STIM, which causes a conformational change that promotes oligomerization and migration of STIM molecules to closely apposed ER-plasma membrane junctions. At the junctions, the STIM oligomers interact with the Orai proteins. In resting cells, Orai channels are dispersed across the plasma membrane and on depletion of $Ca^{+2}$ from the stores, they aggregate in the vicinity of the STIM punctae. The eventual increase in intracellular $Ca^{+2}$ concentration activates the calcineurin-NFAT pathway. NFAT activates transcription of several genes including cytokine genes such as IL-2, etc along with other transcription factors such as AP-1, NFκB and Foxp3 (Fahmer et. al., Immuno. Rev., 231, 99-112, 2009).

The role of CRAC channel in different diseases such as allergy, inflammatory bowel disease, thrombosis and breast cancer has been reported in literature (Parekh, Nat. Rev., 9, 399-410, 2010). It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

Recent literature reports the role of STIM1 and Orai1 in collagen dependent arterial thrombosis in mice in vivo and that deficiency in either protects against collagen dependent arterial thrombus formation as well as brain infarction (Varga-Szabo et. al., J. Exp. Med., 205, 1583-1591, 2008; Braun et. al., Blood, 113, 2056-2063, 2009). The role of STIM1-Orai1 mediated SOCE in thrombus formation makes Orai1 a potential target for treatment of thrombosis and related conditions (Gillo et. al., JBC, 285; 31, 23629-23638, 2010).

As the Orai pore channel proteins have been shown to be essential for transmitting the signal induced by the binding of antigens to the cellular receptors on the immune cells, a potential Orai channel interacting drug would be able to modulate the signaling thereby impacting the secretion of the cytokines involved in, as mentioned hereinbefore, inflammatory conditions, cancer, allergic disorders, immune disorders, rheumatoid arthritis, cardiovascular diseases, thrombocytopathies, arterial and/or venous thrombosis and associated or related conditions which can be benefitted by the CRAC channel modulatory properties of the compounds described herein.

Several compounds have been reported in the art as CRAC channel modulators. For example, patent application publications WO2005009539, WO2005009954, WO2006081391, WO2006081389, WO2006034402, WO2006083477, WO2007087441, WO2007087442, WO2007087429, WO2007089904, WO2009017819, WO2009076454, WO2009035818, US20100152241, WO2010039238, WO2010025295, WO2010027875, WO2011034962, WO2012151355, WO2013059666, WO2013059677 disclose the compounds for modulating CRAC channels.

SUMMARY OF THE INVENTION

In accordance with one aspect, the invention provides the compounds of Formula (I):

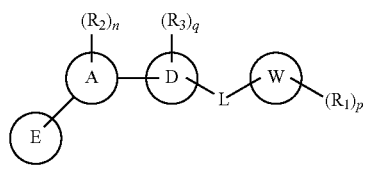

(I)

wherein, ring A is monocyclic heteroaryl provided that the ring A is not pyrazolyl;

ring E is a 5-membered non aromatic heterocyclic ring selected from

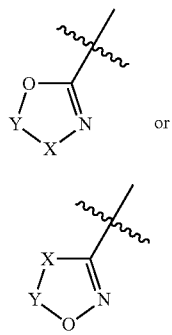

X, at each occurrence, is independently selected from —C(O)—, —CR$_4$R$_5$— and —NR—;

Y, at each occurrence, is independently -C(O)— or —CR$_4$R$_5$—;

provided that both of X and Y are not simultaneously —C(O)—;

R is selected from substituted or unsubstituted alkyl, substituted or unsubstituted haloalkyl, substituted or unsubstituted cycloalkyl, substituted or unsubstituted cycloalkenyl, substituted or unsubstituted aryl, substituted or unsubstituted heteroaryl, substituted or unsubstituted heterocyclyl, —C(O)NR$_6$R$_7$, —C(O)OR$_8$ and —C(O)R$_9$;

ring W is selected from aryl or heteroaryl;

L is selected from —C(O)NR$_{11}$—, —NR$_{11}$C(O)— and —NR$_{11}$CH$_2$—;

ring D is selected from

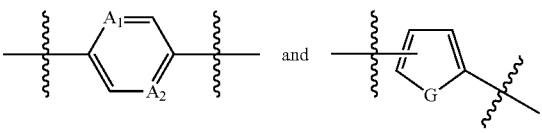

wherein A$_1$ and A$_2$ are independently CR$_3$ or N;

G is selected from S, NR$_{12}$ and O;

R$_1$, which may be same or different at each occurrence, is independently selected from halogen, cyano, nitro, hydroxyl, substituted or unsubstituted alkyl, substituted or unsubstituted haloalkyl, substituted or unsubstituted alkoxy, substituted or unsubstituted haloalkoxy and substituted or unsubstituted cycloalkyl;

R$_2$, which may be same or different at each occurrence, is independently selected from halogen, hydroxyl, cyano, nitro, substituted or unsubstituted alkyl, substituted or unsubstituted haloalkyl, substituted or unsubstituted alkenyl, substituted or unsubstituted alkynyl, substituted or unsubstituted alkoxy, substituted or unsubstituted haloalkoxy, substituted or unsubstituted alkenyloxy, substituted or unsubstituted alkynyloxy, substituted or unsubstituted cycloalkyl, substituted or unsubstituted cycloalkoxy, —NR$_6$R$_7$ and —NHC(O)R$_9$;

R$_3$, which may be same or different at each occurrence, is independently selected from hydrogen, halogen, substituted or unsubstituted alkyl, substituted or unsubstituted alkoxy, substituted or unsubstituted haloalkyl, substituted or unsubstituted haloalkoxy, substituted or unsubstituted cycloalkyl, —NR$_6$R$_7$, —C(O)NR$_6$R$_7$ and —C(O)OR$_8$;

R$_4$ and R$_5$, which may be same or different at each occurrence, are independently selected from hydrogen, halogen, —OR$_{10}$, substituted or unsubstituted alkyl, substituted or unsubstituted haloalkyl, substituted or unsubstituted hydroxyalkyl, —C(O)OR$_8$, —C(O)—NR$_6$R$_7$, substituted or unsubstituted cycloalkyl, substituted or unsubstituted aryl, substituted or unsubstituted heteroaryl and substituted or unsubstituted heterocyclyl; provided that, when any of R$_4$ or R$_5$ in Y is —OR$_{10}$ then R$_{10}$ is not hydrogen;

R$_6$ and R$_7$, which may be same or different at each occurrence, are independently selected from hydrogen, substituted or unsubstituted alkyl and substituted or unsubstituted cycloalkyl; or R$_6$ and R$_7$, together with the nitrogen atom to which they are attached, may form a substituted or unsubstituted, saturated or unsaturated 3 to 12 membered cyclic ring, wherein the unsaturated cyclic ring may have one or two double bonds;

R$_8$, which may be same or different at each occurrence, is independently hydrogen, substituted or unsubstituted alkyl;

R$_9$, which may be same or different at each occurrence, is independently selected from substituted or unsubstituted alkyl, substituted or unsubstituted cycloalkyl, and substituted or unsubstituted aryl;

R$_{10}$ is selected from hydrogen, substituted or unsubstituted alkyl, substituted or unsubstituted cycloalkyl, substituted or unsubstituted aryl, substituted or unsubstituted heteroaryl and substituted or unsubstituted heterocyclyl;

R$_{11}$, at each occurrence, is independently selected from hydrogen, substituted or unsubstituted alkyl and substituted or unsubstituted aryl;

R$_{12}$ is selected from hydrogen, substituted or unsubstituted alkyl, substituted or unsubstituted cycloalkyl, substituted or unsubstituted aryl, substituted or unsubstituted heteroaryl and substituted or unsubstituted heterocyclyl;

'n' is an integer ranging from 0 to 2, both inclusive;

'p' is an integer ranging from 0 to 4, both inclusive; and

'q' is an integer ranging from 1 to 2, both inclusive;

or a pharmaceutically acceptable salt thereof.

According to one embodiment, there are provided compounds having the structure of Formula (II):

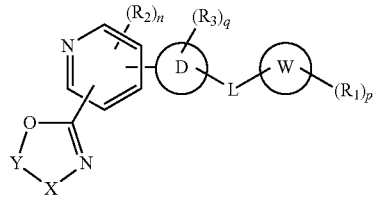
(II)

or its pharmaceutically acceptable salt thereof;
wherein,
L is selected from —C(O)NH—, —NHC(O)— and —NHCH$_2$—;
ring W is selected from aryl or heteroaryl;
ring D, X, Y, R$_1$, R$_2$, R$_3$, 'n', 'p', and 'q' are as defined above.

According to another embodiment, there are provided compounds having the structure of Formula (III):

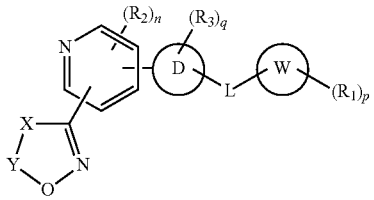
(III)

or its pharmaceutically acceptable salt thereof;
wherein,
L is selected from —C(O)NH—, —NHC(O)— and —NHCH$_2$—;
ring W is selected from aryl or heteroaryl;
ring D, X, Y, R$_1$, R$_2$, R$_3$, 'n', 'p', and 'q' are as defined above.

It should be understood that the Formula (I), Formula (II), and Formula (III) structurally encompasses all tautomers, stereoisomers, enantiomers and diastereomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims.

According to another embodiment there are provided a compound of Formula (II) wherein ring

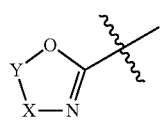

is selected from Formula (i) to (iii)

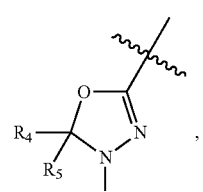
(i)

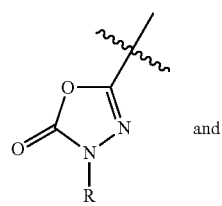
(ii)
and

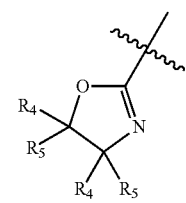
(iii)

where R, R$_4$, and R$_5$ are as defined herein above.

According to another embodiment there are provided a compound of Formula (III) wherein ring

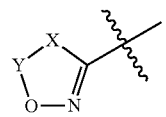

is selected from Formula (Iv) to (vii)

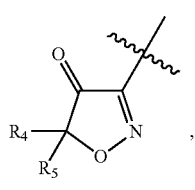
(iv)

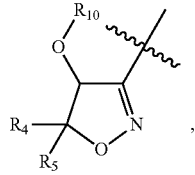
(v)

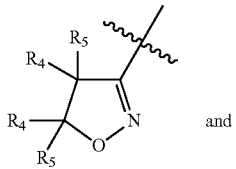
(vi)
and

-continued

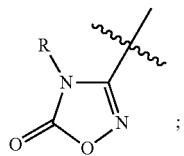

(vii)

where R, $R_4$, $R_5$ and $R_{10}$ are as defined herein above.

According to another embodiment are provided compounds of Formula (I), Formula (II) and/or Formula (III) in which L is —C(O)$NR_{11}$—, wherein $R_{11}$ is hydrogen or substituted or unsubstituted alkyl.

According to another embodiment are provided compounds of Formula (I), Formula (II) and/or Formula (III) in which L is —$NR_{11}$C(O)— wherein $R_{11}$ is hydrogen or substituted or unsubstituted alkyl.

According to another embodiment are provided compounds of Formula (I), Formula (II) and/or Formula (III) in which L is —$NR_{11}CH_2$— wherein $R_{11}$ is hydrogen or substituted or unsubstituted alkyl.

According to another embodiment are provided compounds of Formula (I), Formula (II) and/or Formula (III) in which ring W is aryl wherein the aryl is phenyl; $R_1$ is selected from halogen, cyano, nitro, hydroxyl, substituted or unsubstituted alkyl, substituted or unsubstituted haloalkyl, substituted or unsubstituted alkoxy, substituted or unsubstituted haloalkoxy and substituted or unsubstituted cycloalkyl; and 'p' is 0, 1, 2, or 3.

According to another embodiment are provided compounds of Formula (I), Formula (II) and/or Formula (III) in which ring W is heteroaryl wherein the heteroaryl is pyridyl, oxazolyl, isoxazolyl or thiadiazolyl; $R_1$ is selected from halogen, cyano, nitro, hydroxyl, substituted or unsubstituted alkyl, substituted or unsubstituted haloalkyl, substituted or unsubstituted alkoxy, substituted or unsubstituted haloalkoxy and substituted or unsubstituted cycloalkyl; and 'p' is 0, 1, or 2;

According to another embodiment are provided compounds of Formula (I), Formula (II) and/or Formula (III) in which ring D is

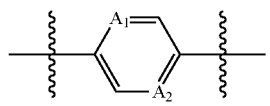

wherein $A_1$ and $A_2$ are independently $CR_3$ or N; $R_3$ is hydrogen, halogen, substituted or unsubstituted alkyl, substituted or unsubstituted haloalkyl and substituted or unsubstituted cycloalkyl; and 'q' is 1 or 2.

According to another embodiment are provided compounds of Formula (I), Formula (II) and/or Formula (III) in which ring D is

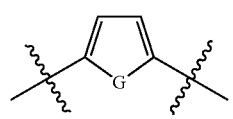

where G is selected from S, $NR_{12}$ and O; wherein $R_{12}$ is hydrogen or substituted or unsubstituted alkyl; $R_3$ is halogen, substituted or unsubstituted alkyl, substituted or unsubstituted haloalkyl and substituted or unsubstituted cycloalkyl and 'q' is 1 or 2.

According to another embodiment are provided compounds of Formula (I) in which $R_2$ is selected from halogen, hydroxyl, cyano, nitro, substituted or unsubstituted alkyl, substituted or unsubstituted haloalkyl, substituted or unsubstituted alkoxy, substituted or unsubstituted haloalkoxy, substituted or unsubstituted cycloalkyl, and —$NR_6R_7$ where $R_6$ and $R_7$ are independently a hydrogen or substituted or unsubstituted alkyl; and 'n' is 0, 1 or 2.

According to another embodiment are provided compounds of Formula (IV):

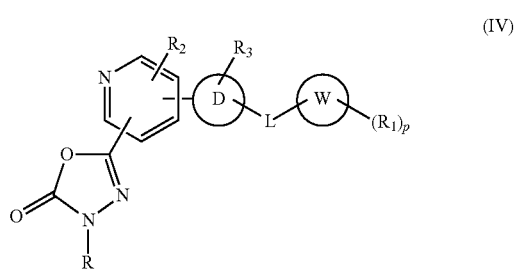

(IV)

wherein R is substituted or unsubstituted alkyl; substituted or unsubstituted haloalkyl, or substituted or unsubstituted cycloalkyl; L is —C(O)NH—, —NHC(O)—, or —$NHCH_2$—; ring W is phenyl, pyridyl, oxazolyl, isoxazolyl or thiadiazolyl; $R_1$ may be same or different and are independently a halogen, substituted or unsubstituted alkyl, substituted or unsubstituted haloalkyl or substituted or unsubstituted cycloalkyl; 'p' is 1, 2, or 3;

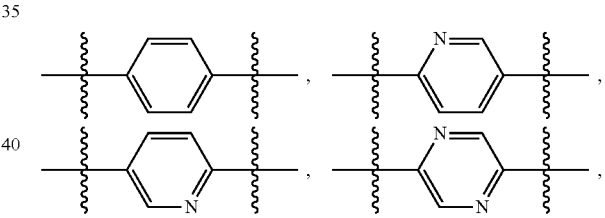

ring D is

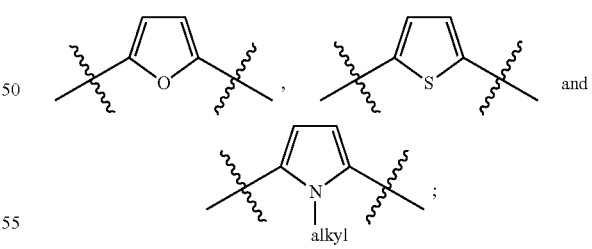

$R_3$ is hydrogen, halogen, substituted or unsubstituted alkyl; 'q' is 1; $R_2$ is halogen, substituted or unsubstituted alkyl, substituted or unsubstituted haloalkyl, substituted or unsubstituted alkoxy, substituted or unsubstituted haloalkoxy, substituted or unsubstituted cycloalkyl, and —$NR_6R_7$ where $R_6$ and $R_7$ are independently a hydrogen or substituted or unsubstituted alkyl; and 'n' is 0, 1 or 2.

In another aspect, the invention provides a pharmaceutical composition comprising at least one compound of Formula (I) and at least one pharmaceutically acceptable excipient.

In another aspect of the invention, there is provided a compound of Formula (I) useful in treating, managing and/or lessening the severity of the diseases, disorders, syndromes or conditions associated with the modulation of CRAC channel.

In another aspect, the invention provides a pharmaceutical composition of a compound of Formula (I) useful in treating, managing and/or lessening the severity of the diseases disorders, syndromes or conditions associated with the modulation of CRAC channel in a subject in need thereof by administering to the subject, one or more compounds described herein in an amount.

In another aspect, the invention provides a method of modulating ion channel activity, for example, CRAC channel, by administering effective amount of a compound of Formula (I) and/or pharmaceutically acceptable salts.

In another aspect, the invention provides a method of modulating the secretion of cytokines, for example IL-2, IL-4, IL-10, IL-13, IL-17, IL-21, IL-23, IL-28, IFN-γ and TNF-α and the like, by regulating the cytokine signalling pathway through calcineurin and NFAT cells.

In another aspect of the invention are processes for the preparation of the compounds described herein.

In another aspect, there are provided processes for the preparation compounds of Formula (I):

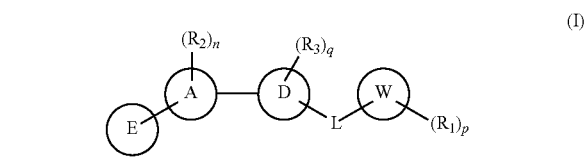

(I)

where ring A, ring D, ring E, ring W, L, $R_1$, $R_2$, $R_3$, 'n', 'p', and 'q' are as described herein above, the process comprising the steps:

a) coupling of a borate compound of Formula (1) with halo compound of Formula (2) where X' is halogen, to give compound of Formula (I) by using suitable reagents $Pd(PPh_3)_2Cl_2$, $Pd_2dba_3$, $Pd(PPh_3)_4$, or $Pd(OAc)_2$ and suitable ligand 2,2'-bis(diphenylphosphino)-1,1'-binaphthyl (BINAP), xanthophos, or triphenylphosphine

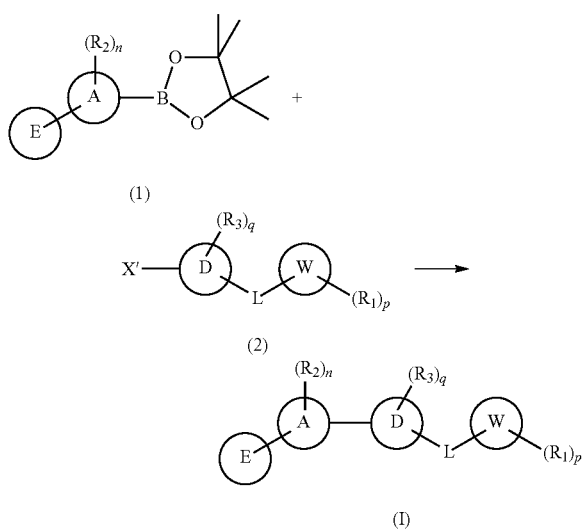

b) alternatively, coupling of a halo compound of Formula (3) where X' is halogen, with compound of Formula (2) where p is pinacolatoboronate or stannane, to give compound of Formula (I) by using suitable reagents $Pd(PPh_3)_2Cl_2$, $Pd_2dba_3$, $Pd(PPh_3)_4$, or $Pd(OAc)_2$ and a suitable ligand 2,2'-bis(diphenylphosphino)-1,1'-binaphthyl (BINAP), xanthophos, or triphenylphosphine

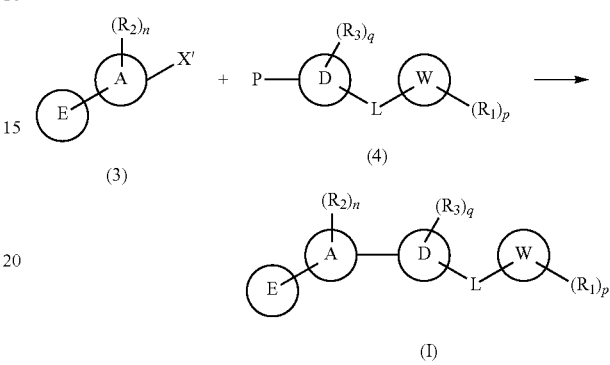

DETAILED DESCRIPTION OF THE INVENTION

Definitions and Abbreviations

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the present invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl(t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl(allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting examples of such groups are methoxy, ethoxy and propoxy and the like. Unless set forth or recited to the contrary, all alkoxy groups described or claimed herein may be straight chain or branched, substituted or unsubstituted.

The term "alkenyloxy" refers to an alkenyl group attached via an oxygen linkage. Non-limiting examples of such groups are vinyloxy, allyloxy, 1-butenyloxy, 2-butenyloxy, isobutenyloxy, 1-pentenyloxy, 2-pentenyloxy, 3-methyl-1-butenyloxy, 1-methyl-2-butenyloxy, 2,3-dimethylbutenyloxy, 1-hexenyloxy and the like. Unless set forth or recited to the contrary, all alkenyloxy groups described or claimed herein may be straight chain or branched, substituted or unsubstituted.

The term "alkynyloxy" refers to an alkynyl group attached via an oxygen linkage. Non-limiting examples of such groups are acetylenyloxy, propynyloxy, 1-butynyloxy, 2-butynyloxy, 1-pentynyloxy, 2-pentynyloxy, 3-methyl-1-butynyloxy, 1-hexynyloxy, 2-hexynyloxy, and the like. Unless set forth or recited to the contrary, all alkynyloxy groups described or claimed herein may be straight chain or branched, substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapththyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkoxy" refers to an cycloalkyl, defined herein, group attached via an oxygen linkage. Non-limiting examples of such groups are cyclopropoxy, cyclobutoxy, cyclopentoxy, cyclohexyloxy and the like. Unless set forth or recited to the contrary, all alkoxy groups described or claimed herein may be straight chain or branched, substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms.

The term "haloalkoxy" refers to an haloalkyl, defined herein, group attached via an oxygen linkage. Non-limiting examples of such groups are monohaloalkoxy, dihaloalkoxy or polyhaloalkoxy including perhaloalkoxy. Unless set forth or recited to the contrary, all haloalkoxy groups described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting examples of a hydroxyalkyl include 2-hydroxyethyl, 3-hydroxypropyl, 2-hydroxypropyl, and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

A "3-12 membered cyclic ring" as used herein refers to a monocyclic, bicyclic, polycyclic heteroaryl or heterocyclic ring systems. Thease heteroaryl or heterocyclic ring as described herein.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —$CF_2$—, —C(O)—, —S(O)—, $S(O)_2$, —C(=N-alkyl)-, or —C(=N-cycloalkyl), etc. In addition heterocyclic ring may also be fused with aromatic ring. Non-limiting examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached by any atom of the heterocyclic ring that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached by any atom of the heteroaryl ring that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O) R$^y$, —NR$^x$C(S)R$^y$, —NR$^x$C(S)NR$^y$R$^z$, S(O)$_2$NR$^x$R$^y$, —OR$^x$, —OC(O)R$^x$, —OC(O)NR$^x$R$^y$, —R$^x$C(O)OR$^y$, —R$^x$C(O) NR$^y$R$^z$, —R$^x$C(O)R$^y$, —SR$^x$, and —S(O)$_2$R$^x$; wherein each occurrence of R$^x$, R$^y$ and R$^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl. The aforementioned "substituted" groups cannot be further substituted. For example, when the substituent on "substituted alkyl" is "aryl" or "alkenyl", the aryl or alkenyl cannot be substituted aryl or substituted alkenyl, respectively.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "Tautomer" refers to a compound that undergo rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disease, disorder, condition or syndrome includes: (a) delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease disorder or condition or at least one of its clinical or subclinical symptoms thereof; and/or (d) relieving the disease, i.e., causing regression of the state, disorder or condition or at least one of its clinical or subclinical symptoms.

The term "modulate" or "modulating" or "modulation" refers to a decrease or inhibition in the amount, quality, or effect of a particular activity, function or molecule; by way of illustration that block or inhibit calcium release-activated calcium (CRAC) channel. Any such modulation, whether it be partial or complete inhibition is sometimes referred to herein as "blocking" and corresponding compounds as "blockers". For example, the compounds of the invention are useful as modulators of the CRAC channel.

The term "subject" includes mammals, preferably humans and other animals, such as domestic animals; e.g., household pets including cats and dogs.

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

Unless otherwise stated, in the present application "protecting group" refers to the groups intended to protect an otherwise labile group, e.g., an amino group, a carboxy group and the like, under specific reaction conditions. Various protecting groups along with the methods of protection and deprotection are generally known to a person of ordinary skilled in the art. Incorporated herein in this regard as reference is Greene's Protective Groups in Organic Synthesis, 4th Edition, John Wiley & Sons, New York. In the present invention, preferred amino protecting groups are t-butoxycarbonyl, benzyloxycarbonyl, acetyl and the like; while preferred carboxy protecting groups are esters, amides and the like.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting examples of pharmaceutically acceptable salts are inorganic, organic acid addition salts formed by addition of acids including hydrochloride salts. Non-limiting examples of pharmaceutically acceptable salts are inorganic, organic base addition salts formed by addition of bases. The compounds of the invention may also form salts with amino acids. Pharmaceutically acceptable salts may be obtained using standard procedures well known in the art, for example by reacting a sufficiently basic compound such as an amine with a suitable acid affording a physiologically acceptable anion.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography. Tautomeric forms and mixtures of compounds described herein are also contemplated.

Pharmaceutical Compositions

The invention relates to pharmaceutical compositions containing the compound of Formula (I). In particular, the pharmaceutical compositions contain a therapeutically effective amount of at least one compound of Formula (I) and at least one pharmaceutically acceptable excipient (such as a carrier or diluent). Preferably, the pharmaceutical compositions include the compound(s) described herein in an amount sufficient to modulate the calcium release-activated calcium (CRAC) channel to treat CRAC channel mediated diseases such as inflammatory diseases, autoimmune diseases, allergic disorders, organ transplant, cancer and cardiovascular disorders when administered to a subject.

The compound of the invention may be incorporated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes a pharmaceutical agent that does not itself induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be Formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be administered in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral Formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid Formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

For administration to human patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg, more typically 1.0 mg to 1000 mg, and most typically 10 mg to 500 mg, according to the potency of the active component or mode of administration.

Suitable doses of the compounds for use in treating the diseases disorders, syndromes and conditions described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects for the patient. For example, the daily dosage of the CRAC channel modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Method of Treatment

In a further embodiment, the invention is directed to the treatment or prophylaxis of inflammatory conditions by administering an effective amount of a compound of the present invention.

Inflammation is part of the normal host response to infection and injury or exposure to certain substances prone to cause it. Inflammation begins with the immunologic process of elimination of invading pathogens and toxins to repair damaged tissue. Hence, these responses are extremely ordered and controlled. However, excessive or inappropriate inflammation contributes to a range of acute and chronic human diseases and is characterized by the production of inflammatory cytokines, arachidonic acid-derived eicosanoids (prostaglandins, thromboxanes, leukotrienes, and other oxidized derivatives), other inflammatory agents (e.g., reactive oxygen species), and adhesion molecules. As used herein, the term "inflammatory conditions" is defined as a disease or disorder or abnormality characterized by involvement of inflammatory pathways leading to inflammation, and which may result from, or be triggered by, a dysregulation of the normal immune response.

The compound(s) of the present invention are useful in treatment of inflammatory conditions including, but not limited to, diseases of many body systems such as (musculoskeletal) arthritis, myositis, rheumatoid arthritis, osteoarthritis, gout, gouty arthritis, acute pseudogout, Reiter's syndrome, ankylosing spondylitis, psoriatic arthritis, dermatomyositis; (pulmonary) pleuritis, pulmonary fibrosis or nodules, restrictive lung disease, chronic obstructive pulmonary disease (COPD), acute respiratory distress syndrome (ARDS), (cardiovascular) aortic valve stenosis, restenosis, arrhythmias, coronary arteritis, myocarditis, pericarditis, Raynaud's phenomenon, systemic vasculitis, angiogenesis, atherosclerosis, ischaemic heart disease, thrombosis, myocardial infarction; (gastrointestinal) dysmotility, dysphagia, inflammatory bowel diseases, pancreatitis, (genitourinary) interstitial cystitis, renal tubular acidosis, urosepsis, (skin) purpura, vasculitis scleroderma, eczema, psoriasis, (neurologic) central nervous system disorders, cranial and peripheral neuropathies, peripheral neuropathy, radiculopathy, spinal cord or cauda equina compression with sensory and motor loss, multiple sclerosis (MS) (mental) cognitive dysfunction, Alzheimer's disease, (neoplastic) lymphoma, inflammation associated with cancer, (ophthalmologic) iridocyclitis, keratoconjunctivitis sicca, uveitis, (hematologic) chronic anemia, thrombocytopenia, (renal) amyloidosis of the kidney, glomerulonephritis, kidney failure and other diseases such as tuberculosis, leprosy, sarcoidosis, syphilis, Sjögren's syndrome, cystitis, fibromyalgia, fibrosis, septic shock, endotoxic shock, surgical complications, systemic lupus erthymotosus (SLE), transplantation associated arteriopathy, graft vs. host reaction, allograft rejection, chronic transplant rejection.

The inflammatory bowel diseases also include Crohn's disease, ulcerative colitis, indeterminate colitis, necrotizing enterocolitis, and infectious colitis.

"Allergic disorders" is defined as disorders/diseases that are caused by a combination of genetic and environmental factors resulting in a hypersensitivity disorder of the immune system. Allergic diseases are characterized by excessive immunoglobulin E (IgE) production, mast cell degranulation, tissue eosinophilia and mucus hypersecretion, resulting in an extreme inflammatory response. These responses also take place during infection with multicellular parasites, and are linked to the production of a characteristic set of cytokines by T helper (Th) 2 cells. For example asthma is a chronic inflammatory condition of the lungs, characterized by excessive responsiveness of the lungs to stimuli, in the form of infections, allergens, and environmental irritants. Allergic reactions can also result from food, insect stings, and reactions to medications like aspirin and antibiotics such as penicillin. Symptoms of food allergy include abdominal pain, bloating, vomiting, diarrhea, itchy skin, and swelling of the skin during hives. Food allergies rarely cause respiratory (asthmatic) reactions, or rhinitis. Insect stings, antibiotics, and certain medicines produce a systemic allergic response that is also called anaphylaxis. The main therapeutic interest around CRAC in allergic disorders, originates from its role in lymphocytes and mast cells, CRAC activation being a requirement for lymphocyte activation.

The compound(s) of the present invention are useful in treatment of allergic disorders including, but not limited to, atopic dermatitis, atopic eczema, Hay fever, asthma, urticaria (including chronic idiopathic urticaria), vernal conjunctivitis, allergic rhinoconjunctivitis, allergic rhinitis (seasonal and perennial), sinusitis, otitis media, allergic bronchitis, allergic cough, allergic bronchopulmonary aspergillosis, anaphylaxis, drug reaction, food allergies and reactions to the venom of stinging insects.

In yet another embodiment, the invention is directed to the treatment of "immune disorders" by administering an effective amount of a compound of the present invention.

The compounds of this invention can be used to treat subjects with immune disorders. As used herein, the term "immune disorder" and like terms mean a disease, disorder or condition caused by dysfunction or malfunction of the immune system as a whole or any of its components including autoimmune disorders. Such disorders can be congenital or acquired and may be characterized by the component(s) of the immune system getting affected or by the immune system or its components getting overactive. Immune disorders include those diseases, disorders or conditions seen in animals (including humans) that have an immune component and those that arise substantially or entirely due to immune system-mediated mechanisms. In addition, other immune system mediated diseases, such as graft-versus-host disease and allergic disorders, will be included in the definition of immune disorders herein. Because a number of immune disorders are caused by inflammation or lead to inflammation, there is some overlap between disorders that are considered immune disorders and inflammatory disorders. For the purpose of this invention, in the case of such an overlapping disorder, it may be considered either an immune disorder or an inflammatory disorder. An autoimmune disorder is a condition that occurs when the immune system mistakenly attacks and destroys its own body cells, tissues and/or organs. This may result in temporary or permanent destruction of one or more types of body tissue, abnormal growth of an organ, changes in organ function, etc. For example, there is destruction of insulin producing cells of the pancreas in Type 1 diabetes mellitus. Different autoimmune disorders can target different tissues, organs or systems in an animal while some autoimmune disorders target different tissues, organs or systems in different animals. For example, the autoimmune reaction is directed against the gastrointestinal tract in Ulcerative colitis and the nervous system in multiple sclerosis whereas in systemic lupus erythematosus (lupus), affected tissues and organs may vary among individuals with the same disease. For example, one person with lupus may have affected skin and joints whereas another may have affected kidney, skin and lungs.

Specific autoimmune disorders that may be ameliorated using the compounds and methods of this invention include without limitation, autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland), autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome), autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia) and autoimmune disorders of the blood vessels (e.g., temporal arteritis, anti-phospholipid syndrome, vasculitides such as Wegener's granulomatosis, and Behcet's disease).

"Treatment of an immune disorder" herein refers to administering a compound or a composition of the invention alone or in combination with other agents to a subject, who has an immune disorder, a sign or symptom of such a disease or a risk factor towards such a disease, with a purpose to cure, relieve, alter, affect, or prevent such disorder or sign or symptom of such a disease, or the predisposition towards it.

In another embodiment, the invention is directed to the treatment of cancer by administering an effective amount of a compound of the present invention.

It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

The compound(s) of the present invention may be useful in treatment of cancers and/or its metastasis including, but not limited to, breast cancer, lung cancer, pancreatic cancer, ovarian cancer, colon cancer, neck cancer, kidney cancer, bladder cancer, thyroid, blood cancer, skin cancer and the like. In yet another embodiment, the invention is directed to the treatment or prophylaxis of allergic disorders by administering an effective amount of a compound of the present invention.

In yet another embodiment, the invention is directed to the treatment or prophylaxis of cardiovascular diseases or disorders by administering an effective amount of a compound of the present invention.

The compounds of this invention can be used to treat subjects with cardiovascular disorders. "Cardiovascular disorder" refers to a structural and functional abnormality of the heart and blood vessels, comprised of diseases including but not limited to, atherosclerosis, coronary artery disease, arrhythmia, heart failure, hypertension, diseases of the aorta and its branches, disorders of the peripheral vascular system, aneurysm, endocarditis, pericarditis, heart valve disease. It may be congenital or acquired. One of the main pathological feature of all these diseases is clogged and hardened arteries, obstructing the blood flow to the heart. The effects differ depending upon which vessels are clogged with plaque. The arteries carrying oxygen rich blood, if clogged, result in coronary artery disease, chest pain or heart attack. If the arteries reaching the brain are affected, it leads to transient ischemic attack or stroke. If the vessels in arms or legs are affected, leads to peripheral vascular disease. Because a number of cardiovascular diseases may also be related to or arise as a consequence of thrombocytopathies, there is some overlap between disorders that are considered under heading cardiovascular disorders and thrmobocytopathies. For the purpose of this invention, in the case of such an overlapping disorder, it may be considered either a cardiovascular disorder or a thrombocytopathy.

STIM1 is located on the endoplasmic reticulum (ER) and functions as a calcium sensor. Orai1 is a pore forming subunit of calcium channel located on the plasma membrane, the depletion of calcium in the endoplasmic reticulum is sensed by STIM1, and calcium enters via Orai1 to refill the endoplasmic reticulum. This pathway of filling the calcium is called store operated calcium entry (SOCE), which plays an important role in calcium homeostasis, cellular dysfunction and has a significant importance in cardiovascular diseases. In cardiomyocytes, calcium is not only involved in excitation-contraction coupling but also acts as a signalling molecule promoting cardiac hypertrophy. Hypertrophic hearts are susceptible to abnormalities of cardiac rhythm and have impaired relaxation. Vascular smooth muscle cells (VSMCs) are responsible for the maintenance of vascular tone. VSMCs disorders, usually manifested as a phenotype change, are involved in the pathogenesis of major vascular diseases such as atherosclerosis, hypertension and restenosis. SOCE was also found increased in metabolic syndrome (MetS) swine coronary smooth muscle cells. The compound of this invention can be used to treat neointimal hyperplasia, occlusive vascular diseases, MetS—which is a combination of medical disorders including coronary artery disease, stroke and type 2 diabetes, abdominal aortic aneurysm, angina, transient ischemic attack, stroke, peripheral artery occlusive disease which includes inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout, myocardial infarction, portal vein thrombosis which leads to hypertension, pulmonary hypertension, deep vein thrombosis, jugular vein thrombosis, systemic sepsis, pulmonary embolism, and papilledema, Budd-Chiari syndrome, Paget-Schroetter disease, cerebral venous sinus thrombosis ischemic cardiomyopathy, hypertrophic cardiomyopathy, arrhythmogenic right ventricular cardiomyopathy, Prinzmetal angina, angina pectoris, chronic venous insufficiency, acute coronary syndrome, endocarditis, conceptual apraxia, pulmonary valve stenosis, thrombophlebitis, ventricular tachycardia, temporal arteritis, tachycardia, paroxysmal atrial fibrillation, persistent atrial fibrillation, permanent atrial fibrillation, respiratory sinus arrhythmia, carotid artery dissection, cerebrovascular diseases include, hemorrhagic stroke and ischemic stroke (where the thrombo-inflammatory cascade results in infarct growth), cardiomegaly, endocarditis, pericarditis, pericardial effusion. Valvular heart disease, vascular diseases or vascular inflammation is the result of ruptured atherosclerotic plaque which initiates thrombus formation. Platelet activation play an important role in vascular inflammation leading to myocardial infarction and ischaemic stroke, the compound of this invention will prevent platelet activation and plaque formation and would also be useful to treat all peripheral vascular diseases (PVD), pulmonary thromboembolism, and venous thrombosis.

"Treatment of cardiovascular disorders" herein refers to administering a compound or a composition of the invention alone or in combination with other agents to a subject, who has a cardiovascular disease, a sign or symptom of such a disease or a risk factor towards such a disease, with a purpose to cure, relieve, alter, affect, or prevent such disorder or sign or symptom of such a disease, or the predisposition towards it.

In yet another embodiment, the invention is directed to the treatment of "thrombocytopathies" by administering an effective amount of a compound of the present invention.

Thrombocytopathies: The compounds of this invention can be used to treat subjects with thrombocytopathies. Thrombocytopathy is an abnormality of platelets or its functions. It may be congenital or acquired. It may cause a thrombotic or a bleeding tendency or may be part of a wider disorder such as myelodysplasia. Thrombocytopathies include such vascular disorders that arise due to dysfunction of platelets or coagulation system or diseases or complications that arise as a result of partial or complete restriction of blood flow to different organs or systems due to such thrombocytopathies. Thrombocytopathies will thus include without limitation; diseases due to superficial vein thrombosis, diseases due to deep vein thrombosis, diseases due to arterial thrombosis, peripheral vascular diseases, thrombophilia, thrombophlebitis, embolisms, thromboembolism, ischemic cardiovascular diseases including but not limited to myocardial ischemia, angina, ischemic cerebrovascular diseases including but not limited to stroke, transient ischemia attack, cerebral venous sinus thrombosis (CVST) and complications arising due to thrmobocytopathies. Besides this, the disorder related to venous or arterial thrombus formation can be inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout.

Under normal circumstances, when the endothelial cells lining blood vessels are breached, platelets interact with von Willebrand factor (vWF) via the membrane glycoprotein 1b complex to help seal the breach. Glycoprotein IIb/Ia complex attracts other platelets, which combine to form aggregates. The platelets contain granules which break down to release fibrinogen, vWF, platelet-derived growth factor adenosine 5'-diphosphate (ADP), calcium and 5-hydroxytryptamine (5-HT)-serotonin. All this helps to promote the formation of a haemostatic plug (primary haemostasis). Activated platelets also synthesise thromboxane A2 from arachidonic acid as well as presenting negatively charged phospholipids on the outer leaflet of the platelet membrane bilayer. This negative surface provides binding sites for enzymes and cofactors of the coagulation system. The total effect is therefore to stimulate the coagulation system to form a clot (secondary haemostasis).

Thus physiological platelet activation and thrombus formation are essential to stop bleeding in case of vascular injury, whereas under pathological conditions this may lead to vessel occlusion due to inadequate triggering of the same process in diseased vessels leading to thrombosis, thromboembolism or tissue ischemia of vital organs. A central step in platelet activation is agonist-induced elevation of the intracellular Ca(2+) concentration. This happens on the one hand through the release of Ca(2+) from intracellular stores and on the other hand through Ca(2+) influx from the extracellular space. In platelets, the major Ca(2+) influx pathway is through store operated Ca(2+) entry (SOCE), induced by store depletion. STIM1 is the Ca(2+) sensor in the endoplasmic reticulum (ER) membrane, whereas Orai1 is the major store operated Ca(2+) (SOC) channel in the plasma membrane, which play a key role in platelet SOCE.

"Treatment of thrombocytopathy" herein refers to administering a compound or a composition of the invention alone or in combination with other agents to a subject, who has a thrombocytopathy, a sign or symptom or complication of such a disease or a risk factor towards such a disease, with the purpose to cure, relieve, alter, affect, or prevent such a disorder or sign or symptom, or the predisposition towards it.

General Methods of Preparation

The compounds of the present invention, including compounds of general Formula (I) and specific examples are prepared through the reaction sequences illustrated in synthetic Schemes 1 to 4 wherein ring A, ring E, ring D, ring W, L, $R_1$, $R_2$, $R_3$, 'n' 'p' and 'q' are as defined herein above. Starting materials are commercially available or may be prepared by the procedures described herein or by the procedures known in the art. Furthermore, in the following synthetic schemes, where specific acids, bases, reagents, coupling agents, solvents, etc., are mentioned, it is understood that other acids, bases, reagents, coupling agents, solvents etc., known in the art may also be used and are therefore included within the scope of the present invention. Variations in reaction conditions and parameters like temperature, pressure, duration of reaction, etc., which may be used as known in the art are also within the scope of the present invention. All the isomers of the compounds described in these schemes, unless otherwise specified, are also encompassed within the scope of this invention.

The compounds obtained by using the general reaction sequences may be of insufficient purity. These compounds can be purified by using any of the methods for purification of organic compounds known in the art, for example, crystallization or silica gel or alumina column chromatography using different solvents in suitable ratios. Unless mentioned otherwise, RT (RT) refers to a temperature in the range of 22 to 27° C.

$^1$H-NMR spectra of the compounds of the present invention were recorded using a BRUCKNER instrument (model: Avance-III), 400 MHz. Liquid chromatography—mass spectra (LCMS) of the compounds of the present invention were recorded using Agilent ion trap model 6320 and Thermo Scientific Single Quad model MSQ plus instruments. IUPAC nomenclature for the compounds of the present invention were used according to ChemBioDraw Ultra 12.0 software.

Scheme 1

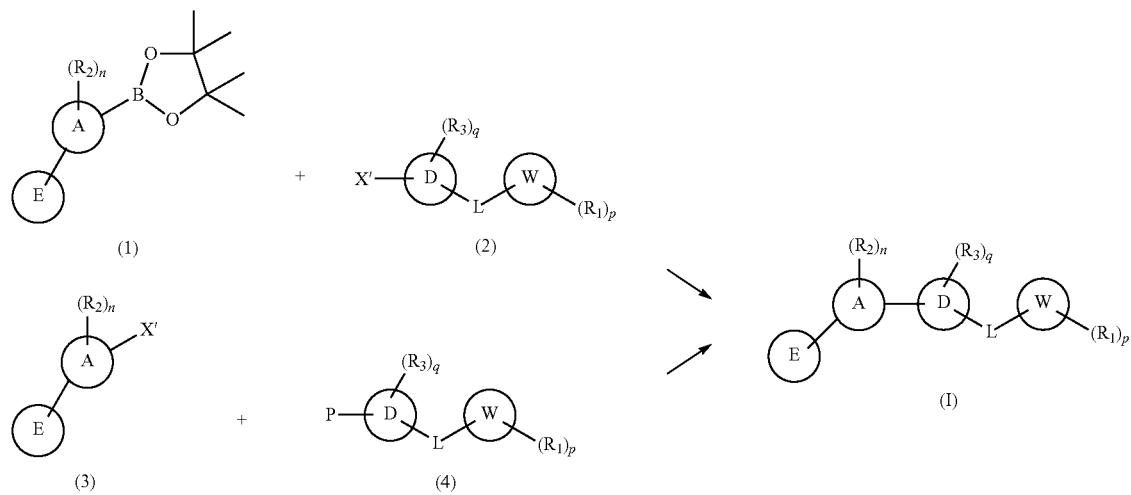

X' is halogen; P is pinacolatoboronate or stannane;

The compounds of Formula (I) can be prepared by the reaction of borate derivative of Formula (1) with various halobenzamides of Formula (2) as depicted in Scheme 1. Alternatively, the compounds of the Formula (I) can also be prepared by the reaction of the halo derivatives of the Formula (3) with borate/stannane derivatives of the Formula (4) as shown in Scheme 1. The same transformation may also be carried out by other suitable coupling methods known in the art.

The said reaction can be mediated by a suitable catalyst known in the art such as $Pd(PPh_3)_2Cl_2$, $Pd_2dba_3$, $Pd(PPh_3)_4$, $Pd(OAc)_2$ or mixture(s) thereof; a suitable ligand known in the art such as 2,2'-bis(diphenylphosphino)-1,1'-binaphthyl (BINAP), xanthophos, triphenylphosphine or mixture(s) thereof; in the presence of suitable solvent using suitable base, preferably inorganic bases such as alkalimetal carbonates like sodium carbonate, cesium carbonate and phosphates like potassium phosphate or mixture(s) thereof.

Scheme 2

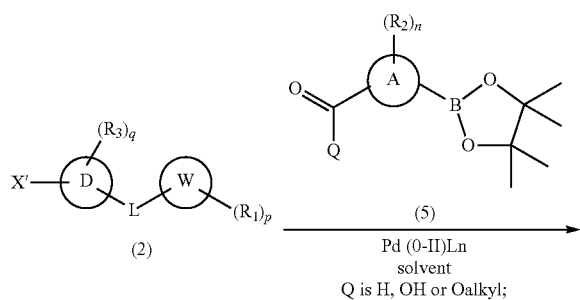

Q is H, OH or Oalkyl;

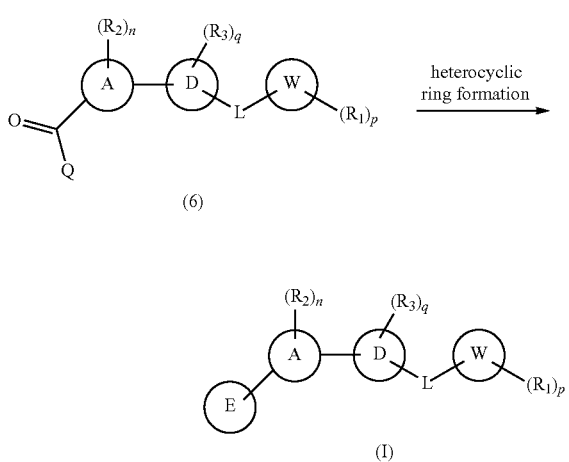

In an alternative approach, the compounds of the present invention can also be prepared as depicted in Scheme 2. Thus, the borate complex of Formula (5) is prepared from the corresponding halo derivatives via a metal catalysed boration reaction or known methods in the art. The coupling reaction of haloderivatives of the Formula (2) with borate derivatives of the Formula (5) are carried out by following the methods known in the art or as described in the Scheme 1 to afford the compounds of the Formula (6). The compounds of the Formula (6) can be converted to compounds of Formula (I) by following the procedure known in the art.

Scheme 3

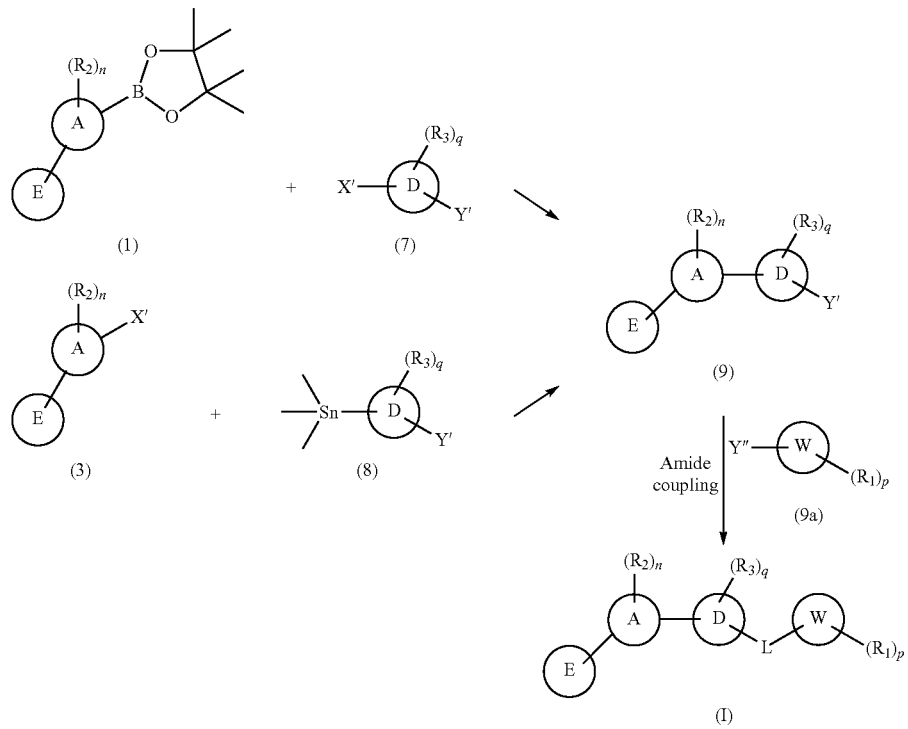

X' is halogen;
Y' is either NHR$_{11}$; or COOH, COOalkyl or COCl
Y" is either COOH, COOalkyl, COCl; or NHR$_{11}$ Another alternative approach is shown in Scheme 3 to prepare compound of Formula (I) by reacting a borate compound of the Formula (1) with halo compound of the Formula (7) followed by amide coupling reaction. Alternatively, the compounds of the present invention is prepared by reaction of halo derivatives of the Formula (3) with stannane derivatives of the Formula (8) followed by amide coupling reaction as depicted in Scheme 3. These coupling reaction are carried out as per the methods known in the art or as described in the Scheme 1. This compounds of the Formula (9) are transformed to compound of Formula (1) using the techniques known in the art.

For example, this amide coupling reaction of compounds of the Formula (9) and Formula (9a) is carried out by condensing an amino group or a protected amino group with a carboxylate group like carboxylic acid or an activated carboxylic acid or an ester present on either intermediate (9) or (9a). Such groups are represented by Y' and Y on intermediate (9) and (9a). However, in a few preferred aspects of the present invention, such amide coupling reactions are accomplished in either of the following ways—when Y' is an amino group or a protected amino group and Y is a carboxylate group like carboxylic acid or an activated carboxylic acid or an ester group—or when Y' is an carboxylate group like carboxylic acid or an activated carboxylic acid or an ester group and Y amino group or a protected amino group:

(a) condensation of Y' and Y groups in the presence of a suitable activating reagent used in peptide linkage syntheses, e.g., hydroxybenzotriazole and a coupling reagent like carbodiimides such as EDC, DCC or mixture(s) thereof; or (b) halogenation of the acid derivatives at Y' or Y" of the compounds of Formula (9) or (9a) with thionyl chloride, oxalyl chloride and the like followed by condensation with the amino or protected amino group at Y" or Y', respectively; or (c) reaction at Y' or Y" of the compounds of Formula (9) or (9a) with corresponding amine derivatives at Y' or Y" of the compounds of Formula (9a) or (9) respectively, in presence of trimethyl aluminium;

Such reactions are carried out in one or more suitable solvents using suitable base for example triethylamine, N-ethyldiisopropylamine; 4-dialkylaminopyridines like 4-dimethylaminopyridine, pyridine or mixture(s) thereof.

Scheme 4

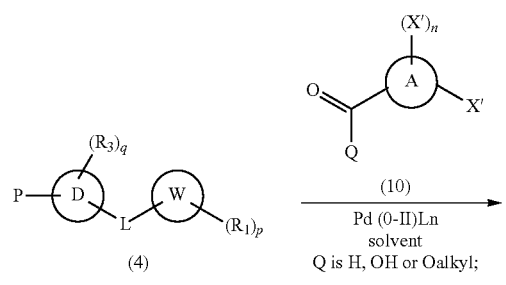

Q is H, OH or Oalkyl;

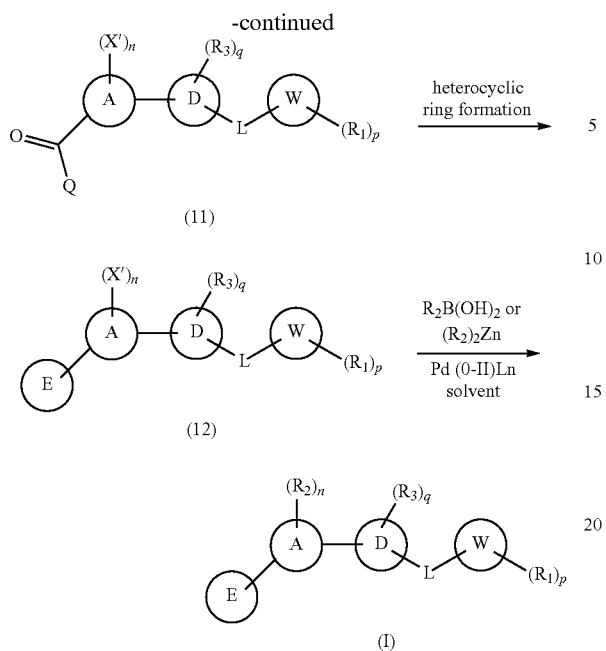

X' is halogen; P is pinacolatoboronate or stannane;

Another alternative approach is shown in Scheme 4 to prepare the compound of Formula (I) by reaction of borate/stannane derivatives of the Formula (4) with the various halide derivatives of the Formula (10) followed by successive heterocyclic ring formation and coupling of the halo derivative (12) with either boronic acid or alkyl zinc.

The coupling reaction of the halide derivatives of the Formula (10) with borate/stannane derivatives of the Formula (4) are carried out as per the methods known in the art or as described in the Scheme 1 to afford compounds of the Formula (11). The compounds of the Formula (11) can be converted to compounds of Formula (12) by following the procedure known in the art. The coupling reaction of halo derivatives of Formula (12) with the corresponding boronic acids/alkyl zinc are carried out to afford the compounds of the Formula (I) as per the methods known in the art or as described in the Scheme 1.

Experimental

The invention is further illustrated by the following examples which are provided merely to be exemplary of the invention and do not limit the scope of the invention. The examples set forth below demonstrate the synthetic procedures for the preparation of the representative compounds. Certain modifications and equivalents will be apparent to those skilled in the art and are intended to be included within the scope of the invention. The aforementioned patents and patent applications are incorporated herein by reference.

Unless otherwise stated, work-up implies the following operations: distribution of the reaction mixture between the organic and aqueous phase, separation of layers, drying the organic layer over sodium sulfate, filtration and evaporation of the organic solvent. Purification, unless otherwise mentioned, implies purification by silica gel chromatographic techniques, generally using ethyl acetate/petroleum ether mixture of a suitable polarity as the mobile phase.

Intermediates

Intermediate 1a & 1b & 1c 5-(5-Bromo-6-ethylpyridin-3-yl)-3-methyl-1,3,4-oxadiazol-2(3H)-one (1a) and 5-(5-(5-Aminopyrazin-2-yl)-6-ethylpyridin-3-yl)-3-methyl-1,3,4-oxadiazol-2(3H)-one (1b) and 5-(6-Ethyl-5-(4,4,5,5-tetramethyl-1,3,2-dioxaborolan-2-yl)pyridin-3-yl)-3-methyl-1,3,4-oxadiazol-2(3H)-one (1c)

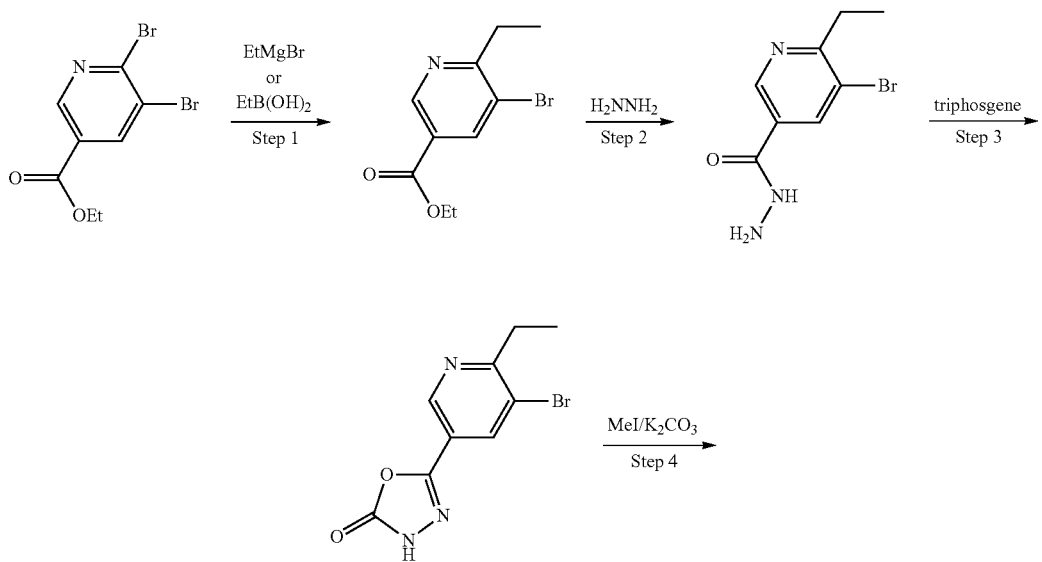

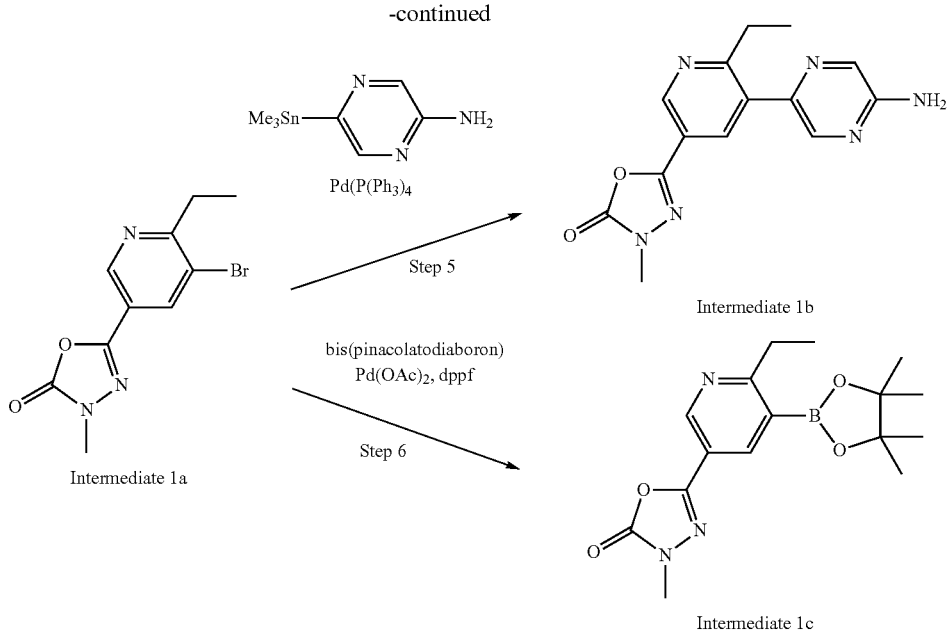

Intermediate 1a

Intermediate 1b

Intermediate 1c

Step-1: Ethyl 5-bromo-6-ethylnicotinate:

Method-1: To a 0° C. cooled solution of ethyl-5,6-dibromonicotinate (1.0 g, 3.24 mmol, 1.0 eq., prepared by following the procedure described in WO2011024004) in THF (10 mL) was added [1,3-bis(diphenylphosphino)propane]dichloronickel (II) (351 mg, 0.65 mmol, 0.2 eq) and the solution was stirred for 5 min. Ethyl magnesium bromide (1M in THF, 3.88 mL, 3.88 mmol, 1.2 eq) was then added drop-wise to the above mixture at 0° C. The resulting mixture was continued to stir at the same temperature for 3 h. Water (10 mL) was then added to the above mixture, followed by ethyl acetate (20 mL). The layers were separated and the aqueous layer was extracted with ethyl acetate (2×10 mL) and the combined organic layers were washed with brine (20 mL), dried ($Na_2SO_4$) and filtered. The filtrate was evaporated and the crude residue was purified by flash column chromatography (silica gel, diethyl ether-hexane system as eluent) to afford 500 mg (60%) of the desired product as a white solid. $^1$HNMR (400 MHz, $CDCl_3$) δ 9.06 (d, J=1.5 Hz, 1H), 8.40 (d, J=1.5 Hz, 1H), 4.42 (q, J=7.0 Hz, 2H), 3.05 (q, J=7.0 Hz, 2H), 1.43 (t, J=7.0 Hz, 3H), 1.28 (t, J=7.0 Hz, 3H); GC-MS (m/z) 257, 259 [M+, $Br^{79, 81}$].

Method-2: A solution of ethyl-5,6-dibromonicotinate (6.0 g, 19.4 mmol, 1.0 eq; prepared by following the procedure described in WO2011024004), ethylboronic acid (1.72 g, 23.3 mmol, 1.2 eq) and potassium carbonate (8.0 g, 58.3 mmol, 3.0 eq) in 1,4-dioxane (10 mL) in a oven dried sealed tube was subjected to three cycles of evacuation-backfilling with argon, and then tetrakis(triphenylphosphine)palladium (0) (2.24 g, 1.94 mmol, 0.1 eq) was added. The sealed tube was sealed and the mixture was stirred and heated in an oil bath to 110° C. After three days of stirring at the same temperature, the reaction was cooled to RT and filtered through Celite®. The filtrate was evaporated and the resultant residue was purified by flash column chromatography (silica gel, ethyl acetate-hexane system as eluent) to afford 1.90 g (38%) of the desired product as a white solid. $^1$HNMR (400 MHz, $CDCl_3$) δ 9.06 (d, J=1.5 Hz, 1H), 8.40 (d, J=1.5 Hz, 1H), 4.42 (q, J=7.0 Hz, 2H), 3.05 (q, J=7.0 Hz, 2H), 1.43 (t, J=7.0 Hz, 3H), 1.28 (t, J=7.0 Hz, 3H); GC-MS (m/z) 257, 259 [M+, $Br^{79, 81}$].

Step-2: 5-Bromo-6-ethylnicotinohydrazide: A mixture of ethyl 5-bromo-6-ethylnicotinate (4.1 g, 15.8 mmol, 1.0 eq) and hydrazine hydrate (3.73 mL, 74.7 mmol, 4.7 eq) in ethanol (30 mL) was heated to 8° C. and further maintained overnight. The reaction mixture was cooled to RT and the solvent was removed on rotavapor. The residue was taken in ethyl acetate (400 mL) and washed with water (2×100 mL), brine (100 mL), dried ($Na_2SO_4$) and filtered. The filtrate was evaporated under reduced pressure to afford 2.80 g (72%) of the desired product as a white solid. $^1$HNMR (400 MHz, DMSO) δ 9.99 (s, 1H, $D_2O$ exchangeable), 8.88 (d, J=1.5 Hz, 1H), 8.33 (d, J=1.5 Hz, 1H), 4.62 (s, 2H, $D_2O$ exchangeable), 2.91 (q, J=7.0 Hz, 2H), 1.22 (t, J=7.0 Hz, 3H); ESI-MS (m/z) 244, 246 [(MH)+, $Br^{79, 81}$].

Step-3: 5-(5-Bromo-6-ethylpyridin-3-yl)-1,3,4-oxadiazol-2(3H)-one: To a stirred and cooled (0° C.) solution of 5-bromo-6-ethylnicotinohydrazide (2.50 g, 10.24 mmol, 1.0 eq) and diisopropylethylamine (3.58 mL, 20.48 mmol, 2.0 eq) in DCM (20 mL) was added a solution of triphosgene (1.21 g, 4.10 mmol, 0.4 eq) in DCM (10 mL) over a period of 10 min. The resulting mixture was stirred for 1 h at the same temperature. The reaction mixture was then diluted with DCM (50 mL) and washed with water (50 mL), aqueous sodium bicarbonate (10%, 50 mL), brine (50 mL), dried ($Na_2SO_4$) and filtered. The filtrate was evaporated under vacuum to afford 1.60 g (58%) of the desired product as a white solid. $^1$HNMR (400 MHz, DMSO) δ 8.83 (d, J=1.5 Hz, 1H), 8.25 (d, J=1.5 Hz, 1H), 2.92 (q, J=7.0 Hz, 2H), 1.21 (t, J=7.0 Hz, 3H); ESI-MS (m/z) 270, 272 [(MH)+ $Br^{79, 81}$].

Step-4: Intermediate-1a: 5-(5-Bromo-6-ethylpyridin-3-yl)-3-methyl-1,3,4-oxadiazol-2(3H)-one: A mixture of 5-(5-Bromo-6-ethylpyridin-3-yl)-1,3,4-oxadiazol-2(3H)-one (1.20 g, 4.44 mmol, 1.0 eq), methyl iodide (0.55 mL, 8.89 mmol, 2.0 eq) and potassium carbonate (1.23 g, 8.89 mmol, 2.0 eq) in DMF (10 mL) was stirred at RT for 4 h. Water (50 mL) was added to the reaction mixture and the solid separated out was filtered. The residue was washed with water (50 mL)

and dried under vacuum to afford 800 mg (63%) the Intermediate-1a as a white solid. ¹HNMR (400 MHz, DMSO) δ 8.85 (d, J=1.5 Hz, 1H), 8.27 (d, J=1.5 Hz, 1H), 3.42 (s, 3H), 2.94 (q, J=7.0 Hz, 2H), 1.23 (t, J=7.0 Hz, 3H); ESI-MS (m/z) 284, 286 [(MH)⁺, Br[79,81]].

Step-5: Intermediate-1b: 5-(5-(5-Aminopyrazin-2-yl)-6-ethylpyridin-3-yl)-3-methyl-1,3,4-oxadiazol-2(3H)-one: To a solution of Intermediate-1a (1.0 g, 3.52 mmol, 1.0 eq) and 5-(trimethyl stannyl)-pyrazine-2-amine (1.36 g, 5.28 mmol, 2.0 eq; prepared from 2-Amino-5-bromopyrazine by following the procedure described in *Chem. Eur. J.* 2000, 6, 4132) in dioxane (10 mL) was added Pd(PPh₃)₄ (200 mg, 0.17 mmol, 0.05 eq). The resulting mixture was thoroughly deoxygenated by subjecting to vacuum/nitrogen cycle three times and the reaction mixture was stirred at 75° C. for 15 h under nitrogen atmosphere. The resulting mixture was cooled to RT and filtered through celite. The filtrate was concentrated under vacuum and the crude product was purified by flash column chromatography (silica gel, ethyl acetate-hexanes system as eluent) to afford 510 mg (48%) the Intermediate-1b as a white solid. ESI-MS (m/z) 299 (MH)⁺.

Step-6: Intermediate-1c: 5-(6-Ethyl-5-(4,4,5,5-tetramethyl-1,3,2-dioxaborolan-2-yl)pyridin-3-yl)-3-methyl-1,3,4-oxadiazol-2(3H)-one: To a nitrogen purged solution of Intermediate-1a (6.50 g, 22.8 mmol, 1.0 eq) in dioxane (35 mL), bis(pinacolatodiboron) (7.55 g, 29.7 mmol, 1.1 eq), potassium acetate (3.37 g, 34.3 mmol, 1.5 eq), palladium acetate (514 mg, 2.28 mmol, 0.1 eq) and 1,1'-bis(diphenylphosphino)ferrocene (1.27 g, 2.28 mmol, 0.1 eq) were sequentially added. The resulting mixture was stirred at 100° C. for 12 h in sealed tube. The reaction was then cooled to RT and filtered through celite. The filtrate was concentrated under vacuum and the crude product was purified by flash column chromatography (silica gel, ethyl acetate-hexanes system as eluent) to afford 6.0 g (80%) of the Intermediate-1c as a white solid. ¹HNMR (400 MHz, CDCl₃) δ 9.00 (d, J=2.5 Hz, 1H), 8.45 (d, J=2.5 Hz, 1H), 3.52 (s, 3H), 3.14 (q, J=7.0 Hz, 2H), 1.37 (s, 12H), 1.28 (t, J=7.0 Hz, 3H); ESI-MS (m/z) 332 (MH)⁺.

The below intermediates in Table-1 were prepared by following the similar procedure as described in Intermediate-1a or Intermediate-1b or Intermediate-1c by using corresponding starting materials.

TABLE 1

| Intermediate No: IUPAC name | Structure | ¹HNMR/ESI-MS |
|---|---|---|
| Intermediate-2a: 5-(5-Bromo-6-methylpyridin-3-yl)-3-methyl-1,3,4-oxadiazol-2(3H)-one | 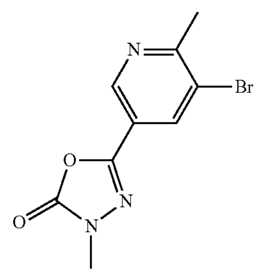 | ¹HNMR (400 MHz, DMSO) δ 8.82 (d, J = 1.5 Hz, 1H), 8.28 (d, J = 1.5 Hz, 1H), 3.42 (s, 3H), 2.65 (s, 3H); ESI-MS (m/z) 270, 272 [(MH)⁺ Br[79,81]]. |
| Intermediate-2b: 5-(5-(5-Aminopyrazin-2-yl)-6-methylpyridin-3-yl)-3-methyl-1,3,4-oxadiazol-2(3H)-one | 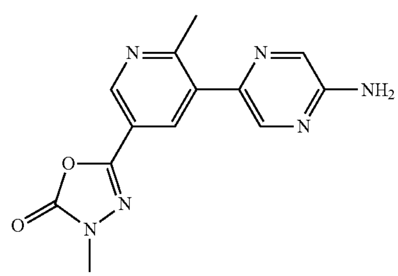 [SMILES: Cc1ncc(-c2nn(C)c(=O)o2)cc1-c1cnc(N)cn1] | ¹HNMR (400 MHz, CDCl₃) δ 8.97 (d, J = 1.5 Hz, 1H), 8.20 (d, J = 1.0 Hz, 1H), 8.14 (d, J = 1.5 Hz, 1H), 8.12 (d, J = 1.0 Hz, 1H), 4.81 (s, 2H, D₂O exchangeable), 3.53 (s, 3H), 2.71 (s, 3H); ESI-MS (m/z) 285 (MH)⁺ |
| Intermediate-3a: 5-(5-Bromo-6-cyclopropylpyridin-3-yl)-3-methyl-1,3,4-oxadiazol-2(3H)-one | 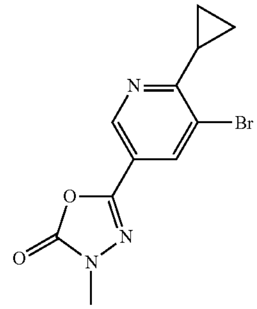 [SMILES: Cn1nc(-c2cnc(C3CC3)c(Br)c2)oc1=O] | ¹HNMR (400 MHz, DMSO) δ 8.75 (d, J = 2.0 Hz, 1H), 8.23 (d, J = 2.0 Hz, 1H), 3.34 (s, 3H), 2.55-2.50 (m, 1H), 1.14-1.10 (m, 2H), 1.06-1.03 (m, 2H); ESI-MS (m/z) 296, 298 [(MH)⁺ Br[79,81]] |

TABLE 1-continued

| Intermediate No: IUPAC name | Structure | $^1$HNMR/ESI-MS |
|---|---|---|
| Intermediate-3b: 5-(5-(5-Aminopyrazin-2-yl)-6-cyclopropylpyridin-3-yl)-3-methyl-1,3,4-oxadiazol-2(3H)-one | 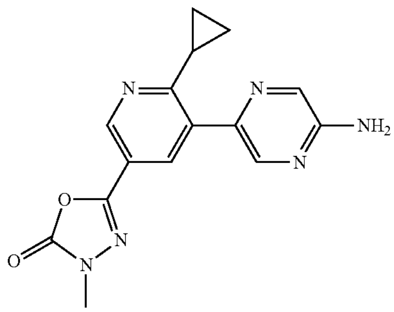 [SMILES: Cn1nc(-c2cnc(C3CC3)c(-c3cnc(N)cn3)c2)oc1=O] | $^1$HNMR (400 MHz, DMSO) δ 8.76 (d, J = 2.0 Hz, 1H), 8.23 (d, J = 1.5 Hz, 1H), 8.02 (d, J = 1.5 Hz, 1H), 7.99 (d, J = 2.0 Hz, 1H), 6.73 (s, D$_2$O exchangeable, 2H), 3.40 (s, 3H), 2.41-2.34 (m, 1H), 1.10-1.07 (m, 2H), 1.04-0.97 (m, 2H); ESI-MS (m/z) 311 (MH)$^+$ |
| Intermediate-3c: 5-(6-Cyclopropyl-5-(4,4,5,5-tetramethyl-1,3,2-dioxaborolan-2-yl)pyridin-3-yl)-3-methyl-1,3,4-oxadiazol-2(3H)-one | 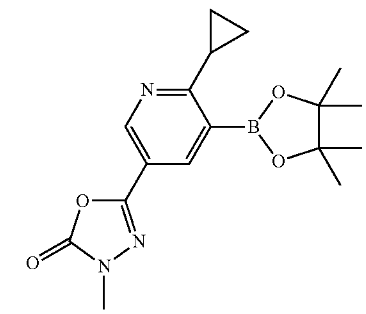 [SMILES: Cn1nc(-c2cnc(C3CC3)c(B3OC(C)(C)C(C)(C)O3)c2)oc1=O] | $^1$HNMR (400 MHz, CDCl$_3$) δ 8.89 (d, J = 2.0 Hz, 1H), 8.39 (d, J = 2.0 Hz, 1H), 3.51 (s, 3H), 2.96-2.92 (m, 1H), 1.38 (s, 12H), 1.22-1.19 (m, 2H), 1.09-1.04 (m, 2H); ESI-MS (m/z) 344 (MH)$^+$ |

Intermediate-4: 5-(5-Bromo-6-methoxypyridin-3-yl)-3-methyl-1,3,4-oxadiazol-2(3H)-one

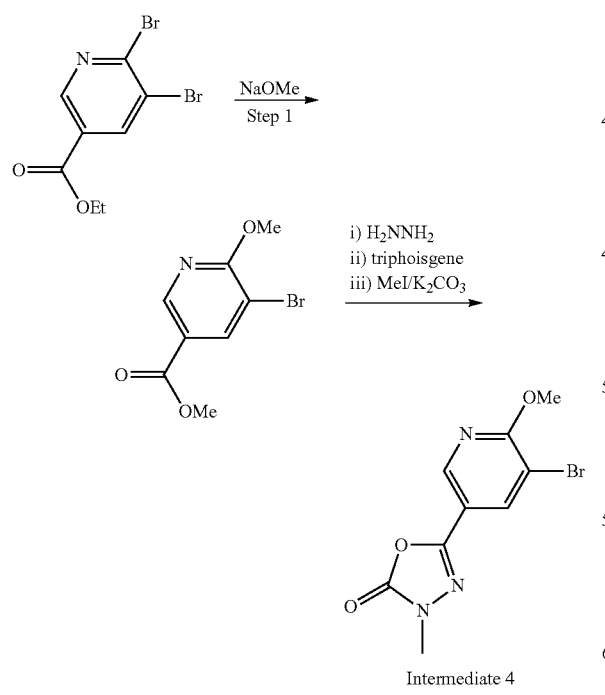

Intermediate 4

Step-1: Methyl 5-bromo-6-methoxynicotinate: To a solution of ethyl-5,6-dibromonicotinate (5.0 g, 16.2 mmol, 1.0 eq) in methanol (5 mL) was added sodium methoxide (2.18 g, 40.5 mmol, 2.5 eq) and the resulting mixture was heated in a sealed tube at 85° C. for 48 h. The reaction was cooled back down to RT and the solvent was evaporated under vacuum. The crude residue was taken into water (20 mL) and ethyl acetate (50 mL). The layers were separated and the aqueous layer was extracted with ethyl acetate (2×50 mL). The combined organic layers were washed with brine (50 mL), dried (Na$_2$SO$_4$) and filtered. The filtrate was evaporated and the resultant crude product was purified by flash column chromatography (silica gel, ethyl acetate:hexane system as eluent) to afford 1.55 g (39%) of the desired product as a white solid. $^1$HNMR (400 MHz, CDCl$_3$) δ 8.76 (d, J=2.0 Hz, 1H), 8.41 (d, J=2.0 Hz, 1H), 4.09 (s, 3H), 3.93 (s, 3H); ESI-MS (m/z) 246, 248 [(MH)$^+$, Br$^{79,81}$].

Step-2: 5-(5-Bromo-6-methoxypyridin-3-yl)-3-methyl-1,3,4-oxadiazol-2(3H)-one:

The title compound was prepared from Step-1 Intermediate by following the similar procedure sequentially as described in Step-2, Step-3 and Step-4 of Intermediate-1a. ESI-MS (m/z) 286, 288 [(MH)$^+$, Br$^{79,81}$].

Intermediate-5a: 5-(5-Bromo-6-(trifluoromethyl)pyridin-3-yl)-3-methyl-1,3,4-oxadiazol-2(3H)one and Intermediate-5b: 3-Methyl-5-(5-(4,4,5,5-tetramethyl-1,3,2-dioxaborolan-2-yl)-6-(trifluoromethyl)pyridin-3-yl)-1,3,4-oxadiazol-2(3H)-one

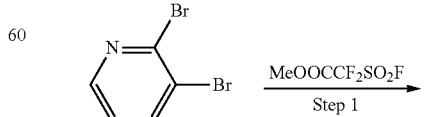

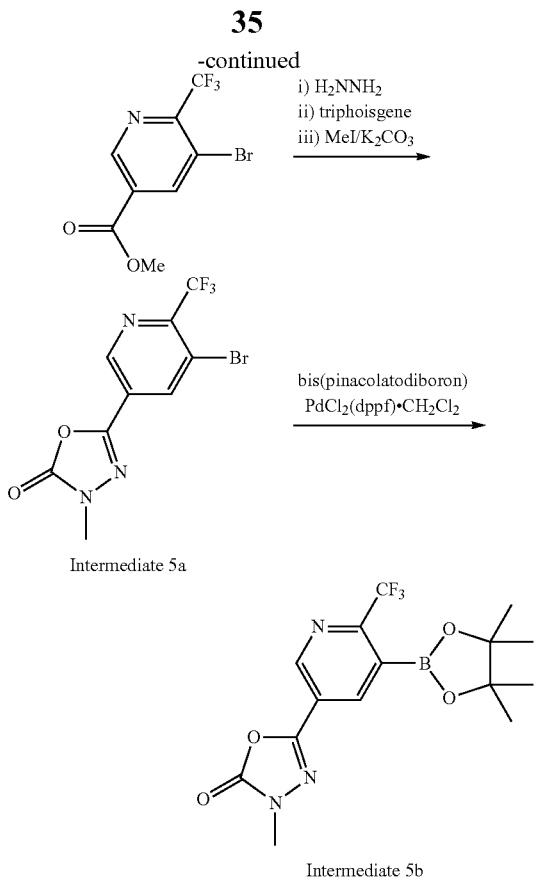

Intermediate 5a

Intermediate 5b

Step-1: Ethyl-5-bromo-6-(trifluoromethyl)nicotinate: A solution of ethyl 5,6-dibromonicotinate (prepared by following the procedure described in WO2011024004, 12 g, 38.8 mmol) was reacted with methyl 2,2-difluoro-2-(fluorosulfonyl)acetate (14.9 g, 78 mmol), copper iodide (9.62 g, 50.5 mmol) and HMPA (33.8 mL, 194 mmol), by following the similar procedure as described in WO2009141398 to afford 11 g (95%) the desired product as a white solid. $^1$HNMR (400 MHz, CDCl$_3$) δ 9.17 (d, J=1.5 Hz, 1H), 8.65 (d, J=1.5 Hz, 1H), 4.47 (q, J=7.0 Hz, 2H), 1.43 (t, J=7.0 Hz, 3H); ESI-MS (m/z) 298, 300 [(MH)$^+$ Br$^{79,81}$].

Intermediate-5a: The title compound was prepared from ethyl-5-bromo-6-(trifluoromethyl)nicotinate by following the similar procedure sequentially as described instep-1, step-2 and step-3 of Intermediate-1a. $^1$HNMR (400 MHz, DMSO) δ 9.08 (d, J=1.5 Hz, 1H), 8.66 (d, J=1.5 Hz, 1H), 3.45 (s, 1H); ESI-MS (m/z) 325, 327 [(MH)$^+$ Br$^{79,81}$]

Intermediate-5b: To a nitrogen purged solution of Intermediate-5a (4.0 g, 12.3 mmol 1.0 eq) in dioxane (35 mL), bis (pinacolatodiboron) (3.76 g, 14.81 mmol, 1.1 eq), potassium acetate (2.42 g, 24.6 mmol, 2.0 eq), and PdCl$_2$(dppf)-CH$_2$Cl$_2$ adduct (0.504 g, 0.617 mmol) were sequentially added. The resulting mixture was heated to 100° C. and further maintained for 12 h. The reaction mixture was cooled to RT and filtered through celite. The filtrate was concentrated under vacuum and the crude product was purified by flash column chromatography (silica gel, ethyl acetate-hexanes system as eluent) to afford 2.50 g (55%) of the desired compound as a white solid. $^1$HNMR (400 MHz, CDCl$_3$) δ 9.15 (d, J=1.5 Hz, 1H), 8.44 (d, J=1.5 Hz, 1H), 3.57 (s, 3H), 1.40 (s, 12H); ESI-MS (m/z) 372 (MH)$^+$.

Intermediate-6a: tert-Butyl-(3-bromo-5-(4-methyl-5-oxo-4,5-dihydro-1,3,4-oxadiazol-2-yl)pyridin-2-yl)(methyl)carbamate And Intermediate-6b: 5-(5-Bromo-6-(methylamino)pyridin-3-yl)-3-methyl-1,3,4-oxadiazol-2(3H)-one And Intermediate-6c: tert-Butyl (3-(5-aminopyrazin-2-yl)-5-(4-methyl-5-oxo-4,5-dihydro-1,3,4-oxadiazol-2-yl)pyridin-2-yl)(methyl)carbamate

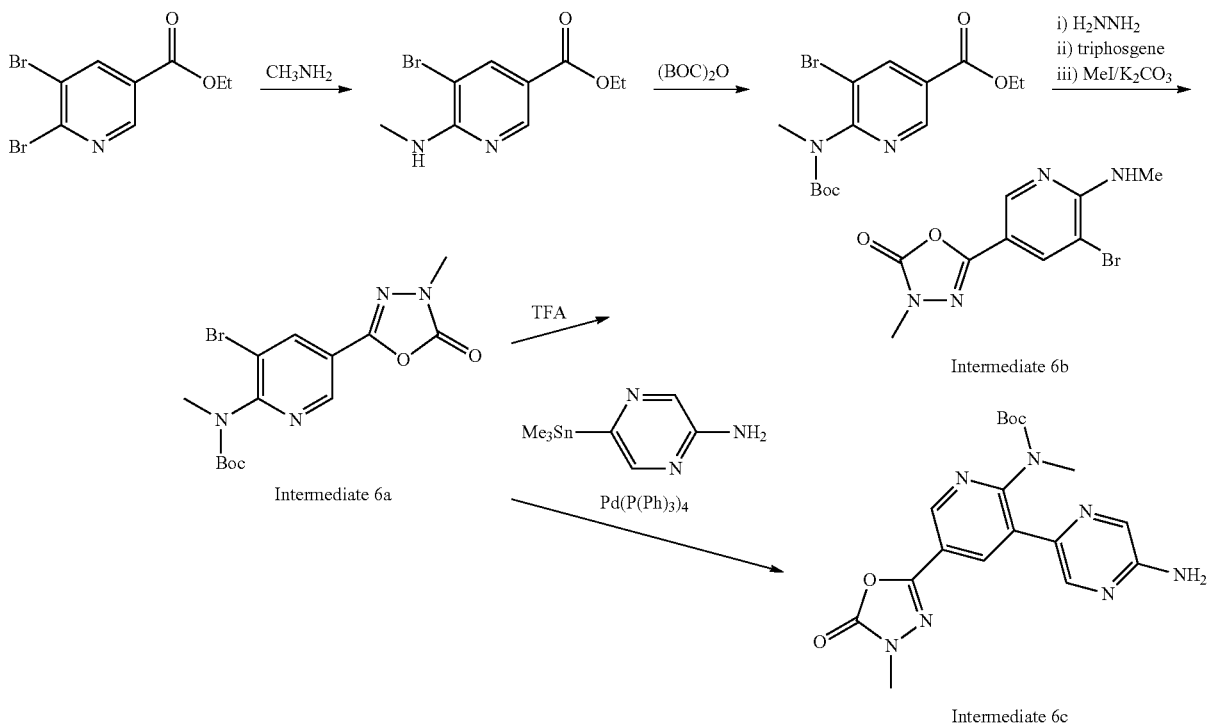

Step-1: Ethyl-5-bromo-6-(methylamino)-nicotinate: A solution of ethyl 5,6-dibromonicotinate (prepared by following the procedure described in WO2011024004, 5.0 g, 17.80 mmol) was reacted with methanamine (5 mL, 64.5 mmol 40% in water) in THF (20 ml) by following the procedure described in WO201000475. $^1$HNMR (400 MHz, DMSO) δ 8.58 (d, J=2.0 Hz, 1H), 8.05 (d, J=2.0 Hz, 1H), 7.21 (q, J=4.5 Hz, $D_2O$ exchangeable, 1H), 4.24 (q, J=7.0 Hz, 2H), 2.91 (d, J=4.5 Hz, 3H), 1.30 (t, J=7.0 Hz, 3H); GC-MS (m/z) 258, 260 [(M)$^+$ Br$^{79,81}$].

Step-2: Ethyl-5-bromo-6-((tert-butoxycarbonyl)(methyl)amino)nicotinate: To a solution of ethyl 5-bromo-6-(methylamino)nicotinate (4.50 g, 17.37 mmol) and triethylamine (9.68 mL, 69.5 mmol) in acetonitrile (50 mL) was added Boc$_2$O (16.1 ml, 69.5 mmol) followed by DMAP (5 mg, 0.347 mmol). The resulting mixture was heated to 85° C. and maintained for 48 h. Reaction mixture was then cooled to RT and the solvent was evaporated under vacuum. The residue was taken in ethyl acetate (200 mL) and washed with water (2×50 mL), brine (50 mL), dried (Na$_2$SO$_4$) and filtered. The filtrate was concentrated under vacuum to afford 4.0 g (64%) of title compound as oily mass. $^1$HNMR (400 MHz, CDCl$_3$) δ 9.01 (d, J=2.0 Hz, 1H), 8.51 (d, J=2.0 Hz, 1H), 4.43 (q, J=7.0 Hz, 2H), 3.27 (s, 1H), 1.43 (t, J=7.0 Hz, 3H), 1.43 (s, 9H); ESI-MS (m/z) 303, 305 [(M-55)$^+$ Br$^{79,81}$].

Intermediate-6a: The title compound was prepared from Step-2 intermediate by following the similar procedure sequentially as described in step-2, step-3 and step-4 of Intermediate-1a. $^1$HNMR (400 MHz, DMSO) δ 8.85 (d, J=2.0 Hz, 1H), 8.47 (d, J=2.0 Hz, 1H), 3.41 (s, 3H), 3.14 (s, 3H), 1.36 (s, 9H); ESI-MS (m/z) 329, 331 [(M-55)$^+$ Br$^{79,81}$].

Intermediate-6b: To a 0° C. cooled solution of Intermediate-6a (1.0 g, 2.60 mmol) in DCM (10 mL) was added trifluoroacetic acid (1.0 mL, 12.98 mmol) and then stirred at RT for 16 h. The excess of trifluoroacetic acid was evaporated under vacuum and the resulting residue was triturated with hexane and diethyl ether to afford 500 mg (68%) of desired compound as a white solid. $^1$HNMR (400 MHz, DMSO) δ 8.41 (d, J=2.0 Hz, 1H), 7.97 (d, J=2.0 Hz, 1H), 7.16 (s, 1H), 3.35 (s, 3H), 2.90 (s, 3H); ESI-MS (m/z) 285, 287 [(MH)$^+$ Br$^{79,81}$].

Intermediate-6c: To a nitrogen purged solution of Intermediate-6a (1.0 g, 2.60 mmol, 1.0 eq) in dioxane (10 mL) in a sealed tube 5-(trimethyl stannyl)-pyrazine-2-amine (1.34 g, 5.19 mmol, 2.0 eq; prepared from 2-amino-5-bromopyrazine by following the procedure described in Chem. Eur. J. 2000, 6, 4132) and Pd(PPh$_3$)$_4$ (210 mg, 0.18 mmol, 0.05 eq) were sequentially added. The resulting mixture was thoroughly deoxygenated by purging nitrogen gas for 15 min and the reaction mixture was heated to 120° C. and maintained for 48 h. The resulting mixture was then cooled to RT and filtered through celite. The filtrate was concentrated under vacuum and the crude product was purified by flash column chromatography (silica gel, ethyl acetate-hexanes system as eluent) to afford 510 mg (50%) the title compound as a white solid. $^1$HNMR (400 MHz, CDCl$_3$) δ 8.88 (d, J=2.0 Hz, 1H), 8.41 (d, J=2.0 Hz, 1H), 8.27 (d, J=2.0 Hz, 1H), 8.10 (d, J=2.0 Hz, 1H), 5.31 (s, 2H), 3.54 (s, 3H), 3.40 (s, 3H), 1.51 (s, 9H); ESI-MS (m/z) 400 (MH)$^+$ Intermediate-7: 5-(5-(4-Aminophenyl)-6-ethylpyridin-3-yl)-3-methyl-1,3,4-oxadiazol-2(3H)one

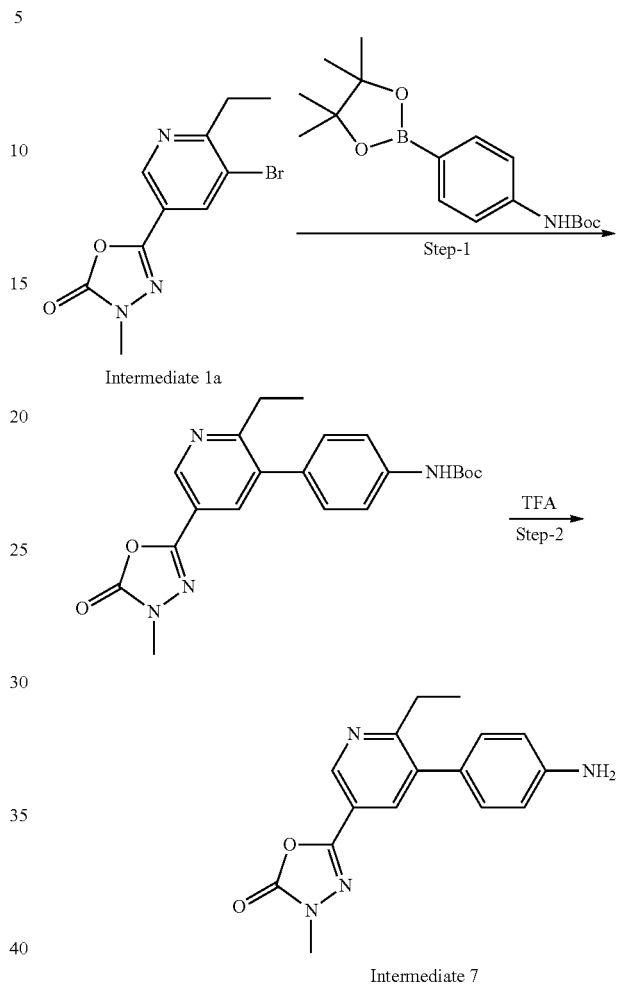

Step-1: tert-Butyl (4-(2-ethyl-5-(4-methyl-5-oxo-4,5-dihydro-1,3,4-oxadiazol-2-yl)pyridin-3-yl)phenyl)carbamate: To a solution of Intermediate-1a (2.30 g, 8.10 mmol, 1.0 eq) and tert-butyl (4-(4,4,5,5-tetramethyl-1,3,2-dioxaborolan-2-yl)phenyl)carbamate (2.58 g, 8.10 mmol, 1.0 eq; prepared from 4-bromoaniline by following the procedure described in organic and biomolecular chemistry, 2010, 8 (15), 3457) in dioxane (25 mL) was added Pd(PPh$_3$)$_2$Cl$_2$ (284 mg, 0.40 mmol). The resulting mixture was thoroughly deoxygenated by subjecting to vacuum/nitrogen cycle three times and the reaction mixture was heated to 75° C. and further maintained for 15 h under nitrogen atmosphere. The resulting mixture was cooled to RT and filtered through celite. The filtrate was concentrated under vacuum and the crude product was purified by flash column chromatography (silica gel, ethyl acetate-hexanes system as eluent) to afford 2.80 g (78%) of the desired compound as a white solid. $^1$HNMR (400 MHz, CDCl$_3$) δ 8.96 (s, 1H), 7.89 (s, 1H), 7.48 (d, J=8.0 Hz, 2H), 7.26 (d, J=8.0 Hz, 2H), 6.75 (s, 1H), 3.51 (s, 3H), 2.84 (q, J=7.0 Hz, 2H), 1.58 (s, 9H), 1.23 (t, J=7.0 Hz, 3H); ESI-MS (m/z) 397 (MH)$^+$ Step-2: 5-(5-(4-Aminophenyl)-6-ethylpyridin-3-yl)-3-methyl-1,3,4-oxadiazol-2(3H)-one: To a 0° C. cooled solution of above Step-1 intermediate (2.50 g, 6.31 mmol) in DCM (15 mL) was added trifluoroacetic acid (15 mL) in drop wise manner and the resulting mixture was stirred at RT for 2 h. The solvent was evaporated under vacuum. Water (50 mL) was added to the above obtained residue and basified with saturated aqueous sodium bicarbonate solution. The resulting mixture was extracted with ethyl acetate (3×50 mL) and the combined organic layers were washed with brine (50 mL), dried (Na$_2$SO$_4$) and filtered. The filtrated was evaporated under vacuum to afford 1.35 g (70%) of the desired product as a solid. $^1$HNMR (400 MHz, CDCl$_3$) δ 8.95 (d, J=2.5 Hz, 1H), 7.90 (d, J=2.5 Hz, 1H), 7.13 (d, J=8.45 Hz, 2H), 6.77 (d, J=8.5 Hz, 2H), 3.81 (s, 2H), 3.52 (s, 3H), 2.88 (q, J=7.5 Hz, 2H), 1.24 (t, J=7.5 Hz, 3H); ESI-MS (m/z) 297 (MH)$^+$.

Intermediate-8: 5-(5-Bromo-4-methylpyridin-2-yl)-3-methyl-1,3,4-oxadiazol-2(3H)-one

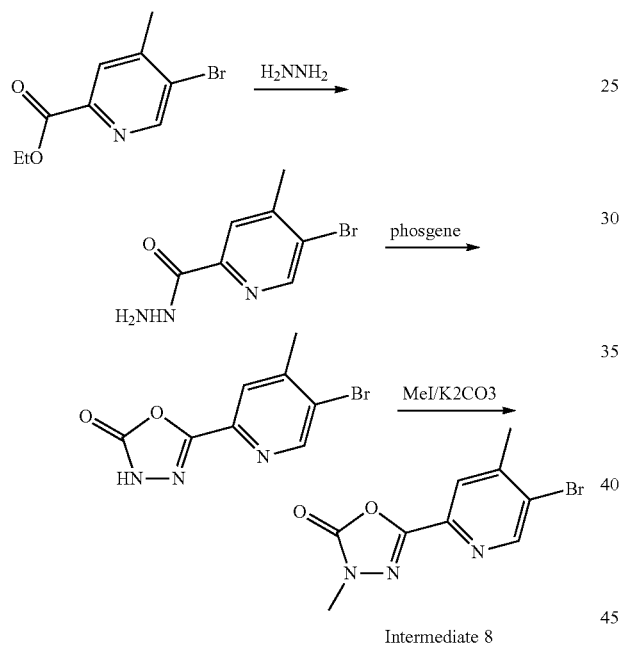

Intermediate 8

The title compound was prepared by following the similar procedure sequentially as described in step-2, step-3, and step-4 of Intermediate-1 using ethyl 5-bromo-4-methylpicolinate (prepared by following the similar procedure as described in US2011212998). $^1$HNMR (400 MHz, DMSO) δ 8.79 (s, 1H), 7.93 (s, 1H), 3.34 (s, 3H), 2.45 (s, 3H); ESI-MS (m/z) 270, 272 [(MH)$^+$ Br$^{79,81}$].

Intermediate-9: 5-(6-Chloro-4-ethoxypyridin-2-yl)-3-methyl-1,3,4-oxadiazol-2(3H)-one Intermediate 9

Step-1: Ethyl 4-ethoxypicolinate: A solution of 4-chloropicolinic acid (1.0 g, 6.35 mmol) and sulphuric acid (0.2 mL, 3.75 mmol) in ethanol (10 mL) was heated to 85° C. and maintained for 16 h. Reaction mixture was cooled to RT and the solvent was evaporated under vacuum. The residue was taken into ethyl acetate (20 mL) and basified with aqueous saturated sodium bicarbonate (pH 10, 20 mL). The layers were separated and the organic layer was washed with brine (15 mL), dried (Na$_2$SO$_4$) and filtered. The filtrate was concentrated under vacuum to afford 1.0 g (69%) the title compound as brown oily mass. $^1$HNMR (400 MHz, CDCl$_3$) δ 8.54 (d, J=5.5 Hz, 1H), 7.65 (d, J=2.5 Hz, 1H), 6.94 (dd, J=5.5 & 2.5 Hz, 1H), 4.47 (q, J=7.0 Hz, 2H), 4.15 (q, J=7.0 Hz, 2H), 1.47-1.42 (m, 6H); GC-MS (m/z) 185 (M)$^+$.

Step-2: 4-Ethoxypicolinohydrazide: To a 0° C. cooled solution of ethyl 4-ethoxypicolinate (5.0 g, 25.6 mmol) in ethanol (20 mL) was added hydrazine hydrate (6.0 g, 120 mmol) drop-wise. After stirring for 2 h at RT, the separated out solid was filtered. The solid residue was washed with water (50 mL) and dried to yield 5.80 g (99%) of the title compound as white solid. $^1$HNMR (400 MHz, DMSO) δ 9.82 (brs, 1H, D$_2$O exchangeable), 8.40 (d, J=5.5 Hz, 1H), 7.46 (d, J=2.5 Hz, 1H), 7.09 (dd, J=5.5 & 2.5 Hz, 1H), 4.54 (brs, 2H, D$_2$O exchangeable), 4.11 (q, J=7.0 Hz, 2H), 1.38 (t, J=7.0 Hz, 3H); GC-MS (m/z) 181 (M)$^+$.

Step-3: 5-(4-Ethoxypyridin-2-yl)-3-methyl-1,3,4-oxadiazol-2(3H)-one: The title compound was prepared from 4-ethoxypicolinohydrazide by following the similar procedure sequentially as described in step-3 and step-4 of Intermediate-1. ¹HNMR (400 MHz, DMSO) δ 8.49 (d, J=5.5 Hz, 1H), 7.33 (d, J=2.5 Hz, 1H), 7.13 (dd, J=5.5 & 2.5 Hz, 1H), 4.19 (q, J=7.0 Hz, 2H), 3.42 (s, 3H), 1.35 (t, J=7.0 Hz, 3H); GC-MS (m/z) 221 (M)⁺.

Step-4: 4-Ethoxy-2-(4-methyl-5-oxo-4,5-dihydro-1,3,4-oxadiazol-2-yl)pyridine1-oxide: A solution of 5-(4-ethoxypyridin-2-yl)-3-methyl-1,3,4-oxadiazol-2(3H)-one (200 mg, 0.90 mmol) and mCPBA (156 mg, 0.90 mmol) in DCM (5 mL) was stirred at RT for 48 h. Ice water (10 mL) was added to the above reaction mixture, basified with aqueous saturated sodium bicarbonate solution (5 mL) and extracted with ethylacetate (3×10 mL). The combined organic layers were washed with brine (10 mL), dried (Na$_2$SO$_4$) and filtered. The filtrate was concentrated under vacuum to afford 160 mg (75%) of title compound as a white solid. ¹HNMR (400 MHz, DMSO) δ 8.29 (d, J=5.5 Hz, 1H), 7.32 (d, J=2.5 Hz, 1H), 7.13 (dd, J=5.5 & 2.5 Hz, 1H), 4.16 (q, J=7.0 Hz, 2H), 3.42 (s, 3H), 1.32 (t, J=7.0 Hz, 3H); GC-MS (m/z) 237 (M)⁺.

Step-5: 5-(6-Chloro-4-ethoxypyridin-2-yl)-3-methyl-1,3,4-oxadiazol-2(3H)-one: A mixture of 4-ethoxy-2-(4-methyl-5-oxo-4,5-dihydro-1,3,4-oxadiazol-2-yl)pyridine-1-oxide (1.0 g, 4.22 mmol) and phosphorous oxychloride (8 mL) was heated to 80° C. and maintained for 4 h. The excess of phosphorous oxychloride was distilled under vacuum.

The resulting residue was taken in ice water, basified with aqueous saturated sodium bicarbonate solution (10 mL) and extracted with ethylacetate (3×20 mL). The combined organic layers were dried (Na$_2$SO$_4$) and filtered. The filtrate was concentrated under vacuum to afford 200 mg (19%) of the Intermediate 9 as a white solid. ¹HNMR (400 MHz, DMSO) δ 7.33 (d, J=2.0 Hz, 1H), 7.30 (d, J=2.0 Hz, 1H), 4.24 (q, J=7.0 Hz, 2H), 3.43 (s, 3H), 1.34 (t, J=7.0 Hz, 3H); GC-MS (m/z) 255, 257 [(M)⁺, Cl³⁵,³⁷].

Intermediate-10a: 5-(4-Chloropyridin-2-yl)-3-methyl-1,3,4-oxadiazol-2(3H)-one And Intermediate-10b: 5-(4,6-Dichloropyridin-2-yl)-3-methyl-1,3,4-oxadiazol-2(3H)-one

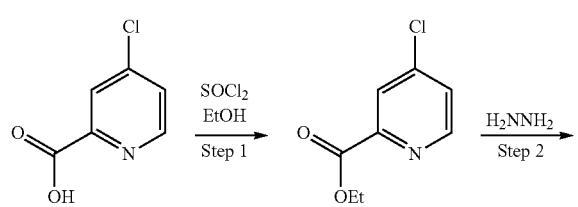

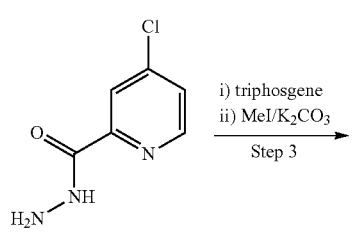

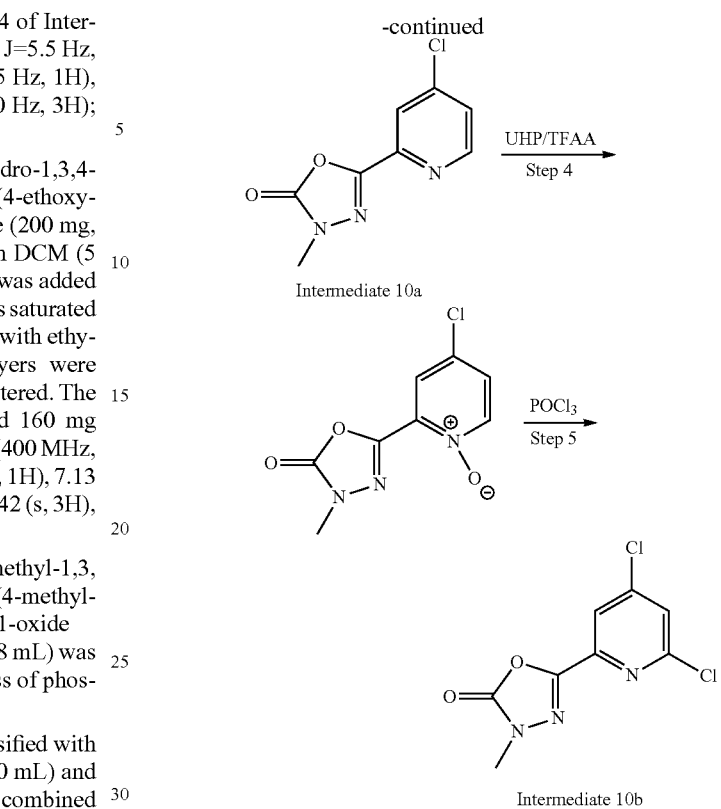

Intermediate 10a

Intermediate 10b

UHP = urea hydrogen peroxide

Step-1: Ethyl-4-chloroypicolinate: A mixture of 4-chloropicolinic acid (20 g, 127 mmol) and thionyl chloride (200 mL) was heated to 100° C. and maintained for 6 h. The reaction was cooled to RT, and the excess of thionyl chloride was removed under vacuum. To the above obtained residue was then added ethanol (200 mL) at 0° C. drop-wise and the resulting mixture was stirred at RT for 20 h. The solvent was evaporated under vacuum and the residue was taken in ethyl acetate (1000 mL), washed with water (2×500 mL), saturated sodium bicarbonate solution (2×500 mL), brine (500 mL), dried (Na$_2$SO$_4$) and filtered. The filtrate was evaporated to yield 21.0 g (89%) the desired product as a semi solid. ¹HNMR (400 MHz, DMSO) δ 8.66 (d, J=5.0 Hz, 1H), 8.13 (d, J=2.0 Hz, 1H), 7.49 (dd, J=5.0 &2.0 Hz 1H), 4.47 (q, J=7.0 Hz, 2H), 1.46 (t, J=7.0 Hz, 3H); GC-MS (m/z) 185, 187 [(M)⁺, Cl³⁵,³⁷].

Step-2: 4-Chloropicolinohydrazide: The title compound was prepared from ethyl-4-chloroypicolinate by following the similar procedure as described in step-2 of Intermediate-9. ¹HNMR (400 MHz, DMSO) δ 10.05 (s, 1H, D$_2$O exchangeable), 8.58 (d, J=5.0 Hz, 1H), 7.96 (d, J=2.0 Hz, 1H), 7.70 (dd, J=5.0 &2.0 Hz, 1H), 4.62 (s, 2H, D$_2$O exchangeable); GC-MS (m/z) 171, 173 [(M)⁺, Cl³⁵,³⁷].

Intermediate-10a: The title compound was prepared from 4-ethoxypicolinohydrazide by following the similar procedure sequentially as described instep-3 and step-4 of Intermediate-1. ¹HNMR (400 MHz, DMSO) δ 8.69 (d, J=5.0 Hz, 1H), 7.94 (d, J=2.0 Hz, 1H), 7.74 (dd, J=5.0 & 2.0 Hz, 1H), 3.44 (s, 3H); GC-MS (m/z) 211, 213 [(M)⁺, Cl³⁵,³⁷].

Intermediate-10b: 4-Chloro-2-(4-methyl-5-oxo-4,5-dihydro-1,3,4-oxadiazol-2-yl)pyridine 1-oxide To a 0° C. cooled solution of Intermediate-10a (3.50 g, 16.5 mmol) in DCM (30 mL) was added urea hydrogen peroxide (UHP) (3.11 g, 33.1 mmol) followed by drop-wise addition of trifluoroacetic anhydride (4.67 ml, 33.1 mmol) and the resulting mixture was stirred at RT for 16 h. The reaction mixture was diluted with DCM (50 mL), basified with solid potassium carbonate and the slurry was filtered. The filtrate was evaporated to yield 3.50 g (93%) of the desired product as a white solid. $^1$HNMR (400 MHz, DMSO) δ 8.42 (d, J=7.0 Hz, 1H), 7.94 (d, J=3.0 Hz, 1H), 7.74 (dd, J=7.0 & 3.0 Hz, 1H), 3.44 (s, 3H); GC-MS (m/z) 277, 279 [(M)$^+$, Cl$^{35,37}$]. Further it was reacted with POCl$_3$ by following the similar procedure as described in Step-5 of Intermediate-9. $^1$HNMR (400 MHz, DMSO) δ 7.77 (d, J=1.5 Hz, 1H), 7.94 (d, J=1.5 Hz, 1H), 3.57 (s, 3H); GC-MS (m/z) 246, 248 [(M)$^+$, Cl$^{35, 37}$].

Intermediate-11: 5-(5-Bromopyridin-3-yl)-3-methyl-1,3,4-oxadiazol-2(3H)-one

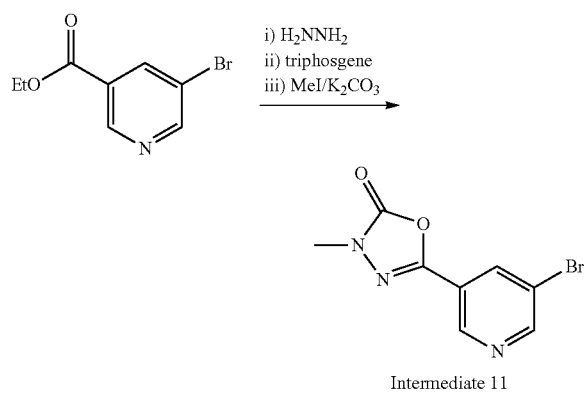

Intermediate 11

Step-1: 5-(5-Bromopyridin-3-yl)-3-methyl-1,3,4-oxadiazol-2(3H)-one: The title compound was prepared by following the similar procedure sequentially as described in step-2, step-3 and step-4 of Intermediate-1a. $^1$HNMR (400 MHz, DMSO) δ 8.94 (d, J=2.0 Hz, 1H), 8.90 (d, J=2.0 Hz, 1H), 8.35 (dd, J=2.0 & 2.0 Hz, 1H), 3.43 (s, 3H); ESI-MS (m/z) 256, 258 [(MH)$^+$ Br$^{79,81}$].

Intermediate-12: 5-(5-Bromo-4-ethylpyridin-3-yl)-3-methyl-1,3,4-oxadiazol-2(3H)-one

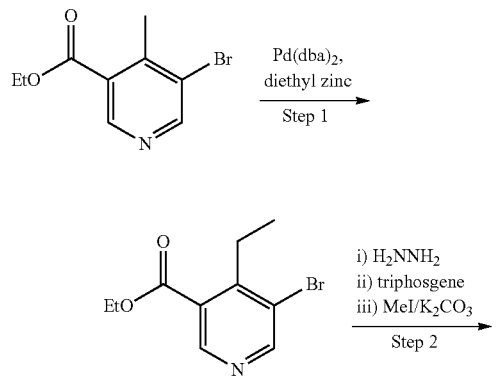

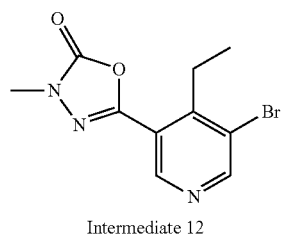

Intermediate 12

Step-1: Ethyl 5-bromo-4-ethylnicotinate: To a nitrogen purged and stirred solution of ethyl 5-bromo-4-iodonicotinate (2.50 g, 7.02 mmol, prepared by following the procedure described in J. Am. Che. Soc., 2008, 130 (2), 472-480) in THF (10 mL) was added Pd(dba)$_2$ (202 mg, 0.351 mmol). The resulting mixture was cooled to 0° C. and diethylzinc (1M in THF, 10.54 mL, 10.54 mmol) was added drop-wise for 15 min. The reaction was warmed to RT and stirred for 10 min. Reaction was cooled to 0° C. and quenched with 0.5 mL cold methanol. The reaction mixture was diluted with ethyl acetate (20 mL) and filtered through celite. The filtrate was evaporated and the crude product was purified by flash column chromatography (silica gel, EtOAc-hexane as eluent) to afford 0.95 g (52%) of the desired product along with de-iodinated compound. $^1$HNMR (400 MHz, CDCl$_3$) δ 8.89 (s, 1H), 8.78 (s, 1H), 4.43 (q, J=7.0 Hz, 2H), 3.11 (q, J=7.5 Hz, 2H), 1.42 (t, J=7.0 Hz, 3H), 1.25 (t, J=7.5 Hz, 3H); GC-MS (m/z) 257, 259 [(MH)$^+$ Br$^{79,81}$].

Step-2: 5-(5-Bromo-4-ethylpyridin-3-yl)-3-methyl-1,3,4-oxadiazol-2(3H)-one: The title compound was prepared from ethyl 5-bromo-4-ethylnicotinate by following the similar procedure sequentially as described in step-2, step-3, and step-4 of Intermediate-1a. $^1$HNMR (400 MHz, DMSO-d$_6$) δ 8.87 (s, 1H), 8.78 (s, 1H), 3.44 (s, 3H), 3.06 (q, J=7.5 Hz, 2H), 1.18 (t, J=7.5 Hz, 3H); ESI-MS (m/z) 284, 286 [(MH)$^+$, Br$^{79,81}$].

Intermediate-13: 5-(2-Chloro-3-methylpyridin-4-yl)-3-methyl-1,3,4-oxadiazol-2(3H)-one:

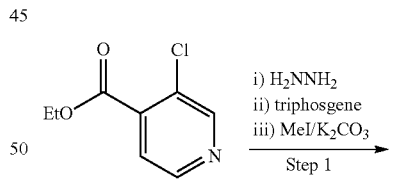

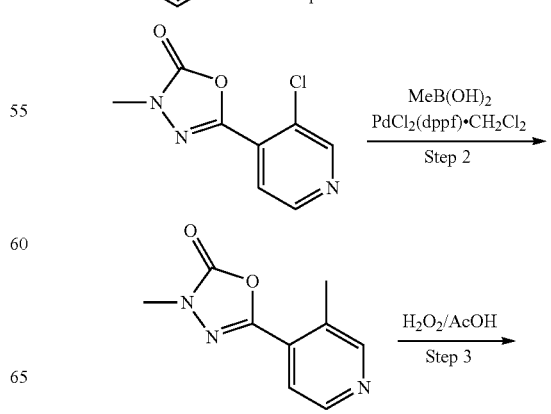

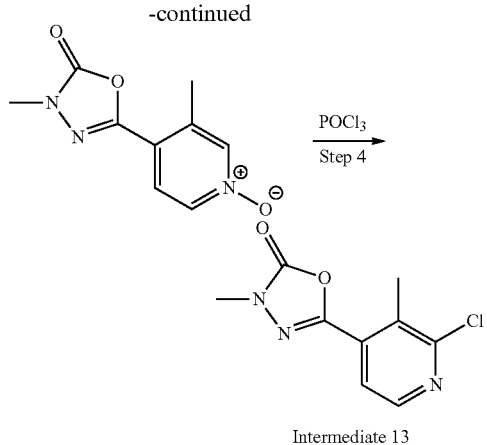

Intermediate 13

Step-1: 5-(3-Chloropyridin-4-yl)-3-methyl-1,3,4-oxadiazol-2(3H)-one: The title compound was prepared from ethyl-3-chloroisonicotinate (6.0 g, 32.3 mmol, prepared by following the procedure described in WO2008024724) by following the similar procedure sequentially as described in step-2, step-3 and step-4 of Intermediate-1 (from). $^1$HNMR (400 MHz, CDCl$_3$) δ 8.76 (s, 1H), 8.63 (d, J=5.0 Hz, 1H), 7.69 (d, J=5.0 Hz, 1H), 3.58 (s, 3H); GC-MS (m/z) 111, 113 [M$^+$, Cl$^{35,37}$].

Step-2: 3-Methyl-5-(3-methylpyridin-4-yl)-1,3,4-oxadiazol-2(3H)-one: To a stirred solution of step-1 intermediate (1.0 g, 4.73 mmol) in dioxane (30 mL), methylboronic acid (368 mg, 6.14 mmol), potassium carbonate (1.96 g, 14.18 mmol) and Pd(PPh$_3$)$_4$ (273 mg, 0.23 mmol) were sequentially added. The resulting mixture was thoroughly deoxygenated by subjecting to vacuum/nitrogen cycle three times and the reaction mixture was heated to 120° C. and maintained for 16 h under nitrogen atmosphere. The reaction mixture was cooled to RT and filtered through celite. The filtrate was concentrated under vacuum and the crude product was purified by flash column chromatography (10% Ethyl acetate in hexanes) to afford 0.86 g (95%) of the title compound as white solid. $^1$HNMR (400 MHz, CDCl$_3$) δ 8.60 (m, 2H), 7.64 (d, J=5.0 Hz, 1H), 3.56 (s, 3H), 2.60 (s, 3H).

Step-3: 3-Methyl-4-(4-methyl-5-oxo-4,5-dihydro-1,3,4-oxadiazol-2-yl)pyridine-1-oxide: To a stirred solution of step-2 intermediate (1.0 g, 5.23 mmol) in acetic acid (30 mL) was added hydrogen peroxide (0.321 mL, 10.46 mmol) dropwise at RT and the reaction was heated to 80° C. and maintained for 12 h. The resulting mixture was cooled to RT and basified with solid potassium carbonate. The resulting slurry was diluted with dichloromethane (50 mL) and filtered. The filtrate was concentrated under vacuum to afford 800 mg (88%) of title compound as white solid. $^1$HNMR (400 MHz, DMSO-d$_6$) δ 8.34 (s, 1H), 8.19 (d, J=5.0 Hz, 1H), 7.67 (d, J=5.0 Hz, 1H), 3.43 (s, 3H), 2.45 (s, 3H).

Step-4: 5-(2-Chloro-3-methylpyridin-4-yl)-3-methyl-1,3,4-oxadiazol-2(3H)-one: A mixture of step-3 intermediate (0.800 g, 3.86 mmol) and POCl$_3$ (15 mL, 161 mmol) was heated at 100° C. for 1 h. Excess of POCl$_3$ was distilled under reduced pressure and the crude product was purified by flash column chromatography (silica gel, 4% diethyl ether in hexanes) to afford 270 mg (25%) of the desired compound as a white solid. $^1$HNMR (400 MHz, DMSO-d$_6$) δ 8.38 (d, J=5.0 Hz, 1H), 7.60 (d, J=5.0 Hz, 1H), 3.57 (s, 3H), 2.72 (s, 3H) ESI-MS (m/z) 226 (MH)$^+$ Intermediate-14a: 5-(2-Chloro-3-ethylpyridin-4-yl)-3-methyl-1,3,4-oxadiazol-2(3H)-one And Intermediate-14b: 5-(2-Chloro-5-ethylpyridin-4-yl)-3-methyl-1,3,4-oxadiazol-2(3H)-one

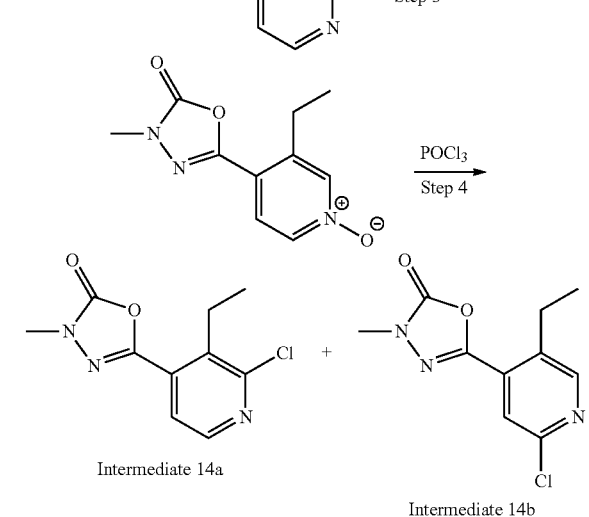

Intermediate 14a    Intermediate 14b

Step-1: Ethyl-3-ethylisonicotinate: To a mixture of ethyl 3-chloroisonicotinate (6.0 g, 32.3 mmol, prepared by following the procedure described in WO2008024724), and PdCl$_2$(dppf)·CH$_2$Cl$_2$ adduct (1.05 g, 1.29 mmol) in dioxane (40 mL) at RT was added drop-wise diethyl zinc (1M in THF, 32.3 mL, 32.3 mmol). The resulting mixture was thoroughly deoxygenated by subjecting to vacuum/nitrogen cycle three times and the reaction mixture was heated to 70° C. and maintained for 4 h under nitrogen atmosphere. The reaction mixture was cooled to RT and then quenched with methanol (1 mL). Water (10 mL) was added to the above mixture followed by ethyl acetate (50 mL). The layers were separated and aqueous layer was extracted with ethyl acetate (3×75 mL). The combined organic layers were washed with 1N hydrochloric acid (50 mL), water (50 mL), brine (20 mL) dried (Na$_2$SO$_4$) and filtered. The filtrate was concentrated under vacuum. The crude product was purified by flash column chromatography to afford 2.30 g (40%) of the title compound as colorless oil. $^{1}$HNMR (400 MHz, CDCl$_{3}$) δ 8.58 (s, 1H), 8.55 (d, J=5.0 Hz, 1H), 7.64 (d, J=5.0 Hz, 1H), 4.42 (q, J=7.5 Hz, 2H), 2.97 (q, J=7.0 Hz, 2H), 1.41 (t, J=7.5 Hz, 3H) 1.26 (t, J=7.0 Hz, 3H); GC-MS (m/z) 179 (M)$^{+}$.

Step-2: 5-(3-Ethylpyridin-4-yl)-3-methyl-1,3,4-oxadiazol-2(3H)-one: The title compound was prepared from ethyl-3-ethylisonicotinate by following the similar procedure sequentially as described in step-2, step-3 and step-4 of Intermediate-1a. $^{1}$HNMR (400 MHz, CDCl$_{3}$) δ 8.63 (s, 1H), 8.59 (d, J=5.0 Hz, 1H), 7.64 (d, J=5.0 Hz, 1H), 3.56 (s, 3H), 3.03 (q, J=7.5 Hz, 2H), 1.28 (t, J=7.5 Hz, 3H); GC-MS (m/z) 205 (M)$^{+}$ Step-3: 3-Ethyl-4-(4-methyl-5-oxo-4,5-dihydro-1,3,4-oxadiazol-2-yl)pyridine-1-oxide: To a stirred solution of step-2 intermediate (3.50 g, 17.1 mmol) in acetic acid (30 mL) was added hydrogen peroxide (0.62 mL, 20.4 mmol) drop-wise at RT and the resulting mixture was heated to 80° C. and maintained for 12 h. The reaction was cooled to RT and basified with solid potassium carbonate. The resulting slurry was diluted with DCM (50 mL) and filtered. The filtrate was concentrated under vacuum to afford 2.70 g (70%) of the title compound as white solid. GC-MS (m/z) 221 (M)$^{+}$.

Step-4: 5-(2-Chloro-3-ethylpyridin-4-yl)-3-methyl-1,3,4-oxadiazol-2(3H)-one and 5-(2-Chloro-5-ethylpyridin-4-yl)-3-methyl-1,3,4-oxadiazol-2(3H)-one: A mixture of 3-ethyl-4-(4-methyl-5-oxo-4,5-dihydro-1,3,4-oxadiazol-2-yl) pyridine-1-oxide (330 mg, 1.50 mmol) and phosphorous oxychloride (2 mL, 21.4 mmol) was heated to 95° C. and maintained for 8 h. Excess of POCl$_{3}$ was removed by distillation under reduced pressure and the crude product was purified by flash column chromatography to afford 80 mg (23%) of the Intermediate-14a as colorless oil along with 80 mg (23%) of 5-(2-chloro-5-ethylpyridin-4-yl)-3-methyl-1,3,4-oxadiazol-2(3H)-one (Intermediate-14b).

Intermediate-14a: $^{1}$HNMR (400 MHz, CDCl$_{3}$) δ 8.57 (d, J=5.0 Hz, 1H), 7.64 (d, J=5.0 Hz, 1H), 3.57 (s, 3H), 2.17 (q, J=7.5 Hz, 2H), 1.25 (t, J=7.5 Hz, 3H); GC-MS 239, 141 [M$^{+}$, Cl$^{35, 37}$]

Intermediate-14b: $^{1}$HNMR (400 MHz, CDCl$_{3}$) δ 8.39 (s, 1H), 7.69 (s, 1H), 3.55 (s, 3H), 3.01 (q, J=7.5 Hz, 2H), 1.28 (t, J=7.5 Hz, 3H); GC-MS 239, 141 [M$^{+}$, Cl$^{35,37}$].

Intermediate-15: 5-(2-Chloro-6-methylpyridin-4-yl)-3-methyl-1,3,4-oxadiazol-2(3H)-one

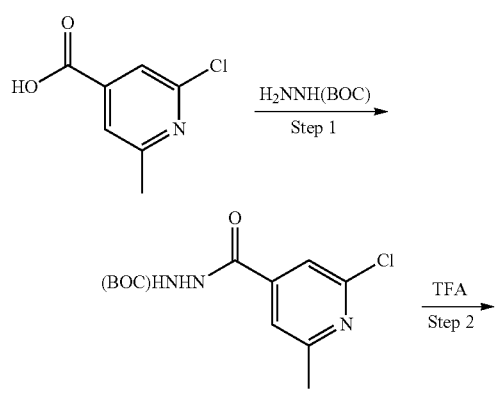

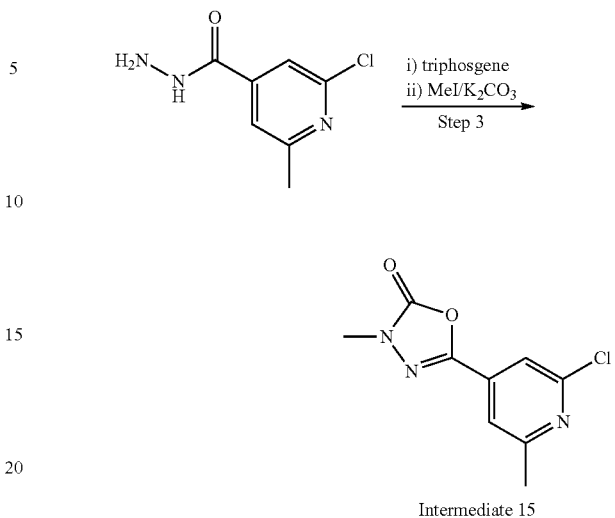

Intermediate 15

Step-1: t-Butyl-2-(2-chloro-6-methylisonicotinoyl)hydrazinecarboxylate: To a stirred solution of 2-chloro-6-methylisonicotinic acid (4.0 g, 23.3 mmol) in DMF (40 mL) was added successively tert-butyl hydrazine carboxylate (3.0 g, 23.3 mmol), TBTU (6.0 g, 18.6 mmol) and DIPEA (12.2 mL, 69.9 mmol). After stirring for 12 h at RT, water (20 mL) was added to the reaction followed by ethyl acetate (50 mL). The layers were separated and the aqueous layer was extracted with ethyl acetate (3×50 mL). The combined organic layers were washed with brine (50 mL), dried (Na$_{2}$SO$_{4}$) and filtered. The filtrate was concentrated under vacuum to afford 3.0 g (45%) of the title compound as white solid. $^{1}$HNMR (400 MHz, CDCl$_{3}$) δ 8.65 (s, D$_{2}$O exchangeable, 1H), 7.48 (s, 1H), 7.42 (s, 1H), 6.77 (s, D$_{2}$O exchangeable, 1H), 2.59 (s, 3H), 1.53 (s, 9H); GC-MS (m/z) 185 (M)$^{+}$ Step-2: 2-Chloro-6-methylisonicotinohydrazide: To a (0° C.) cooled solution of step-1 intermediate (3.0 g, 10.5 mmol) in DCM (15 mL) was added trifluoroacetic acid (15 mL). After stirring for 2 h at RT, solvent was evaporated under vacuum. Water (20 mL) was added to the resulting residue followed by ethyl acetate (30 mL). The layers were separated and the aqueous layer was extracted with ethyl acetate (2×50 mL). The combined organic layers were washed with brine (20 mL), dried (Na$_{2}$SO$_{4}$) and filtered. The filtrate was concentrated under vacuum and the crude product was purified by flash column chromatography to afford 1.80 g (92%) of the title compound as white solid.

Step-3: 5-(2-Chloro-6-methylpyridin-4-yl)-3-methyl-1,3,4-oxadiazol-2(3H)-one: The title compound was prepared from 2-chloro-6-methylisonicotinohydrazide by following the similar procedure sequentially as described in step-3 and step-4 of Intermediate-1.

$^{1}$HNMR (400 MHz, CDCl$_{3}$) δ 7.65 (s, 1H), 7.58 (s, 1H), 3.43 (s, 3H), 2.55 (s, 3H); GC-MS (m/z) 225 (M)$^{+}$.

The below intermediates in Table-2 were prepared from corresponding starting materials by following the similar procedure as described in WO2012056478.

TABLE 2

| Intermediate No: IUPAC name | Structure |
|---|---|
| Intermediate-16: 2,6-Difluoro-N-(4-(4,4,5,5,-tetramethyl-1,3,2-dioxaborolan-2-yl)phenyl)benzamide | 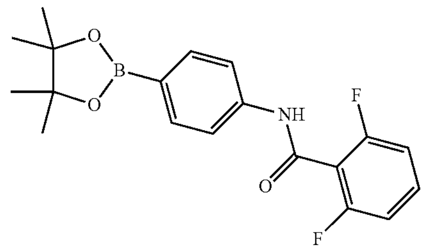 [SMILES: CC1(C)OB(c2ccc(NC(=O)c3c(F)cccc3F)cc2)OC1(C)C] |
| Intermediate-17: 2-Chloro-6-fluoro-N-(4-(4,4,5,5,-tetramethyl-1,3,2-dioxaborolan-2-yl)phenyl)benzamide | 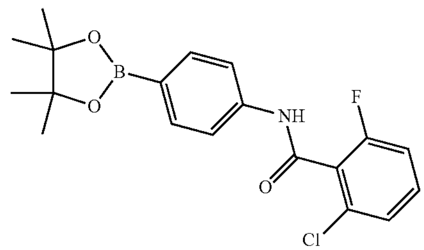 |
| Intermediate-18: 2-Fluoro-6-methyl-N-(4-(4,4,5,5-tetramethyl-1,3,2-dioxaborolan-2-yl)phenyl)benzamide | 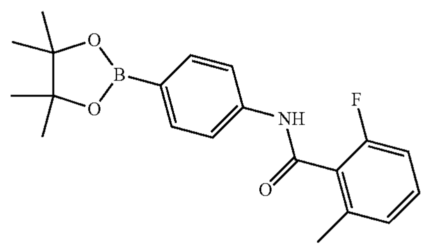 [SMILES: Cc1cccc(F)c1C(=O)Nc1ccc(B2OC(C)(C)C(C)(C)O2)cc1] |
| Intermediate-19: 4-Methyl-N-(4-(4,4,5,5-tetramethyl-1,3,2-dioxaborolan-2-yl)phenyl)-1,2,3-thiadiazol-5-carboxamide | 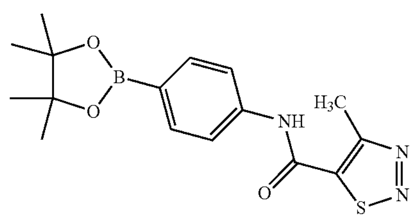 [SMILES: Cc1nnsc1C(=O)Nc1ccc(B2OC(C)(C)C(C)(C)O2)cc1] |
| Intermediate-20: N-(5-Bromopyridin-2-yl)-2,6-difluorobenzamide | 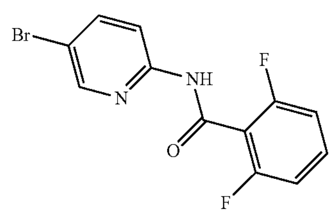 [SMILES: O=C(Nc1ccc(Br)cn1)c1c(F)cccc1F] |
| Intermediate-21: N-(6-Bromopyridin-3-yl)-2,6-difluorobenzamide | 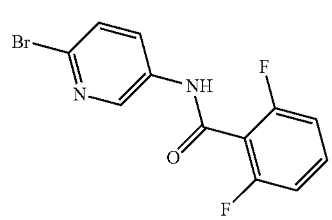 [SMILES: O=C(Nc1ccc(Br)nc1)c1c(F)cccc1F] |

TABLE 2-continued

| Intermediate No: IUPAC name | Structure |
|---|---|
| Intermediate-22: N-(5-Bromopyrazine-2-yl)-2,6-difluorobenzamide | 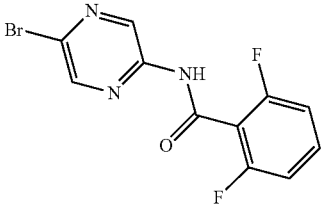 [SMILES: O=C(Nc1cnc(Br)cn1)c1c(F)cccc1F] |
| Intermediate-23: N-(2,6-difluorophenyl)-5-(trimethylstannyl)thiophene-2-carboxamide | 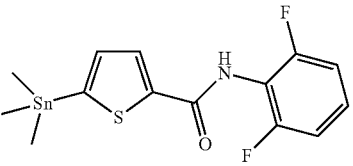 [SMILES: [CH3][Sn]([CH3])([CH3])[c]1ccc(C(=O)Nc2c(F)cccc2F)s1] |
| Intermediate-24: N-(2,6-difluorophenyl)-1-methyl-5-(trimethylstannyl)-1H-pyrrole-2-carboxamide | 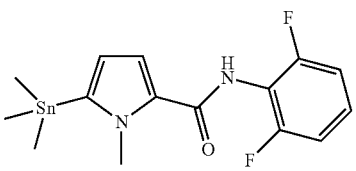 [SMILES: Cn1c(C(=O)Nc2c(F)cccc2F)cc[c]1[Sn]([CH3])([CH3])[CH3]] |

Intermediate-25: N-(5-Chloropyrazine-2-yl)-2,6-difluorobenzamide

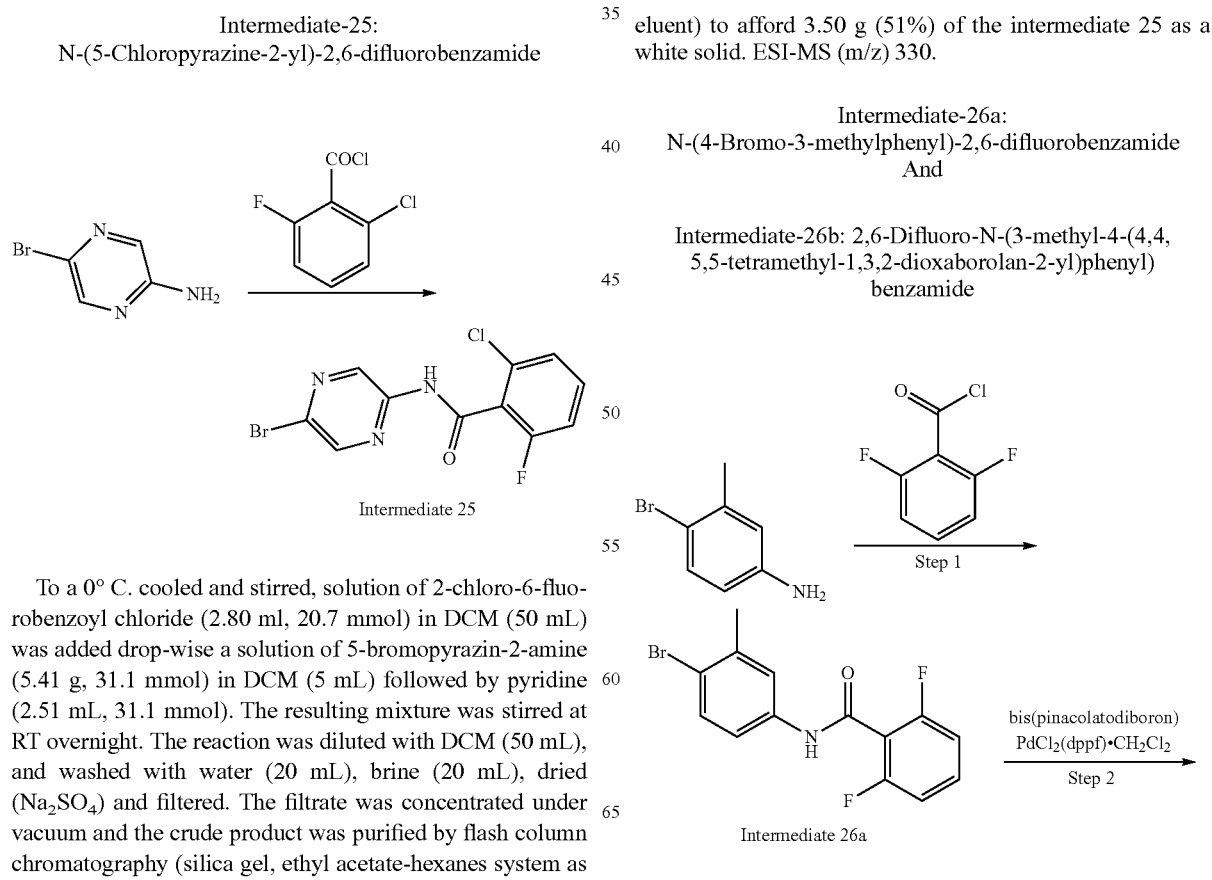

To a 0° C. cooled and stirred, solution of 2-chloro-6-fluorobenzoyl chloride (2.80 ml, 20.7 mmol) in DCM (50 mL) was added drop-wise a solution of 5-bromopyrazin-2-amine (5.41 g, 31.1 mmol) in DCM (5 mL) followed by pyridine (2.51 mL, 31.1 mmol). The resulting mixture was stirred at RT overnight. The reaction was diluted with DCM (50 mL), and washed with water (20 mL), brine (20 mL), dried (Na$_2$SO$_4$) and filtered. The filtrate was concentrated under vacuum and the crude product was purified by flash column chromatography (silica gel, ethyl acetate-hexanes system as eluent) to afford 3.50 g (51%) of the intermediate 25 as a white solid. ESI-MS (m/z) 330.

Intermediate-26a: N-(4-Bromo-3-methylphenyl)-2,6-difluorobenzamide And

Intermediate-26b: 2,6-Difluoro-N-(3-methyl-4-(4,4,5,5-tetramethyl-1,3,2-dioxaborolan-2-yl)phenyl)benzamide

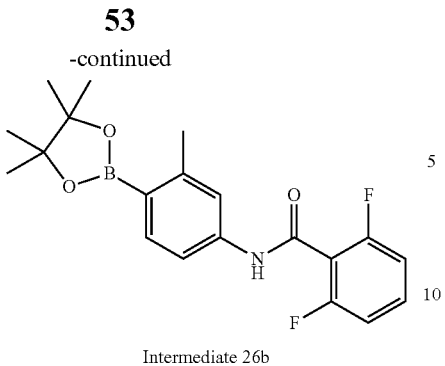

Intermediate 26b

Step-1: N-(4-bromo-3-methylphenyl)-2,6-difluorobenzamide: The title compound was prepared by reacting 4-bromo-3-methylaniline (15 g, 81 mmol) with 2,6-difluorobenzoyl chloride (6.76 mL, 53.7 mmol) in DCM (200 mL) by following the similar procedure reported for Intermediate-25 to afford 12.0 g (68%) the Intermediate-26a as a white solid.

$^1$HNMR (400 MHz, CDCl$_3$) δ 7.76 (s, 1H, D$_2$O exchangeable), 7.57 (d, J=2.0 Hz, 1H), 7.46 (d, J=8.0 Hz, 1H), 7.43-7.39 (m, 1H), 7.31 (dd, J=2.0 & 8.0 Hz, 1H), 6.98 (t, J=8.0 Hz, 2H) 2.40 (s, 3H); ESI-MS (m/z) 326, 328 [(MH)$^+$ Br$^{79,81}$].

Step-2: 2,6-Difluoro-N-(3-methyl-4-(4,4,5,5-tetramethyl-1,3,2-dioxaborolan-2-yl)phenyl)benzamide: To a stirred solution of step-1 intermediate (1.0 g, 3.07 mmol), bis(pinacolato)diboron (0.934 g 3.68 mmol) in dioxane (15 mL), potassium acetate (0.602 g, 6.13 mmol), PdCl$_2$(dppf)-CH$_2$Cl$_2$ adduct (125 mg, 0.153 mmol) were sequentially added. The resulting mixture was thoroughly deoxygenated by subjecting to vacuum/nitrogen cycle three times and the reaction mixture was heated at 120° C. for 12 h under nitrogen atmosphere. The reaction mixture was cooled to RT and filtered through celite. The filtrate was concentrated under vacuum and crude product was purified by column chromatography to afford 1.0 g (87%) of the intermediate 26b as a white solid.

$^1$HNMR (400 MHz, CDCl$_3$) δ 7.78 (d, J=8.0 Hz, 1H), 7.64 (s, 1H), 7.46 (d, J=2.0 Hz, 1H), 7.42 (dd, J=8.0 & 2.0 Hz, 1H), 7.27 (m, 1H), 7.00 (t, J=8.0 Hz, 2H), 2.56 (s, 3H) 1.35 (s, 12H); ESI-MS (m/z) 374 (MH)$^+$

Intermediate-27: N-(2,6-Difluorophenyl)-4-(4,4,5,5-tetramethyl-1,3,2-dioxaborolan-2-yl)benzamide

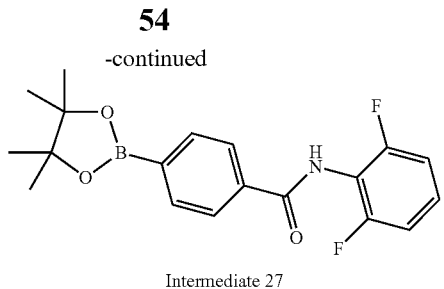

Intermediate 27

Step-1: 4-Bromo-N-(2,6-difluorophenyl)benzamide: To a 0° C. cooled and stirred solution of 4-bromobenzoyl chloride (1.0 g, 4.56 mmol) in DCM (10 mL) was added drop-wise a solution of 2,6-difluoroaniline (0.46 mL, 4.56 mmol) in DCM (2 mL) followed by pyridine (0.48 mL, 5.47 mmol). The resulting mixture was stirred at RT overnight. The reaction was diluted with DCM (10 mL), washed with water (10 mL), brine (10 mL), dried (Na$_2$SO$_4$) and filtered. The filtrate was concentrated under vacuum and the crude product was purified by flash column chromatography (silica gel, ethyl acetate-hexanes system as eluent) to afford 750 mg (53%) of the title product as a white solid. $^1$HNMR (400 MHz, DMSO) δ 10.25 (s, 1H), 7.93 (d, J=8.5 Hz, 2H), 7.77 (d, J=8.5 Hz, 2H), 7.45-7.38 (m, 1H), 7.23 (t, J=8.0 Hz, 2H), ESI-MS (m/z) 312, 314 [(MH)$^+$ Br$^{79,81}$].

Step-2: N-(2,6-Difluorophenyl)-4-(4,4,5,5-tetramethyl-1,3,2-dioxaborolan-2-yl)benzamide: To a stirred solution of step-1 intermediate (5.40 g, 17.3 mmol) in dioxane (50 mL), 4,4,4',4',5,5,5',5'-octamethyl-2,2'-bi(1,3,2-dioxaborolane) (5.27 g, 20.7 mmol, potassium acetate (5.43 g, 55.4 mmol) and [1,1'-bis(diphenyl phosphino)-ferrocene)dichloro palladium(II) dichloro methane complex (0.706 g, 0.86 mmol) were sequentially added. The resulting mixture was thoroughly deoxygenated by subjecting to a vacuum/nitrogen cycle three times and then heated at 100° C. for 6 h under nitrogen atmosphere. The reaction mixture was cooled to RT and filtered through celite. The filtrate was concentrated under vacuum and the crude product was purified by flash column chromatography (silica gel, ethyl acetate-hexanes system as eluent) to afford 4.80 g (77%) the title compound as a white solid. $^1$HNMR (400 MHz, CDCl$_3$) δ 7.95-7.90 (m, 4H), 7.47 (s, 1H), 7.27-7.23 (m, 1H), 7.01 (t, J=8.0 Hz, 2H); ESI-MS (m/z) 360 (MH)$^+$.

Intermediate-28:
5-Bromo-N-(2,6-difluorobenzyl)pyridin-2-amine

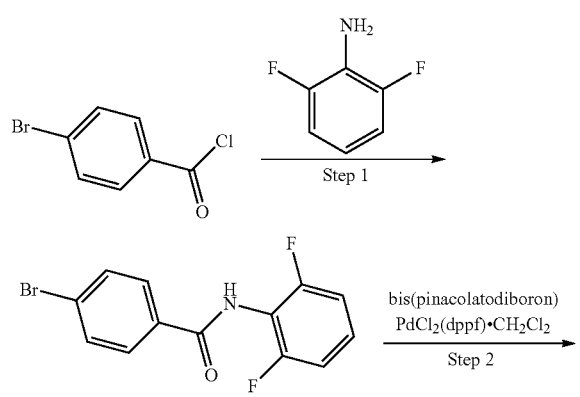

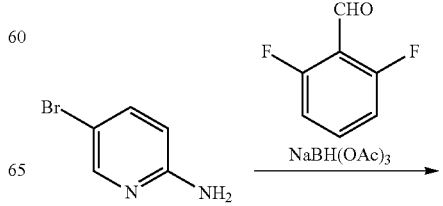

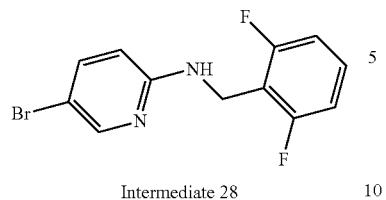

Intermediate 28

To a solution of 5-bromopyridin-2-amine (3.04 g, 17.6 mmol), in ethanol (10 mL), 2,6-difluorobenzaldehyde (1.92 mL, 17.59 mmol) was added followed by the catalytic amount of acetic acid. The resulting mixture was then refluxed for 16 h. Excess ethanol was evaporated under vacuum. The residue was taken in dichloroethane (20 mL) and sodium triacetoxyborohydride (14.91 g, 70.4 mmol), was added and reaction was heated at 85° C. for 16 h. The reaction mixture was cooled to RT and diluted with DCM (50 mL) followed by water (30 mL). The layers were separated and the aqueous layer was extracted with DCM (3×50 mL). The combined organic layers were washed with brine (50 mL), dried ($Na_2SO_4$) and filtered. The filtrate was concentrated under vacuum to afford 1.50 g (29%) of the intermediate 28 as white solid. $^1$HNMR (400 MHz, $CDCl_3$) δ 8.12 (d, J=2.5 Hz, 1H), 7.52 (dd, J=8.5 &2.5 Hz, 1H), 7.29-7.22 (m, 1H), 6.91 (t, J=8.0 Hz, 2H), 6.48 (d, J=8.5 Hz, 1H), 5.17 (s, $D_2O$ exchangeable, 1H), 4.57 (s, 2H); ESI-MS 299, 301 [(MH)$^+$, Br$^{79,81}$].

Intermediate-29: 6-Bromo-N-(2,6-difluorobenzyl)pyridin-3-amine

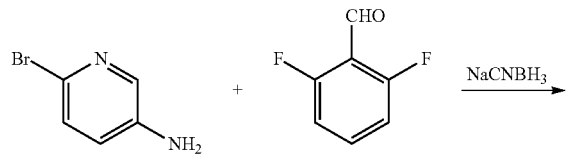

Intermediate 29

To a solution of 6-bromopyridin-3-amine (500 mg, 2.89 mmol), in MeOH (3 mL), acetic acid (0.165 mL, 2.89 mmol), 2,6-difluorobenzaldehyde (0.31 mL, 2.89 mmol) was added. After stirring the resulting mixture at RT for 12 h, sodium cyanoborohydride (363 mg, 5.78 mmol) was added at 0° C. and resulting mixture was stirred at RT for 6 h. Solvent was evaporated under vacuum. Residue was purified by column chromatography to afford 200 mg (23%) of the title compound as white solid. GC-MS-298, 300 [M$^+$, Br$^{79,81}$]

Intermediate-30: 5-Bromo-N-(2-chloro-6-fluorophenyl)thiophene-2-carboxamide

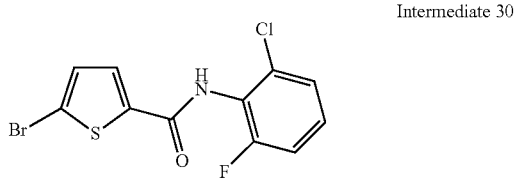 [SMILES: O=C(Nc1c(F)cccc1Cl)c1ccc(Br)s1]

Intermediate 30

The title compound was prepared by following the analogous procedure as described in WO2012056478. $^1$HNMR (400 MHz, $CDCl_3$) δ 7.47 (d, J=4.0 Hz, 1H), 7.31 (bs, 1H), 7.30-7.22 (m, 2H), 7.15-7.11 (m, 2H); ESI-MS (m/z) 334 (MH)$^+$

Intermediate-31: 5-Bromo-N-(3-methylpyridin-4-yl)thiophene-2-carboxamide

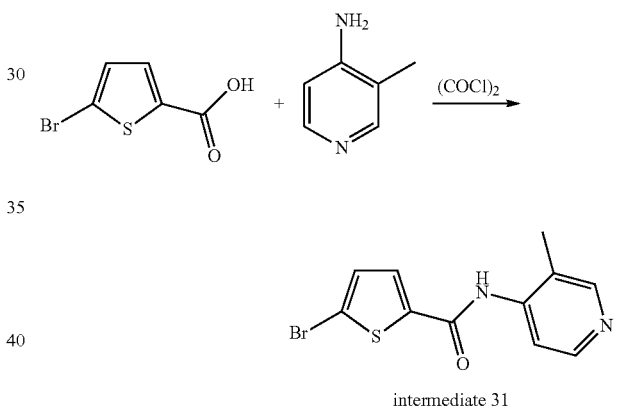

intermediate 31

To a (0° C.) cooled and stirred solution of 5-bromothiophene-2-carboxylic acid (1.91 g, 9.25 mmol) in DCM (20 mL) was added oxalyl chloride (4.05 mL, 46.2 mmol) followed by the addition of catalytic amount of DMF. Reaction was allowed to stir at 0° C. for 2 h. The resulting reaction mixture was then concentrated under vacuum, obtained residue was dissolved in DMF (2 mL) and added to a separately prepared (0° C.) cooled mixture containing 3-methylpyridin-4-amine (1.23 g, 11.37 mmol) and sodium hydride (0.444 g, 18.49 mmol) in DMF (10 mL). After stirring the reaction at RT overnight, quenched with ice cold water (20 mL), followed by the addition of ethyl acetate (30 mL). The layers were separated and the aqueous layer was extracted with ethyl acetate (3×20 mL). The combined organic layers were washed with water (2×50 mL), brine (20 mL), dried ($Na_2SO_4$) and filtered. The filtrate was concentrated under vacuum and the crude product was purified by flash column chromatography (silica gel, DCM-methanol system as eluent) to afford 1.10 g (40%) of the title product as a white solid. $^1$HNMR (400 MHz, $CDCl_3$) δ 8.44 (d, J=5.5 Hz, 1H), 8.40 (s, 1H), 8.14 (d, J=5.5 Hz, 1H), 7.70 (s, 1H), 7.40 (d, J=4.0 Hz, 1H), 7.13 (d, J=4.0 Hz, 1H), ESI-MS (m/z) 297, 298 [(MH)+ Br[79,81]].

Intermediate-32: 5-bromo-N-(2,6-difluorophenyl)furan-2-carboxamide

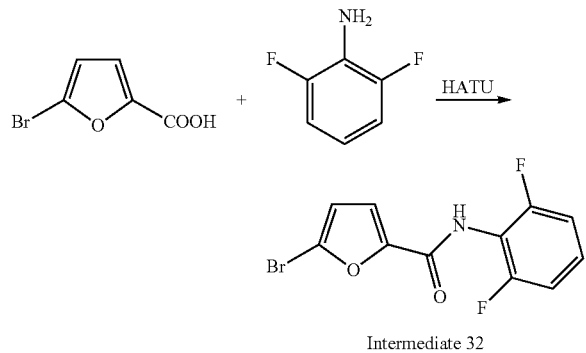

Intermediate 32

5-Bromo-N-(2,6-difluorophenyl)furan-2-carboxamide: To a solution of 5-bromofuran-2-carboxylic acid acid (2.0 g, 10.4 mmol) in DMF (30 mL), 2,6-difluoroaniline (1.27 mL, 12.5 mmol), DIPEA (3.66 mL, 20.9 mmol) and HATU (4.78 g, 12.5 mmol) were successively added. The resulting mixture was stirred at RT for 3 h. The reaction mixture was diluted with ethyl acetate (50 mL) followed by water (30 mL). The layers were separated and the aqueous layer was extracted with ethyl acetate (3×20 mL). The combined organic layers were washed with brine (50 mL), dried (Na$_2$SO$_4$) and filtered. The filtrate was concentrated under vacuum. The crude product was purified by flash column chromatography (silica gel, 20% ethyl acetate in hexane) to afford 400 mg (13%) of the title compound as white solid. $^1$HNMR (400 MHz, CDCl$_3$) δ 7.57 (s, D$_2$O exchangeable, 1H), 7.31-7.25 (m, 1H), 7.24 (d, J=3.5 Hz, 1H), 7.01 (t, J=7.5 Hz, 2H), 6.54 (d, J=3.5 Hz, 1H); ESI-MS (m/z) 302, 304 [(MH)+ Br[79,81]].

Intermediate-33: 3-(5-Bromo-6-ethylpyridin-3-yl)-4,4-dimethylisoxazol-5(4H)-one

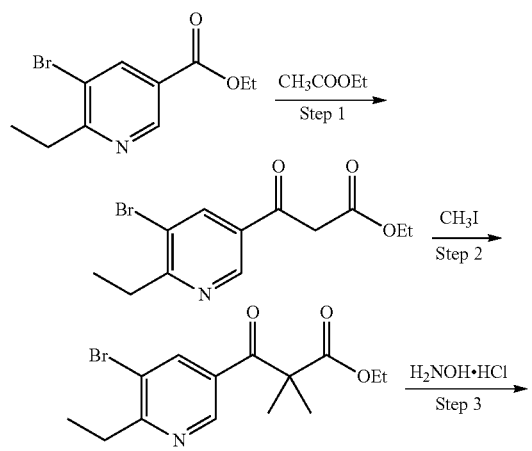

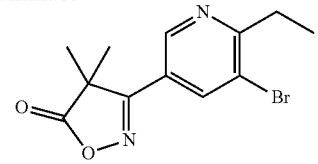

Intermediate 33

Step-1: Ethyl 3-(5-bromo-6-ethylpyridin-3-yl)-3-oxopropanoate: To a stirred solution of ethyl 5-bromo-6-ethylnicotinate (1.1 g, 4.26 mmol) and ethyl acetate (1.25 mL, 12.79 mmol) in anhydrous THF (10 mL) was added LiHMDS (1M in THF, 6.39 mL, 6.39 mmol) at −50° C. over a period of 10 min. The reaction was then stirred for 30 min at the same temperature and quenched with acetic acid (2 mL). The reaction was basified with aqueous saturated sodium bicarbonate solution (3 mL) followed by the dilution with ethyl acetate (50 mL) and water (25 mL). The layers were separated and the aqueous layer was extracted with ethyl acetate (2×30 mL). The combined organic layers were washed with brine (25 mL), dried (Na$_2$SO$_4$) and filtered. The filtrate was rotary evaporated and the crude product was purified by flash column chromatography (silica gel, ethyl acetate-hexanes system as eluent) to afford 930 mg (72%) of the title compound as white solid. $^1$HNMR (400 MHz, DMSO-d$_6$) δ 9.01 (d, J=2.0 Hz, 1H), 8.46 (d, J=2.0 Hz, 1H), 4.27 (s, 2H), 4.13 (q, J=7.0 Hz, 2H), 2.98 (q, J=7.0 Hz, 2H), 1.26 (t, J=7.0 Hz, 3H), 1.21 (t, J=7.0 Hz, 3H); ESI-MS (m/z) 300, 302 [(MH)+, Br[79,81]]

Step-2: Ethyl 3-(5-bromo-6-ethylpyridin-3-yl)-2,2-dimethyl-3-oxopropanoate: To a 0° C. cooled and stirred suspension of sodium hydride (60% dispersion in oil, 120 mg, 5 mmol), in DMF (3 mL) was added ethyl 3-(5-bromo-6-ethylpyridin-3-yl)-3-oxopropanoate (0.5 g, 1.66 mmol) in DMF (7 mL) over a period of 15 min. The reaction mixture was then stirred for 15 min at the same temperature and Iodomethane (365 μl, 5.83 mmol) was added to the above mixture. The resulting mixture was then warmed to room temperature and stirred for 3 h. The reaction mixture was diluted with water (30 mL) followed by ethyl acetate (50 mL). The layers were separated and the aqueous layer was extracted with ethyl acetate (2×30 mL). The combined organic layers were washed with brine (20 mL), dried (Na$_2$SO$_4$) and filtered. The filtrate was rotary evaporated to afford 300 mg (54%) of the title compound as white solid. $^1$HNMR (400 MHz, DMSO-d$_6$) δ 8.77 (d, J=2.0 Hz, 1H), 8.18 (d, J=2.0 Hz, 1H), 4.12 (q, J=7.0 Hz, 2H), 2.96 (q, J=7.0 Hz, 2H), 1.46 (s, 6H), 1.25 (t, J=7.0 Hz, 3H), 1.03 (t, J=7.0 Hz, 3H); ESI-MS (m/z) 328, 330 [(MH+, Br[79,81]].

Step-3: 3-(5-Bromo-6-ethylpyridin-3-yl)-4,4-dimethyl-isoxazol-5(4H)-one: To (0° C.) cooled solution of ethyl 3-(5-bromo-6-ethylpyridin-3-yl)-2,2-dimethyl-3-oxopropanoate (320 mg, 0.97 mmol) in ethanol (7 mL) was added solution of Hydroxylamine hydrochloride (81 mg, 1.17 mmol) in water (3 mL) followed by a solution of KOH (120 mg, 2.14 mmol) in water (2 mL). The resulting mixture was warmed to room temperature and stirred at 78° C. for 1 h. The reaction was cooled back down to room temperature and diluted with water (10 mL) followed by ethyl acetate (50 mL). The layers were separated and the aqueous layer was extracted with ethyl acetate (2×30 mL). The combined organic layers were washed with brine (50 mL), dried (Na$_2$SO$_4$) and filtered. The filtrate was rotary evaporated and the crude product was purified by flash column chromatography to afford 130 mg (44%)

of the title compound as white solid. ¹HNMR (400 MHz, DMSO-d₆) δ 8.92 (d, J=2.0 Hz, 1H), 8.34 (d, J=2.0 Hz, 1H), 2.98 (q, J=7.0 Hz, 2H), 1.55 (s, 6H), 1.25 (t, J=7.0 Hz, 3H); ESI-MS (m/z) 297, 299 [(MH)⁺, Br⁷⁹,⁸¹]

Intermediate-34: N-(6-bromo-4-methylpyridin-3-yl)-2,6-difluorobenzamide

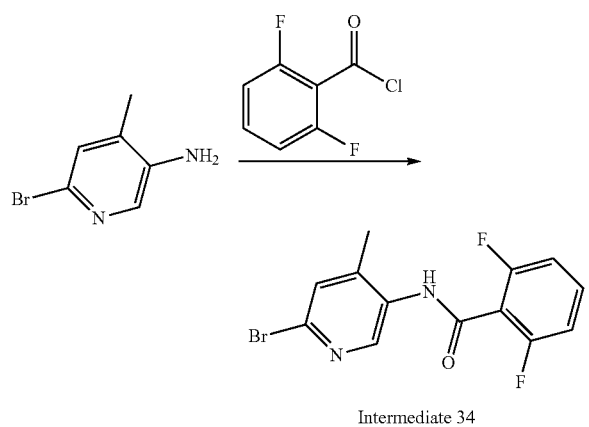

Intermediate 34

To a (0° C.) cooled and stirred solution of 2,6-difluorobenzoyl chloride (357 μL, 2.83 mmol) in DCM (5 mL) was added 6-bromo-4-methylpyridin-3-amine (583 mg, 3.12 mmol) followed by the addition of pyridine (344 μL, 4.25 mmol). The resulting mixture was then stirred at room temperature overnight. Water (5 mL) was added to the above mixture and then extracted with DCM (3×10 mL). The combined organic layers were washed with 10% aq.HCl (10 mL), dried (Na₂SO₄) and filtered. The filtrate was concentrated under vacuum to afford 650 mg (70%) of the title compound as a white solid. ¹HNMR (400 MHz, DMSO-d₆) δ 10.56 (s, 1H, D₂O exchangeable), 8.41 (s, 1H), 7.66 (s, 1H), 7.65-7.58 (m, 1H), 7.27 (t, J=7.0 Hz, 2H), 2.27 (m, 3H); (ESI-MS (m/z) 327, 329 [(MH)⁺, Br⁷⁹, ⁸¹].

Intermediate-35: N-(5-Bromo-4-methylpyridin-2-yl)-2,6-difluorobenzamide

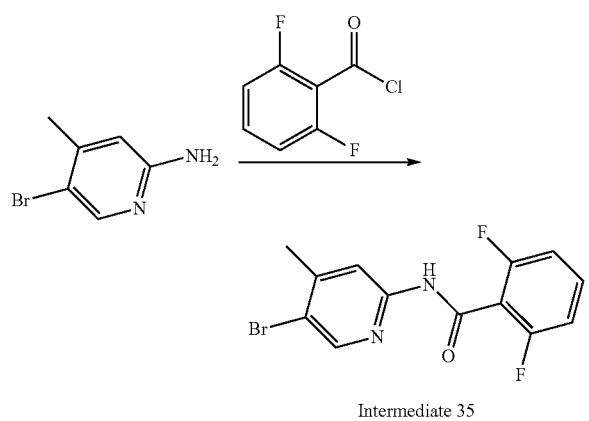

Intermediate 35

To a (0° C.) cooled and stirred solution of 2,6-difluorobenzoyl chloride (500 mg, 2.83 mmol) in DCM (10 mL) was added 4-bromo-3-methylaniline (632 mg, 3.40 mmol) followed by the addition of pyridine (275 μL, 3.40 mmol). The resulting mixture was warmed to room temperature and stirred overnight. Water (10 mL) was then added to the above mixture and extracted with DCM (3×20 mL). The combined organic layers were washed with 10% aq.HCl (10 mL), dried (Na₂SO₄) and filtered. The filtrate was concentrated under vacuum to afford 250 mg (28%) of the title compound as a white solid. ¹HNMR (400 MHz, DMSO-d₆) δ 11.44 (s, 1H, D₂O exchangeable), 8.53 (s, 1H), 7.63 (s, 1H), 7.61-7.54 (m, 1H), 7.21 (t, J=7.0 Hz, 2H), 2.41 (m, 3H); (ESI-MS (m/z) 327, 329 [(MH)⁺ Br⁷⁹,⁸¹]

EXAMPLES

General Procedure for the Coupling Reaction

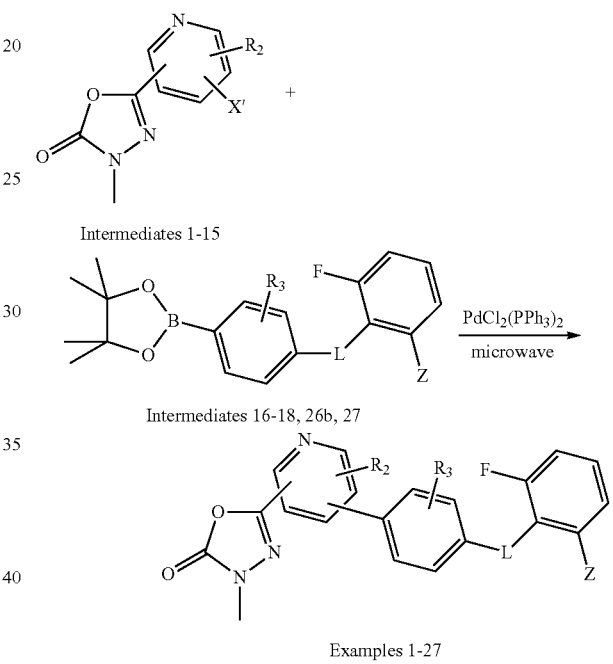

Z = F, Cl, Me
L = NHCO or CONH

Method-A: To a nitrogen purged stirred solution of halo intermediate mentioned in above scheme (1.0 eq) in dioxane (5 mL) in a microwave tube, borate intermediate (1.0 eq) mentioned in above scheme, aqueous sodium carbonate solution (2N) and Pd(PPh₃)₂Cl₂ (0.05 eq) were sequentially added. The resulting mixture was thoroughly deoxygenated by purging nitrogen for a period of 15 minutes and then heated to 130° C. and maintained for 30 minin microwave (Biotage). The reaction mixture was cooled to RT and filtered through celite. The filtrate was concentrated under vacuum and the crude product was purified by flash column chromatography (silica gel, ethyl acetate-hexane system as eluent) to afford the desired product as a white solid.

Method-B: To a nitrogen purged and stirred solution of halo intermediate (1.0 eq) mentioned in above scheme in dioxane (5 mL) in a sealed tube, borate intermediate (1.0 eq) mentioned in above scheme, aqueous sodium carbonate solution (2N) and Pd(PPh₃)₂Cl₂ (0.05 eq) were sequentially added. The resulting mixture was thoroughly deoxygenated by purging nitrogen for a period of 15 minutes and then heated to 130° C. and further maintained for 18 h. The reaction mixture was cooled to RT and filtered through celite. The filtrate was concentrated under vacuum and the crude product was purified by flash column chromatography (silica gel, ethyl acetate-hexanes system as eluent)/preparative HPLC to afford the desired product as a white solid.

Method-C: To a stirred solution of halo intermediate (0.1 eq) mentioned in above scheme in dioxane (5 mL) in a round bottomed flask, borate intermediate (0.1 eq) mentioned in above scheme, aqueous solution of Na$_2$CO$_3$ (2M) and bis(triphenylphosphine)palladium(II) chloride (0.05 eq) were sequentially added. The resulting mixture was thoroughly deoxygenated by subjecting to vacuum/nitrogen cycle three times and the reaction mixture was refluxed for 24 h under nitrogen atmosphere. The reaction mixture was cooled to RT and then filtered through celite. The filtrate was concentrated under vacuum and crude product was purified with column chromatography (silica gel, ethyl acetate-hexanes system as eluent)/preparative HPLC to afford the title compound as a white solid.

Examples 1-27

The below Examples of 1 to 27 in Table-3 were prepared by following any of the general procedures described in Method-A, Method-B or Method-C by using appropriate intermediates.

TABLE 3

| Example No: IUPAC name | Structure | $^1$HNMR/ESI-MS |
|---|---|---|
| Example-1: 2,6-Difluoro-N-(4-(2-methyl-5-(4-methyl-5-oxo-4,5-dihydro-1,3,4-oxadiazol-2-yl)pyridin-3-yl)phenyl)benzamide | 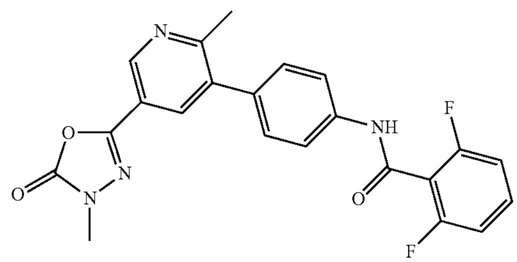 [SMILES: Cc1ncc(-c2nn(C)c(=O)o2)cc1-c1ccc(NC(=O)c2c(F)cccc2F)cc1] | $^1$HNMR (400 MHz, CDCl$_3$) δ 8.94 (d, J = 2.0 Hz, 1H), 7.94 (d, J = 2.0 Hz, 1H), 7.94 (s, D$_2$O exchangeable, 1H), 7.78 (d, J = 8.5 Hz, 2H), 7.48-7.43 (m, 1H), 7.37 (d, J = 8.5 Hz, 2H), 7.03 (t, J = 8.0 Hz, 2H), 3.52 (s, 3H), 2.60 (s, 3H); ESI-MS (m/z) 423 (MH)$^+$. |
| Example-2: N-(4-(2-ethyl-5-(4-methyl-5-oxo-4,5-dihydro-1,3,4-oxadiazol-2-yl)pyridin-3-yl)phenyl)-2,6-difluorobenzamide | 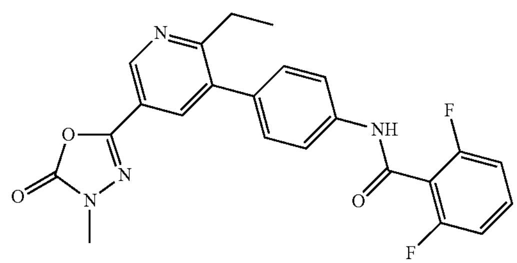 [SMILES: CCc1ncc(-c2nn(C)c(=O)o2)cc1-c1ccc(NC(=O)c2c(F)cccc2F)cc1] | $^1$HNMR (400 MHz, CDCl$_3$) δ 8.99 (d, J = 2.0 Hz, 1H), 7.92 (d, J = 2.0 Hz, 1H), 7.91 (s, D$_2$O exchangeable, 1H), 7.78 (d, J = 8.5 Hz, 2H), 7.45 (m, 1H), 7.35 (d, J = 8.5 Hz, 1H), 7.03 (t, J = 8.0 Hz, 2H), 3.52 (s, 3H), 2.86 (q, J = 7.0 Hz, 2H), 1.24 (t, J = 7.0 Hz, 3H); ESI-MS (m/z) 436(M)$^+$ |
| Example-3: N-(2,6-Difluorophenyl)-4-(2-ethyl-5-(4-methyl-5-oxo-4,5-dihydro-1,3,4-oxadiazol-2-yl)pyridin-3-yl)benzamide | 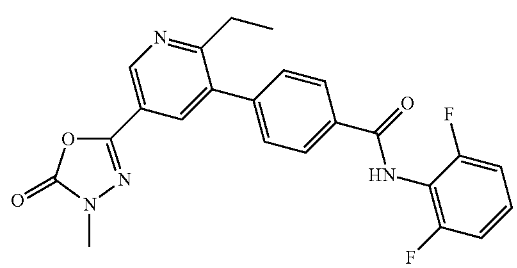 [SMILES: CCc1ncc(-c2nn(C)c(=O)o2)cc1-c1ccc(C(=O)Nc2c(F)cccc2F)cc1] | $^1$HNMR (400 MHz, CDCl$_3$) δ 9.05 (d, J = 2.0 Hz, 1H), 8.06 (d, J = 8.0 Hz, 2H), 7.94 (d, J = 2.0 Hz, 1H), 7.52 (s, 1H), 7.48 (d, J = 8.0 Hz, 2H), 7.32-7.25 (m, 1H), 7.04 (t, J = 8.0 Hz, 2H), 3.53 (s, 3H), 2.85 (q, J = 7.5 Hz, 2H), 1.25 (t, J = 7.5 Hz, 3H); ESI-MS (m/z) 437 (MH)$^+$ |
| Example-4: N-(4-(2-Cyclopropyl-5-(4-methyl-5-oxo-4,5-dihydro-1,3,4-oxadiazol-2-yl)pyridin-3-yl)phenyl)-2,6-difluorobenzamide | 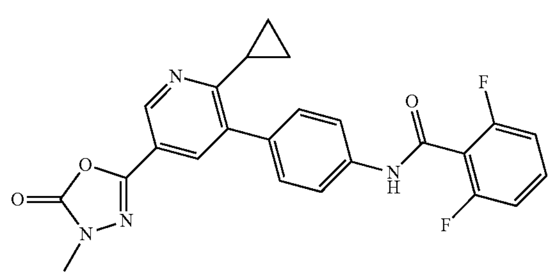 [SMILES: Cn1nc(-c2cnc(C3CC3)c(-c3ccc(NC(=O)c4c(F)cccc4F)cc3)c2)oc1=O] | $^1$HNMR (400 MHz, CDCl$_3$) δ 8.86 (d, J = 2.0 Hz, 1H), 7.89 (d, J = 2.0 Hz, 1H), 7.7-7.77 (m, 3H), 7.51-7.47 (m, 3H), 7.04 (t, J = 8.0 Hz, 2H), 3.51 (s, 3H), 2.18-2.14 (m, 1H), 1.26-1.25 (m, 2H), 1.01-0.98 (m, 2H); ESI-MS (m/z) 449 (MH)$^+$ |

TABLE 3-continued

| Example No: IUPAC name | Structure | ¹HNMR/ESI-MS |
|---|---|---|
| Example-5: 4-(2-cyclopropyl-5-(4-methyl-5-oxo-4,5-dihydro-1,3,4-oxadiazol-2-yl)pyridin-3-yl)-N-(2,6-difluorophenyl)benzamide | 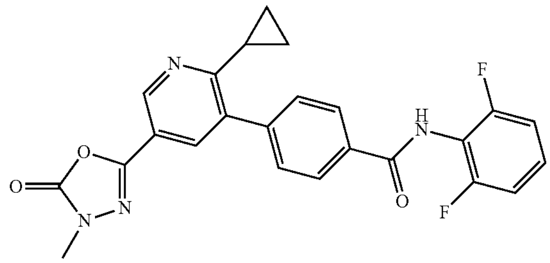 [SMILES: Cn1nc(-c2cnc(C3CC3)c(-c3ccc(C(=O)Nc4c(F)cccc4F)cc3)c2)oc1=O] | ¹HNMR (400 MHz, CDCl₃) δ 8.90 (d, J = 2.0 Hz, 1H), 8.07 (d, J = 8.5 Hz, 1H), 7.91 (d, J = 2.0 Hz, 1H), 7.62 (d, J = 8.5 Hz, 1H), 7.55 (s, 1H), 7.30-7.24 (m, 1H), 7.03 (t, J = 8.0 Hz, 2H), 3.52 (s, 3H), 2.11-2.04 (m, 1H), 1.29-1.26 (m, 2H), 1.09-0.98 (m, 2H); ESI-MS (m/z) 449 (MH)⁺ |
| Example-6: 2,6-Difluoro-N-(4-(2-methoxy-5-(4-methyl-5-oxo-4,5-dihydro-1,3,4-oxadiazol-2-yl)pyridin-3-yl)phenyl)benzamide | 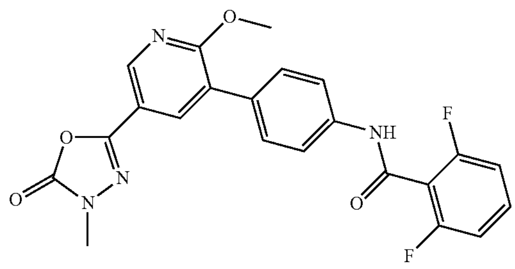 [SMILES: COc1ncc(-c2nn(C)c(=O)o2)cc1-c1ccc(NC(=O)c2c(F)cccc2F)cc1] | ¹HNMR (400 MHz, CDCl₃) δ 8.60 (d, J = 2.5 Hz, 1H), 8.03 (d, J = 2.5 Hz, 1H), 7.80 (s, 1H), 7.76 (d, J = 8.5 Hz, 2H), 7.62 (d, J = 8.5 Hz, 2H), 7.45 (m, 1H), 7.03 (t, J = 8.0 Hz, 2H), 4.05 (s, 3H), 3.51 (s, 3H); ESI-MS (m/z) 439(MH)⁺ |
| Example-7: 2,6-difluoro-N-(4-(5-(4-methyl-5-oxo-4,5-dihydro-1,3,4-oxadiazol-2-yl)-2-(trifluoromethyl)pyridin-3-yl)phenyl)benzamide | 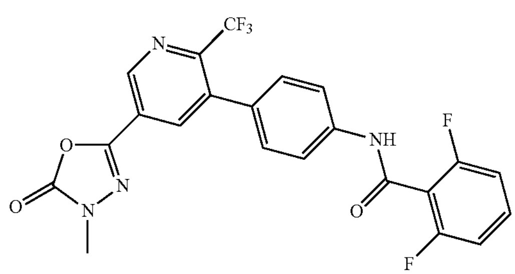 | ¹HNMR (400 MHz, CDCl₃) δ 9.13 (s, 1H), 8.14 (s, 1H), 7.83 (s, 1H), 7.80 (d, J = 8.0 Hz, 2H), 7.47 (m, 1H), 7.39 (d, J = 8.0 Hz, 2H), 7.04 (t, J = 8.0 Hz, 2H), 3.56 (s, 3H); ESI-MS (m/z) 477 (MH)⁺ |
| Example-8: 2,6-difluoro-N-(3-methyl-4-(5-(4-methyl-5-oxo-4,5-dihydro-1,3,4-oxadiazol-2-yl)-2-(trifluoromethyl)pyridin-3-yl)phenyl)benzamide | 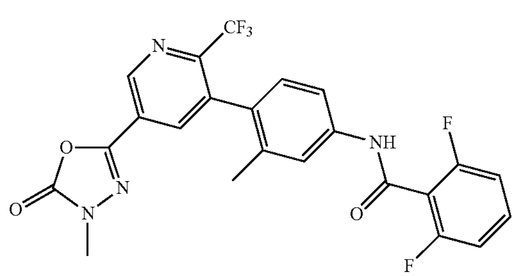 [SMILES: Cc1cc(NC(=O)c2c(F)cccc2F)ccc1-c1cc(-c2nn(C)c(=O)o2)cnc1C(F)(F)F] | ¹HNMR (400 MHz, CDCl₃) δ 9.16 (s, 1H), 8.06 (s, 1H), 7.70 (s, 2H), 7.53 (d, J = 8.0 Hz, 1H), 7.43-7.46 (m, 1H), 7.15 (d, J = 8.0 Hz, 1H), 7.05 (t, J = 8.0 Hz 2H), 3.56 (s, 3H), 2.10 (s, 3H); ESI-MS (m/z) 491(MH)⁺ |
| Example-9: 2-Chloro-6-fluoro-N-(4-(5-(4-methyl-5-oxo-4,5-dihydro-1,3,4-oxadiazol-2-yl)-2-(trifluoromethyl)pyridin-n-3-yl)phenyl)benzamide | 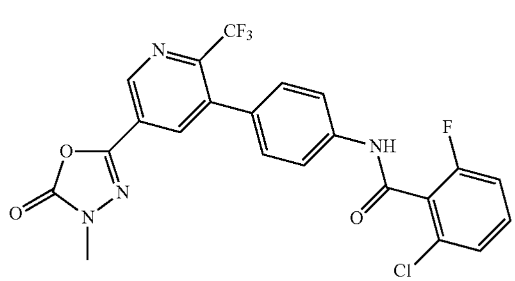 [SMILES: Cn1nc(-c2cnc(C(F)(F)F)c(-c3ccc(NC(=O)c4c(F)cccc4Cl)cc3)c2)oc1=O] | ¹HNMR (400 MHz, CDCl₃) δ 9.13 (d, J = 1.5 Hz, 1H), 8.14 (d, J = 1.5 Hz, 1H), 7.79 (d, J = 8.0 Hz, 2H), 7.67 (s, D₂O exchangeable, 1H), 7.43-7.38 (m, 3H), 7.30 (d, J = 8.0 Hz, 1H), 7.14 (t, J = 8.0 Hz 1H), 3.56 (s, 3H); ESI-MS (m/z) 493(MH)⁺ |

TABLE 3-continued

| Example No: IUPAC name | Structure | ¹HNMR/ESI-MS |
|---|---|---|
| Example-10: 2,6-Difluoro-N-(4-(5-(4-methyl-5-oxo-4,5-dihydro-1,3,4-oxadiazol-2-yl)-2-(methylamino)pyridin-3-yl)phenyl)benzamide | 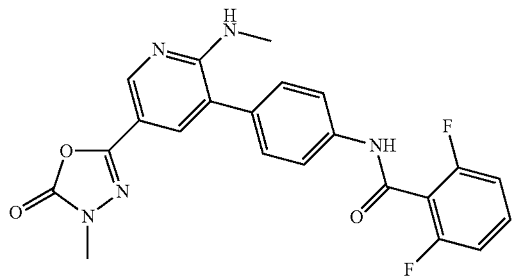 [SMILES: CNc1ncc(-c2nn(C)c(=O)o2)cc1-c1ccc(NC(=O)c2c(F)cccc2F)cc1] | ¹HNMR (400 MHz, DMSO) δ 10.97 (s, 1H), 8.44 (d, J =2.0 Hz, 1H), 7.82 (d, J = 8.5 Hz, 2H), 7.65-7.58 (m, 1H), 7.48 (d, J = 2.0 Hz, 1H), 7.43 (d, J = 8.5 Hz, 2H), 7.29 (t, J = 8.0 Hz, 2H), 6.56 (q, J = 4.5 Hz 1H), 3.36 (s, 3H), 2.83(d, J = 4.5 Hz, 3H); ESI-MS (m/z) 438 (MH)⁺ |
| Example-11: 2-Chloro-6-fluoro-N-(4-(5-(4-methyl-5-oxo-4,5-dihydro-1,3,4-oxadiazol-2-yl)-2-(methylamino)pyridin-3-yl)phenyl)benzamide | 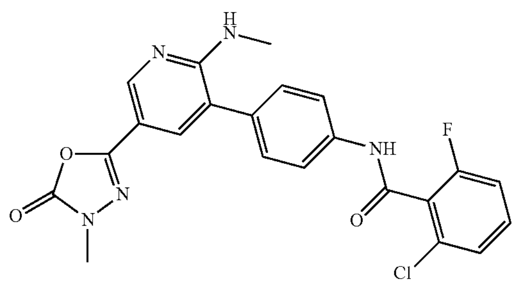 [SMILES: CNc1ncc(-c2nn(C)c(=O)o2)cc1-c1ccc(NC(=O)c2c(F)cccc2Cl)cc1] | ¹HNMR (400 MHz, CDCl₃) δ8.60 (s, 1H), 7.78 (d, J = 8.5 Hz, 2H), 7.66 (s, 1H), 7.61 (s, D₂O exchangeable, 1H), 7.44 (d, J = 8.5 Hz, 2H), 7.41-7.39 (m, 1H), 7.33-7.27 (m, 1H), 7.17-7.13 (m, 1H), 5.04 (brs, 1H), 3.48 (s, 3H), 3.04 (d, J = 4.5 Hz, 3H); ESI-MS (m/z) 454, 456 [(MH)⁺, Cl ³⁵,³⁷] |
| Example-12: 2-Fluoro-6-methyl-N-(4-(5-(4-methyl-5-oxo-4,5-dihydro-1,3,4-oxadiazol-2-yl)-2-(methylamino)pyridin-3-yl)phenyl)benzamide | 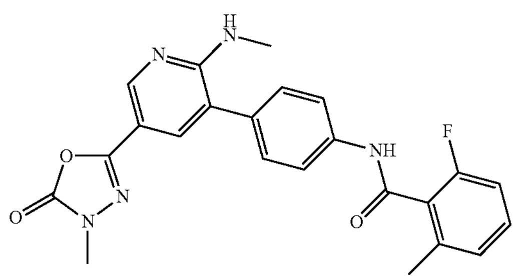 [SMILES: CNc1ncc(-c2nn(C)c(=O)o2)cc1-c1ccc(NC(=O)c2c(C)cccc2F)cc1] | ¹HNMR (400 MHz,CDCl₃) δ 8.60 (d, J = 2.5 Hz, 1H), 7.78 (d, J = 8.5 Hz, 2H), 7.71 (s, 1H), 7.67 (d, J = 2.5 Hz, 1H), 7.43 (d, J = 8.5 Hz, 2H), 7.33-7.31 (m, 1H), 7.10(d, J = 7.5 Hz, 1H), 7.00 (t, J = 8.5 Hz, 1H), 5.12 (q, J = 4.5 Hz 1H), 3.47 (s, 3H), 3.05 (d , J = 4.5 Hz, 3H), 2.51 (s, 3H); ESI-MS (m/z) 434(MH)⁺ |
| Example-13: 2,6-Difluoro-N-(3-methyl-4-(5-(4-methyl-5-oxo-4,5-dihydro-1,3,4-oxadiazol-2-yl)-2-(methylamino)pyridin-3-yl)phenyl)benzamide | 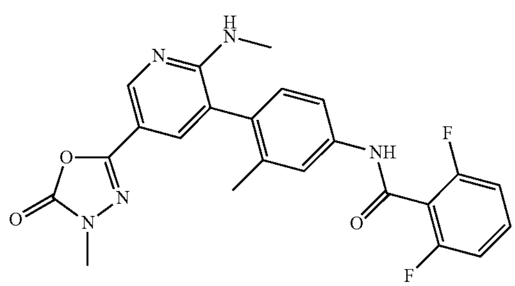 [SMILES: CNc1ncc(-c2nn(C)c(=O)o2)cc1-c1ccc(NC(=O)c2c(F)cccc2F)cc1C] | ¹HNMR (400 MHz, CDCl₃) δ 8.63 (d, J = 2.0 Hz, 1H), 7.69 (brs, 2H), 7.60 (d, J = 2.0 Hz, 1H), 7.53 (dd, J = 8.5 & 2.0 Hz, 1H), 7.49-7.43 (m, 1H), 7.18 (d, J = 8.5 Hz, 1H), 7.05 (t, J = 8.0 Hz, 2H), 4.55 (q, J = 4.5 Hz, 1H), 3.48 (s, 3H), 3.02 (d, J = 4.5 Hz, 3H), 2.17 (s, 3H); ESI-MS (m/z) 452 (MH)⁺ |
| Example-14: 2,6-Difluoro-N-(4-(5-(4-methyl-5-oxo-4,5-dihydro-1,3,4-oxadiazol-2-yl)pyridin-3-yl)phenyl)benzamide | 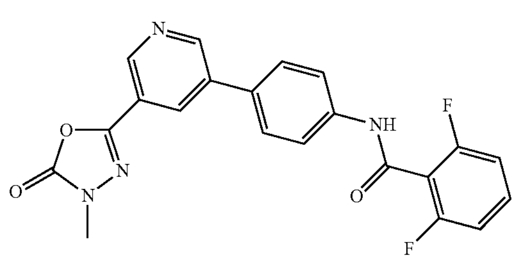 [SMILES: Cn1nc(-c2cncc(-c3ccc(NC(=O)c4c(F)cccc4F)cc3)c2)oc1=O] | ¹HNMR (400 MHz, DMSO-d₆) δ 11.01 (s, D₂O exchangeable, 1H), 9.10 (d, J = 2.0 Hz, 1H), 8.94 (d, J = 2.0 Hz, 1H), 8.35 (t, J = 2.0 Hz, 1H), 7.89-7.84 (m, 4H), 7.66-7.55 (m, 1H), 7.26 (t, J = 8.0 Hz, 2H), 3.46 (s, 3H); ESI-MS (m/z) 409 (MH)⁺ |

TABLE 3-continued

| Example No: IUPAC name | Structure | ¹HNMR/ESI-MS |
|---|---|---|
| Example-15: 2,6-Difluoro-N-(3-methyl-4-(5-(4-methyl-5-oxo-4,5-dihydro-1,3,4-oxadiazol-2-yl)pyridin-3-yl)phenyl)benzamide | 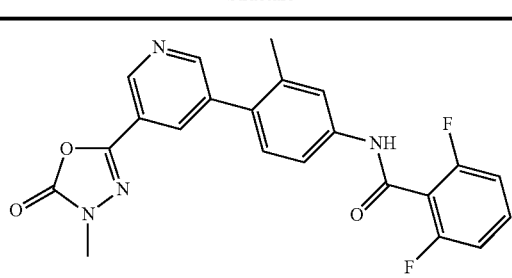 | ¹HNMR (400 MHz, CDCl₃) δ 9.06 (d, J = 2.0 Hz, 1H), 8.72 (d, J = 2.0 Hz, 1H), 8.07 (dd, J = 2.0 & 2.0 Hz 1H), 7.76 (s, D₂O exchangeable, 1H), 7.69 (d, J = 2.0 Hz, 1H), 7.58 (dd, J = 8.0 & 2.0 Hz 1H), 7.46-7.49 (m, 1H), 7.25 (d, J = 8.0 Hz, 1H), 7.06 (t, J = 8.0 Hz 2H), 3.55 (s, 3H), 2.33 (s, 3H); ESI-MS (m/z) 423(MH)⁺ |
| Example-16: N-(4-(4-Ethyl-5-(4-methyl-5-oxo-4,5-dihydro-1,3,4-oxadiazol-2-yl)pyridin-3-yl)phenyl)-2,6-difluorobenzamide | 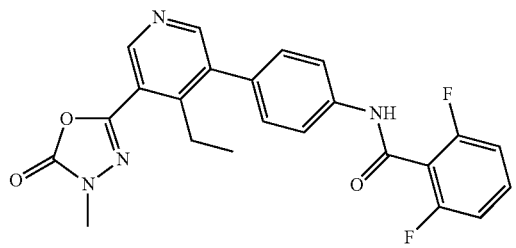 [SMILES: CCc1c(-c2ccc(NC(=O)c3c(F)cccc3F)cc2)cncc1-c1nn(C)c(=O)o1] | ¹HNMR (400 MHz, DMSO-d₆) δ 10.28 (s, D₂O exchangeable, 1H), 8.88 (s, 1H), 8.53 (s, 1H), 8.12 (d, J = 8.0 Hz, 2H), 7.59 (d, J = 8.0 Hz, 2H), 7.42-7.46 (m, 1H), 7.24 (t, J = 8.0 Hz , 2H), 3.45 (s, 3H), 2.86 (q, J = 7.5 Hz, 2H), 0.98 (t, J = 7.5 Hz, 3H); ESI-MS (m/z) 437 (MH)⁺ |
| Example-17: N-(2,6-Difluorophenyl)-4-(4-ethyl-5-(4-methyl-5-oxo-4,5-dihydro-1,3,4-oxadiazol-2-yl)pyridin-3-yl)benzamide | 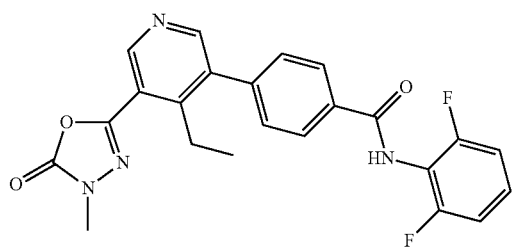 [SMILES: CCc1c(-c2ccc(C(=O)Nc3c(F)cccc3F)cc2)cncc1-c1nn(C)c(=O)o1] | ¹HNMR (400 MHz, DMSO-d₆) δ 10.28 (s, D₂O exchangeable, 1H), 8.88 (s, 1H), 8.53 (s, 1H), 8.12 (d, J = 8.0 Hz, 2H), 7.59 (d, J = 8.0 Hz, 2H), 7.42-7.46 (m, 1H), 7.24 (t, J = 8.0 Hz, 2H), 3.45 (s, 3H), 2.86 (q, J = 7.5 Hz, 2H), 0.98 (t, J = 7.5 Hz, 3H); ESI-MS (m/z) 437 (MH)⁺ |
| Example-18: N-(4-(3-Ethyl-4-(4-methyl-5-oxo-4,5-dihydro-1,3,4-oxadiazol-2-yl)pyridin-2-yl)phenyl)-2,6-difluorobenzamide | 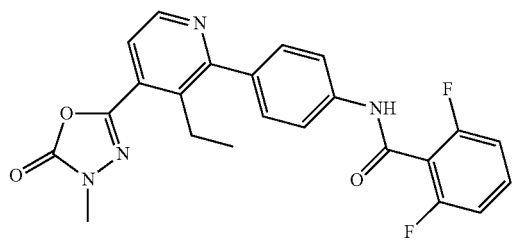 [SMILES: CCc1c(-c2nn(C)c(=O)o2)ccnc1-c1ccc(NC(=O)c2c(F)cccc2F)cc1] | ¹HNMR (400 MHz, CDCl₃) δ 8.66 (d, J = 5.0 Hz, 1H), 8.05 (d, J = 8.5 Hz, 2H), 7.71 (d, J = 5.0 Hz, 1H), 7.70 (s, D₂O exchangeable, 1H), 7.58 (d, J = 8.5 Hz, 2H), 7.29-7.24 (m, 1H), 7.04 (t, J = 8.0 Hz, 2H), 3.58 (s, 3H), 3.01 (q, J = 7.5 Hz, 2H), 1.10 (t, J = 7.5 Hz, 3H); ESI-MS (m/z) 437 (MH)⁺ |
| Example-19: N-(2,6-Difluorophenyl)-4-(3-ethyl-4-(4-methyl-5-oxo-4,5-dihydro-1,3,4-oxadiazol-2-yl)pyridin-2-yl)benzamide | 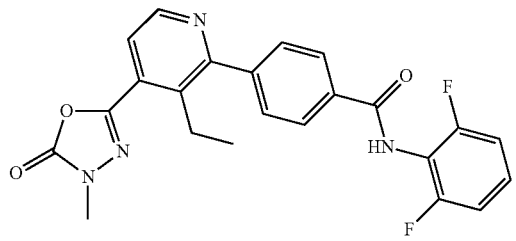 [SMILES: CCc1c(-c2nn(C)c(=O)o2)ccnc1-c1ccc(C(=O)Nc2c(F)cccc2F)cc1] | ¹HNMR (400 MHz, CDCl₃) δ 8.66 (d, J = 5.0 Hz, 1H), 8.05 (d, J = 8.5 Hz, 2H), 7.71 (d, J = 5.0 Hz, 1H), 7.70 (s, D₂O exchangeable, 1H), 7.58 (d, J = 8.5 Hz, 2H), 7.29-7.24 (m, 1H), 7.04 (t, J = 7.5 Hz 2H), 3.58 (s, 3H), 3.01 (q, J = 7.5 Hz, 2H), 1.10 (t, J = 7.5 Hz, 3H); ESI-MS (m/z) 437 (MH)⁺ |
| Example-20: 2,6-Difluoro-N-(4-(3-methyl-4-(4-methyl-5-oxo-4,5-dihydro-1,3,4-oxadiazol-2-yl)pyridin-2-yl)phenyl)benzamide | 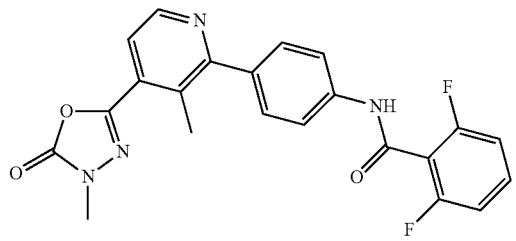 [SMILES: Cc1c(-c2nn(C)c(=O)o2)ccnc1-c1ccc(NC(=O)c2c(F)cccc2F)cc1] | ¹HNMR (400 MHz, CDCl₃) δ 8.64 (d, J = 5.0 Hz, 1H), 7.82(s, D₂O exchangeable, 1H), 7.76 (d, J = 8.5 Hz, 2H), 7.64 (d, J = 5.0 Hz, 1H), 7.54 (d, J = 8.5 Hz, 2H), 7.44-7.47 (m, 1H), 7.05 (t, J = 8.0 Hz, 2H), 3.58 (s, 3H), 2.60 (s, 3H); ESI-MS (m/z) 423 (MH)⁺ |

TABLE 3-continued

| Example No: IUPAC name | Structure | ¹HNMR/ESI-MS |
|---|---|---|
| Example-21: N-(4-(5-Ethyl-4-(4-methyl-5-oxo-4,5-dihydro-1,3,4-oxadiazol-2-yl)pyridin-2-yl)phenyl)-2,6-difluorobenzamide | 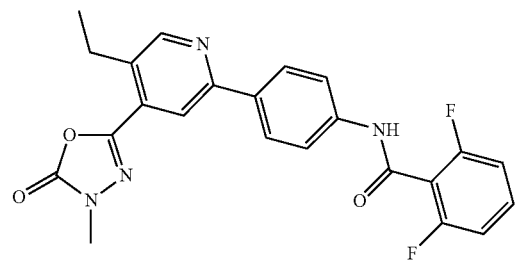 [SMILES: CCc1cnc(-c2ccc(NC(=O)c3c(F)cccc3F)cc2)cc1-c1nn(C)c(=O)o1] | ¹HNMR (400 MHz, CDCl₃) δ 8.73 (s, 1H), 8.20-8.15 (m, 3H), 8.07 (d, J = 8.5 Hz, 2H), 7.51 (s, D₂O exchangeable, 1H), 7.31-7.23 (m, 1H), 7.04 (t, J = 8.0 Hz, 2H), 3.60 (s, 3H), 3.09(q, J = 7.5 Hz, 2H), 1.33 (t, J = 7.5 Hz, 3H); ESI-MS (m/z) 437 (MH)⁺ |
| Example-22: N-(2,6-Difluorophenyl)-4-(5-ethyl-4-(4-methyl-5-oxo-4,5-dihydro-1,3,4-oxadiazol-2-yl)pyridin-2-yl)benzamide | 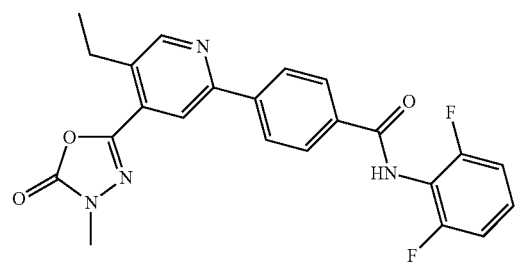 [SMILES: CCc1cnc(-c2ccc(C(=O)Nc3c(F)cccc3F)cc2)cc1-c1nn(C)c(=O)o1] | ¹HNMR (400 MHz, CDCl₃) δ 8.73 (s, 1H), 8.20-8.15 (m, 3H), 8.07 (d, J = 8.5 Hz, 2H), 7.51 (s, D₂O exchangeable, 1H), 7.31-7.23 (m, 1H), 7.04 (t, J = 7.5 Hz, 2H), 3.60 (s, 3H), 3.09(q, J = 7.5 Hz, 2H), 1.33 (t, J = 7.5 Hz, 3H); ESI-MS (m/z) 437 (MH)⁺ |
| Example-23: 2,6-Difluoro-N-(4-(6-methyl-4-(4-methyl-5-oxo-4,5-dihydro-1,3,4-oxadiazol-2-yl)pyridin-2-yl)phenyl)benzamide | 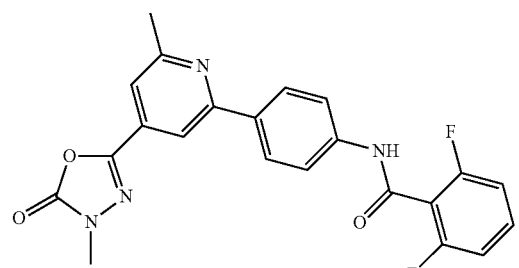 | ¹HNMR (400 MHz, DMSO-d₆) δ 11.01 (s, D₂O exchangeable, 1H), 8.17 (d, J = 8.5 Hz, 2H), 7.98 (s, 1H), 7.84 (d, J = 8.5 Hz, 2H), 7.60 (m, 1H), 7.56 (s, 1H), 7.29 (t, J = 8.0 Hz, 2H), 3.46 (s, 3H), 2.63 (s, 3H); ESI-MS (m/z) 423 (MH)⁺ |
| Example-24: N-(4-(4-Chloro-6-(4-methyl-5-oxo-4,5-dihydro-1,3,4-oxadiazol-2-yl)pyridin-2-yl)phenyl)-2,6-difluorobenzamide | 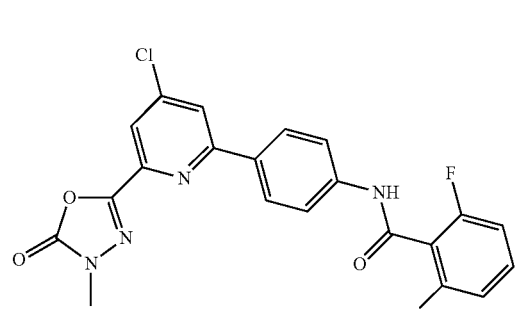 | ¹HNMR (400 MHz, DMSO) δ 11.07 (s, 1H), 8.32 (d, J = 1.5 Hz, 1H), 8.23 (d, J = 8.5 Hz, 2H), 7.87 (d, J = 1.5 Hz, 1H), 7.85 (d, J = 8.5 Hz, 2H), 7.63 (m, 1H), 7.28 (m, 2H), 3.47 (s, 3H); ESI-MS (m/z) 443, 445 [(MH)⁺, Cl ³⁵,³⁷]. |
| Example-25: N-(4-(4-Ethoxy-6-(4-methyl-5-oxo-4,5-dihydro-1,3,4-oxadiazol-2-yl)pyridin-2-yl)phenyl)-2,6-difluorobenzamide | 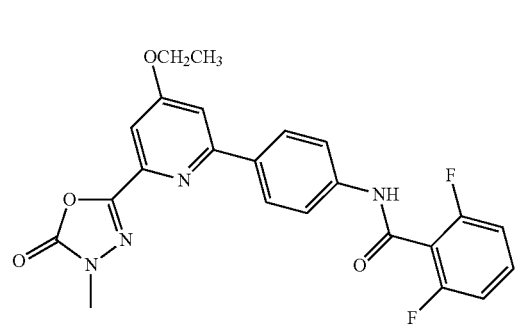 [SMILES: CCOc1cc(-c2ccc(NC(=O)c3c(F)cccc3F)cc2)nc(-c2nn(C)c(=O)o2)c1] | ¹HNMR (400 MHz, CDCl₃) δ 8.08 (d, J = 8.5 Hz, 2H), 7.79 (s, D₂O exchangeable, 1H), 7.78 (d, J = 8.5 Hz, 2H), 7.43-7.46 (m, 1H), 7.34 (d, J = 2.0 Hz, 1H), 7.30 (d, J = 2.0 Hz, 1H), 7.04 (t, J = 8.0 Hz, 2H), 4.23 (q, J = 7.0 Hz, 2H), 3.58 (s, 3H), 1.27 (t, J = 7.0 Hz, 3H); ESI-MS (m/z) 453 (MH)⁺ |

TABLE 3-continued

| Example No: IUPAC name | Structure | ¹HNMR/ESI-MS |
|---|---|---|
| Example-26: 2,6-Difluoro-N-(4-(2-(4-methyl-5-oxo-4,5-dihydro-1,3,4-oxadiazol-2-yl)pyridin-4-yl)phenyl)benzamide | 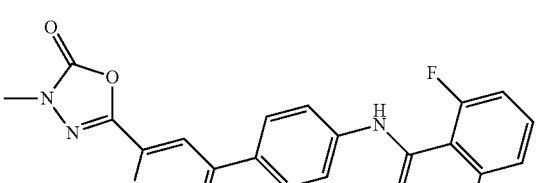 | ¹HNMR (400 MHz, CDCl₃) δ 8.79 (d, J = 5.0 Hz, 1H), 8.07 (d, J = 1.5 Hz, 1H), 7.84 (d, J = 8.5 Hz, 2H), 7.80 (s, 1H), 7.74 (d, J = 8.5 Hz, 2H), 7.66 (dd, J = 5.0, 1.5 Hz, 1H), 7.49-7.46 (m, 1H), 7.05 (t, J = 8.0 Hz, 2H), 3.59 (s, 3H); ESI-MS (m/z) 409 (MH)⁺ |
| Example-27: 2,6-Difluoro-N-(4-(4-methyl-6-(4-methyl-5-oxo-4,5-dihydro-1,3,4-oxadiazol-2-yl)pyridin-3-yl)phenyl)benzamide | 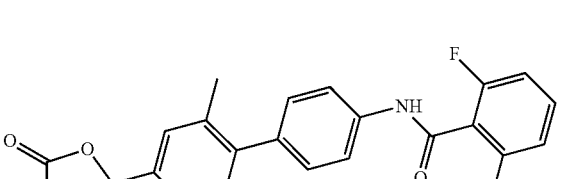 | ¹HNMR (400 MHz, CDCl₃) δ 8.56(s, 1H), 7.84 (s, 1H), 7.95 (d, J = 8.5 Hz, 2H), 7.76 (s, 1H), 7.45-7.49 (m, 1H), 7.38 (d, J = 8.5 Hz, 2H), 7.04(t, J = 8.0 Hz, 2H), 3.56 (s, 3H), 2.41 (s, 3H); ESI-MS (m/z) 423(MH)⁺ |

Example-28

N-(4-(2-Cyclopropyl-5-(4-methyl-5-oxo-4,5-dihydro-1,3,4-oxadiazol-2-yl)pyridin-3-yl)phenyl)-4-methyl-1,2,3-thiadiazole-5-carboxamide

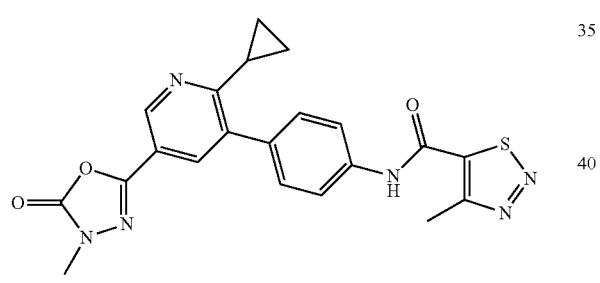

The title compound was prepared by the reacting Intermediate-3a with Intermediate-19 by following the general procedure described in Method C. ¹HNMR (400 MHz, CDCl₃) δ 8.87 (d, J=2.0 Hz, 1H), 7.88 (d, J=2.0 Hz, 1H), 7.78 (s, 1H), 7.73 (d, J=8.5 Hz, 2H), 7.52 (d, J=8.5 Hz, 2H), 3.51 (s, 3H), 3.02 (s, 3H), 2.15-2.11 (m, 1H), 1.28-1.24 (m, 2H), 1.02-0.9 (m, 2H); ESI-MS (m/z) 434 (M)⁺.

Examples 29-41a, 41b, 41c

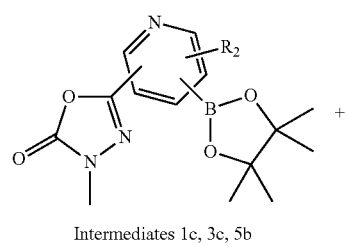

Intermediates 1c, 3c, 5b

+

Intermediates 20-22, 25, 26a 28-29, 34, 35

PdCl₂(PPh₃)₂
microwave or sealed tube or rb flask

Examples 29-41a, 41b, 41c

L = NHC(O) or NHCH₂
A = N or CH;

The below Examples mentioned in Table-4 were prepared by following the general procedure described in Method A, Method B or Method C by using appropriate intermediates.

TABLE 4

| Example No: IUPAC name | Structure | ¹HNMR/ESI-MS |
|---|---|---|
| Example-29: N-(4-(2-Ethyl-5-(4-methyl-5-oxo-4,5-dihydro-1,3,4-oxadiazol-2-yl)pyridin-3-yl)-3-methylphenyl)-2,6-difluorobenzamide. | 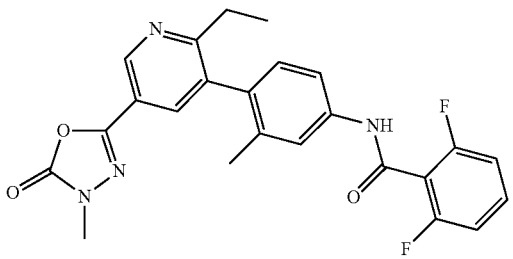 [SMILES: CCc1ncc(-c2nn(C)c(=O)o2)cc1-c1ccc(NC(=O)c2c(F)cccc2F)cc1C] | ¹HNMR (400 MHz, CDCl$_3$) δ 9.01 (d, J = 2.0 Hz, 1H), 7.83-7.82 (m, 2H), 7.67 (d, J = 2.0 Hz, 1H), 7.55 (dd, J = 8.5, 2.0 Hz, 1H), 7.49-7.41 (m, 1H), 7.13 (d, J = 8.5 Hz, 1H), 7.03 (t, J = 8.0 Hz, 2H), 3.52 (s, 3H), 2.65 (q, J = 7.0 Hz, 2H), 2.10 (s, 3H), 1.17 (t, J = 7.0 Hz, 3H); ESI-MS (m/z) 451 (MH)$^+$. |
| Example-30: N-(2'-ethyl-5'-(4-methyl-5-oxo-4,5-dihydro-1,3,4-oxadiazol-2-yl)-[3,3'-bipyridin]-6-yl)-2,6-difluorobenzamide | 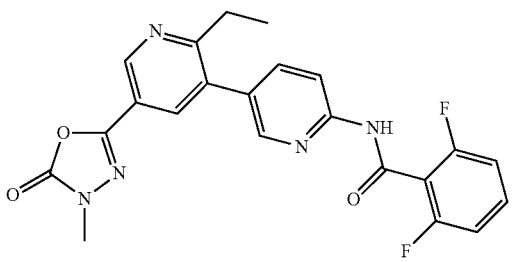 [SMILES: CCc1ncc(-c2nn(C)c(=O)o2)cc1-c1ccc(NC(=O)c2c(F)cccc2F)nc1] | ¹HNMR (400 MHz, CDCl$_3$) δ 9.05 (d, J = 2.5 Hz, 1H), 8.83 (s, 1H), 8.52 (d, J = 8.5 Hz, 1H), 8.20 (d, J = 2.5 Hz, 1H), 7.90 (d, J = 2.5 Hz, 7.78(dd, J = 8.5 & 2.5 Hz, 1H), 7.52-7.44 (m, 1H), 7.05 (t, J = 8.0 Hz, 2H), 3.54 (s, 3H), 2.84 (q, J = 7.0 Hz, 2H), 1.26 (t, J = 7.0 Hz, 3H); ESI-MS (m/z) 438 (MH)$^+$ |
| Example-31: N-(2'-ethyl-5'-(4-methyl-5-oxo-4,5-dihydro-1,3,4-oxadiazol-2-yl)-[2,3'-bipyridin]-5-yl)-2,6-difluorobenzamide | 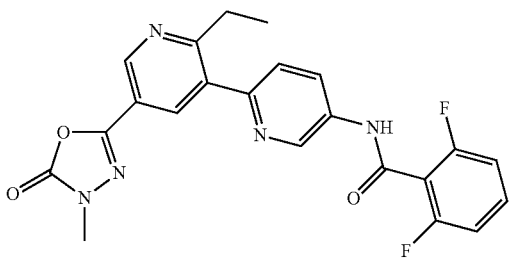 [SMILES: CCc1ncc(-c2nn(C)c(=O)o2)cc1-c1ccc(NC(=O)c2c(F)cccc2F)cn1] | ¹HNMR (400 MHz, CDCl$_3$) δ 9.04 (d, J = 2.0 Hz, 1H), 8.77 (d, J = 2.5 Hz, 1H), 8.49 (dd, J = 8.5 & 2.5 Hz, 1H), 8.11 (d, J = 2.0 Hz, 1H), 7.96 (s, 1H), 7.52-7.48 (m, 2H), 7.07 (t, J = 8.0 Hz, 2H), 3.53 (s, 3H), 2.99 (q, J = 7.0 Hz, 2H), 1.27 (t, J = 7.0 Hz, 3H); ESI-MS (m/z) 438 (MH)$^+$ |
| Example-32: N-(4-(2-Cyclopropyl-5-(4-methyl-5-oxo-4,5-dihydro-1,3,4-oxadiazol-2-yl)pyridin-3-yl)-3-methylphenyl)-2,6-difluorobenzamide | 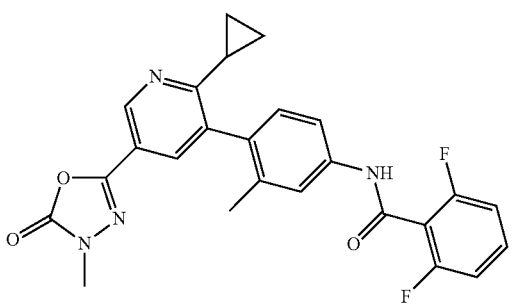 [SMILES: Cc1cc(NC(=O)c2c(F)cccc2F)ccc1-c1cc(-c2nn(C)c(=O)o2)cnc1C1CC1] | ¹HNMR (400 MHz, CDCl$_3$) δ 8.89 (d, J = 2.0 Hz, 1H), 7.81 (d, J = 2.0 Hz, 1H), 7.70-7.68 (m, 2H), 7.55 (dd, J = 8.0 & 2.0 Hz, 1H), 7.48-7.45 (m, 1H), 7.22 (d, J = 8.0 Hz, 1H), 7.04 (t, J = 8.0 Hz, 2H), 3.51 (s, 3H), 2.19 (s, 3H), 1.83-179 (m, 1H), 1.26-1.20 (m, 2H), 1.00-0.89 (m, 2H); ESI-MS (m/z) 462 (M)$^+$ |
| Example-33: N-(5-(2-Cyclopropyl-5-(4-methyl-5-oxo-4,5-dihydro-1,3,4-oxadiazol-2-yl)pyridin-3-yl)pyrazin-2-yl)-2,6-difluorobenzamide | 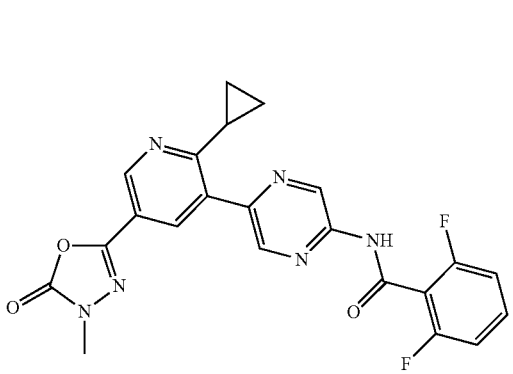 [SMILES: Cn1nc(-c2cnc(C3CC3)c(-c3cnc(NC(=O)c4c(F)cccc4F)cn3)c2)oc1=O] | ¹HNMR (400 MHz, CDCl$_3$) δ 9.84 (d, J = 1.0 Hz, 1H), 8.94 (d, J = 2.0 Hz, 1H), 8.65 (s, 1H), 8.56 (d, J = 1.0 Hz, 1H), 8.14 (d, J = 2.0 Hz, 1H), 7.55-7.48 (m, 1H), 7.10 (t, J = 8.0 Hz, 2H), 3.53 (s, 3H), 2.31-2.24 (m, 1H), 1.33-1.28 (m, 2), 1.10-1.07 (m, 2H); ESI-MS (m/z) 451 (MH)$^+$ |

TABLE 4-continued

| Example No: IUPAC name | Structure | ¹HNMR/ESI-MS |
|---|---|---|
| Example-34: 2-Chloro-N-(5-(2-cyclopropyl-5-(4-methyl-5-oxo-4,5-dihydro-1,3,4-oxadiazol-2-yl)pyridin-3-yl)pyrazin-2-yl)-6-fluorobenzamide | 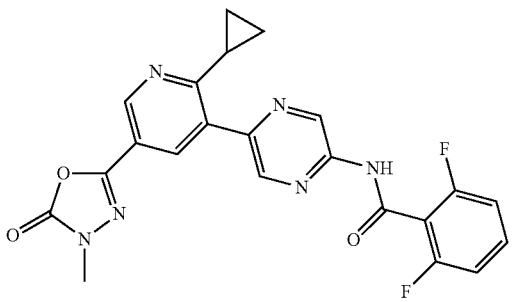 | ¹HNMR (400 MHz, CDCl$_3$) δ 9.85 (s, 1H), 8.95 (d, J = 2.0 Hz, 1H), 8.53 (s, 1H), 8.47 (s, 1H), 8.13 (d, J = 2.0 Hz, 1H), 7.47-7.41 (m, 1H), 7.33 (d, J = 8.0 Hz, 1H), 7.16 (t, J = 8.5 Hz, 1H), 3.53 (s, 3H), 2.32-2.27 (m, 1H), 1.33-1.26 (m, 2H), 1.06-1.06 (m, 2H); ESI-MS (m/z) 467, 469[(MH)$^+$, Cl $^{35,37}$] |
| Example-35: N-(2'-Cyclopropyl-5'-(4-methyl-5-oxo-4,5-dihydro-1,3,4-oxadiazol-2-yl)-[2,3'-bipyridin]-5-yl)-2,6-difluorobenzamide | 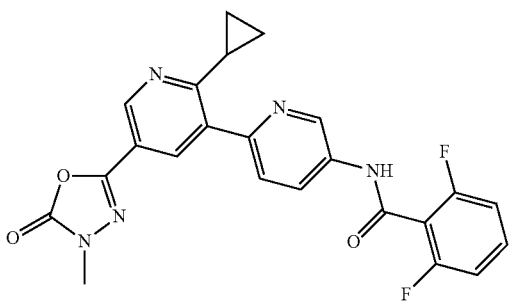 [SMILES: Cn1nc(-c2cnc(C3CC3)c(-c3ccc(NC(=O)c4c(F)cccc4F)cn3)c2)oc1=O] | ¹HNMR (400 MHz, CDCl$_3$) δ 8.91 (s, 1H), 8.79 (s, 1H), 8.51 (d, J = 8.0 Hz, 1H), 8.12 (s, 1H), 7.86 (s, 1H), 7.68 (d, J = 8.0 Hz, 1H), 7.52-7.49 (m, 1H), 7.08 (t, J = 8.0 Hz, 2H), 3.52 (s, 3H), 2.29-2.33 (m, 1H), 1.31-1.28 (m, 2H), 1.05-1.04 (m, 2H); ESI-MS (m/z) 450 (MH)$^+$ |
| Example-36: N-(2'-Cyclopropyl-5'-(4-methyl-5-oxo-4,5-dihydro-1,3,4-oxadiazol-2-yl)-[3,3'-bipyridin]-6-yl)-2,6-difluorobenzamide | 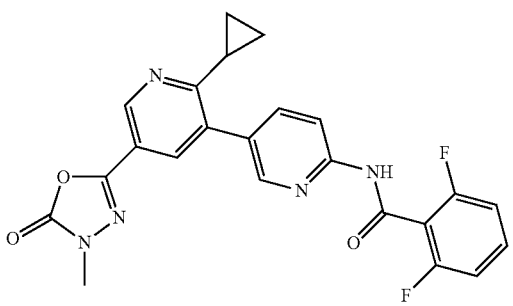 [SMILES: Cn1nc(-c2cnc(C3CC3)c(-c3ccc(NC(=O)c4c(F)cccc4F)nc3)c2)oc1=O] | ¹HNMR (400 MHz, CDCl$_3$) δ 9.01 (s, 1H), 8.91(d, J = 2.0 Hz, 1H), 8.55 (d, J = 8.0 Hz, 1H), 8.32 (d, J = 2.0 Hz, 1H), 7.95 (dd, J = 8.0 & 2.0 Hz, 1H), 7.87 (d, J = 2.0 Hz, 1H), 7.51-7.44 (m, 1H), 7.05 (t, J = 8.0 Hz, 2H), 3.53 (s, 3H), 2.07-2.02 (m, 1H), 1.31-1.27 (m, 2H), 1.06-1.02 (m, 2H); ESI-MS (m/z) 450 (MH)$^+$ |
| Example-37: 2,6-Difluoro-N-(5-(5-(4-methyl-5-oxo-4,5-dihydro-1,3,4-oxadiazol-2-yl)-2-(trifluoromethyl)pyridine-3-yl)pyrazin-2-yl)benzamide | 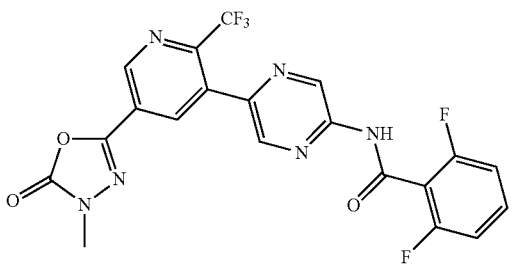 [SMILES: Cn1nc(-c2cnc(C(F)(F)F)c(-c3cnc(NC(=O)c4c(F)cccc4F)cn3)c2)oc1=O] | ¹HNMR (400 MHz, CDCl$_3$) δ 9.84 (d, J = 2.0 Hz, 1H), 9.22 (d, J = 2.0 Hz, 1H), 8.57 (s, 1H), 8.50 (d, J = 1.5 Hz, 1H), 8.40 (d, J = 1.5 Hz, 1H), 7.55-7.49 (m, 1H), 7.09(t, J = 8.5 Hz, 2H), 3.58 (s, 3H); ESI-MS (m/z) 479(MH)$^+$ |
| Example-38: 2,6-Difluoro-N-(5'-(4-methyl-5-oxo-4,5-dihydro-1,3,4-oxadiazol-2-yl)-2'-(trifluoromethyl)-[3,3'-bipyridin]-6-yl)benzamide | 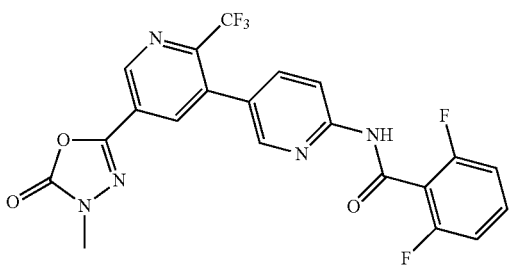 [SMILES: Cn1nc(-c2cnc(C(F)(F)F)c(-c3ccc(NC(=O)c4c(F)cccc4F)nc3)c2)oc1=O] | ¹HNMR (400 MHz, CDCl$_3$) δ 9.18 (d, J = 1.5 Hz, 1H), 8.71 (s, D$_2$O exchangeable, 1H), 8.53 (d, J = 8.5 Hz, 1H), 8.28 (d, J = 2.5 Hz, 1H), 8.14 (d, J = 1.5 Hz, 1H), 7.81 (dd, J = 8.5 & 2.5 Hz, 1H), 7.51-7.48 (m, 1H), 7.06 (t, J = 8.0 Hz, 2H), 3.58 (s, 3H); ESI-MS (m/z) 478(MH)$^+$ |

TABLE 4-continued

| Example No: IUPAC name | Structure | ¹HNMR/ESI-MS |
|---|---|---|
| Example-39: 2,6-Difluoro-N-(5'-(4-methyl-5-oxo-4,5-dihydro-1,3,4-oxadiazol-2-yl)-2'-(trifluoromethyl)-[2,3'-bipyridin]-5-yl)benzamide | 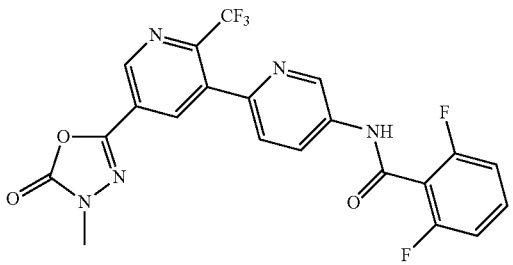 [SMILES: Cn1nc(-c2cnc(C(F)(F)F)c(-c3ccc(NC(=O)c4c(F)cccc4F)cn3)c2)oc1=O] | ¹HNMR (400 MHz, CDCl$_3$) δ 9.18 (s, 1H), 8.81 (s, 1H), 8.52 (d, J = 6.5 Hz, 1H), 8.37 (brs, 1H), 7.98 (s, 1H), 7.59-7.51 (m, 2H), 7.07 (t, J = 8.0 Hz, 2H), 3.57 (s, 3H); ESI-MS (m/z) 478(MH)$^+$ |
| Example-40: 5-(5-((2,6-Difluorobenzyl)amino)-2'-ethyl-[2,3'-bipyridin]-5'-yl)-3-methyl-1,3,4-oxadiazol-2(3H)-one | 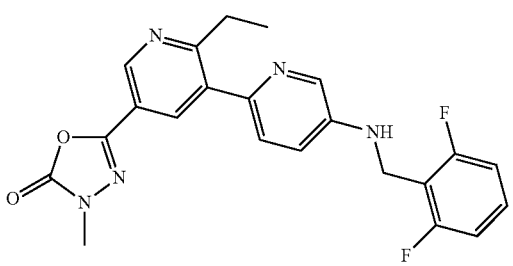 [SMILES: CCc1ncc(-c2nn(C)c(=O)o2)cc1-c1ccc(NCc2c(F)cccc2F)cn1] | ¹HNMR (400 MHz, DMSO-d$_6$) δ 8.85 (d, J = 2.0 Hz, 1H), 8.17 (d, J = 2.0 Hz, 1H), 7.98 (d, J = 2.0 Hz, 1H), 7.46-7.44 (m, 1H), 7.41 (d, J = 8.5 Hz, 1H), 7.18-7.13 (m, 3H), 6.64 (t, J = 5.5 Hz, 1H), 4.37 (d, J = 5.5 Hz, 2H), 3.42 (s, 3H), 2.93 (q, J = 7.5 Hz, 2H), 1.18 (t, J = 7.5 Hz, 3H) ESI-MS (m/z) 424 (MH)$^+$ |
| Example-41a: 5-(6'-((2,6-Difluorobenzyl)amino)-2-ethyl-[3,3'-bipyridin]-5-yl)-3-methyl-1,3,4-oxadiazol-2(3H)-one | 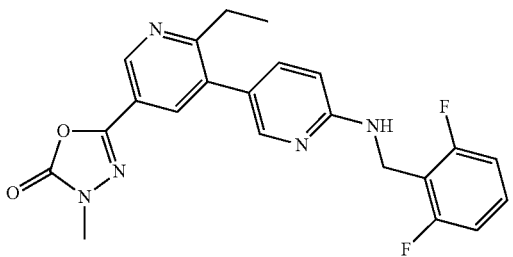 [SMILES: CCc1ncc(-c2nn(C)c(=O)o2)cc1-c1ccc(NCc2c(F)cccc2F)nc1] | ¹HNMR (400 MHz, CDCl$_3$) δ 8.97 (d, J = 2.0 Hz, 1H), 8.09 (d, J = 2.0 Hz, 1H), 7.87 (d, J = 2.0 Hz, 1H), 7.44 (dd, J = 6.5, 2.0 Hz, 1H), 7.32-7.24 (m, 1H), 7.24 (s, D$_2$O exchangeable, 1H), 6.95 (t, J = 4.0 Hz, 2H), 6.63 (d, J = 6.5 Hz, 1H), 4.68 (d, J = 6.0 Hz, 2H) 3.52 (s, 3H), 2.86 (q, J = 7.5 Hz, 2H), 1.26 (t, J = 7.5 Hz, 3H); ESI-MS (m/z) 424 (MH)$^+$ |
| Example-41b: N-(2'-Ethyl-4-methyl-5'-(4-methyl-5-oxo-4,5-dihydro-1,3,4-oxadiazol-2-yl)-[2,3'-bipyridin]-5-yl)-2,6-difluorobenzamide | 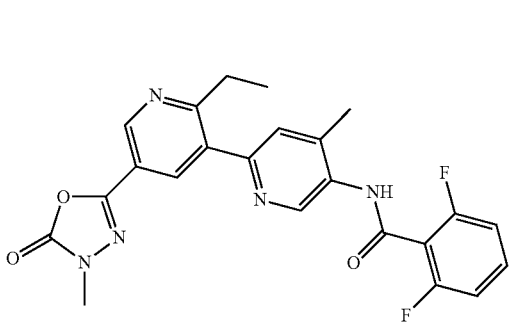 [SMILES: CCc1ncc(-c2nn(C)c(=O)o2)cc1-c1cc(C)c(NC(=O)c2c(F)cccc2F)cn1] | ¹HNMR (400 MHz, DMSO-d$_6$) δ 10.63 (s, 1H, D$_2$O exchangeable), 8.96 (d, J = 2.0 Hz, 1H), 8.72 (s, 1H), 8.09 (d, J = 2.0 Hz, 1H), 7.66 (s, 1H), 7.65-7.61 (m, 1H), 7.29 (t, J = 8.0 Hz, 2H), 3.43 (s, 3H), 2.94 (q, J = 7.0 Hz, 2H), 2.37 (s, 3H), 1.19 (t, J = 7.0 Hz, 3H); ESI-MS (m/z) 452 (MH)$^+$ |
| Example-41c: N-(2'-Ethyl-4-methyl-5'-(4-methyl-5-oxo-4,5-dihydro-1,3,4-oxadiazol-2-yl)-[3,3'-bipyridinl-6-yl)-2,6-difluorobenzamide | 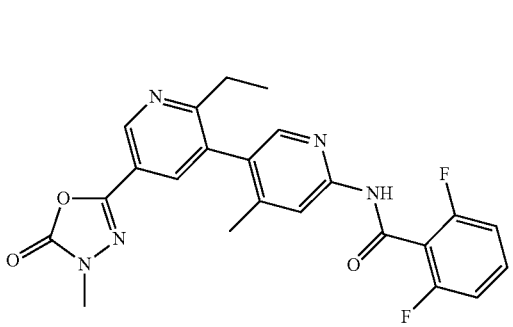 [SMILES: CCc1ncc(-c2nn(C)c(=O)o2)cc1-c1cnc(NC(=O)c2c(F)cccc2F)cc1C] | ¹HNMR (400 MHz, CDCl$_3$) δ 9.24 (s, 1H, D$_2$O exchangeable), 9.09 (d, J = 2.0 Hz, 1H), 8.50 (s, 1H), 8.01 (s, 1H), 7.86 (d, J = 2.0 Hz, 1H), , 7.53-7.45 (m, 1H), 7.06 (t, J = 8.0 Hz, 2H), 3.54 (s, 3H), 2.75-2.59 (m, 2H), 2.22 (s, 3H), 1.21 (t, J = 7.0 Hz, 3H); ESI-MS (m/z) 452 (MH)$^+$ |

Example-42

N-(2-Chloro-6-fluorophenyl)-5-(2-cyclopropyl-5-(4-methyl-5-oxo-4,5-dihydro-1,3,4-oxadiazol-2-yl)pyridin-3-yl)thiophene-2-carboxamide

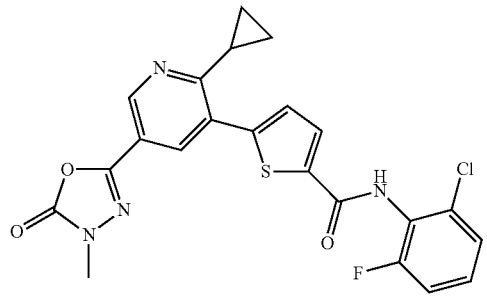 [SMILES: Cn1nc(-c2cnc(C3CC3)c(-c3ccc(C(=O)Nc4c(F)cccc4Cl)s3)c2)oc1=O]

The title compound was prepared by following the similar procedure as described in general procedure of Method-C by using Intermediate-3c and intermediate-30 $^1$HNMR (400 MHz, CDCl$_3$) δ 8.90 (d, J=2.0 Hz, 1H), 8.03 (d, J=2.0 Hz, 1H), 7.76 (d, J=3.5 Hz, 1H), 7.42 (s, 1H), 7.33-7.24 (m, 3H), 7.18-7.16 (m, 1H), 3.53 (s, 3H), 2.42-2.36 (m, 1H), 1.32-1.26 (m, 2H), 1.11-1.08 (m, 2H); ESI-MS (m/z) 470, 472 [(M)$^+$, Cl$^{35,37}$].

Example-43

5-(2-Cyclopropyl-5-(4-methyl-5-oxo-4,5-dihydro-1,3,4-oxadiazol-2-yl)pyridin-3-yl)-N-(3-methylpyridin-4-yl)thiophene-2-carboxamide

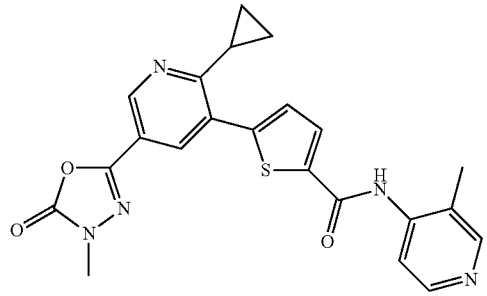 [SMILES: Cc1cnccc1NC(=O)c1ccc(-c2cc(-c3nn(C)c(=O)o3)cnc2C2CC2)s1]

The title compound was prepared by following the similar procedure as described in general procedure of Method-B by using Intermediate-3c and Intermediate-31. $^1$HNMR (400 MHz, CDCl$_3$) δ 8.92 (d, J=2.0 Hz, 1H), 8.48 (brs, 1H), 8.42 (brs, 1H), 8.20 (brs, 1H), 8.02 (d, J=2.0 Hz, 1H), 7.86 (bs, 1H), 7.75 (d, J=3.5 Hz, 1H), 7.33 (d, J=3.5 Hz, 1H), 3.53 (s, 3H), 2.42 (s, 3H), 2.38-2.32 (m, 1H), 1.33-1.30 (m, 2H), 1.11-1.07 (m, 2H); ESI-MS (m/z) 433 (M)$^+$.

Example-44

N-(2,6-Difluorophenyl)-5-(2-ethyl-5-(4-methyl-5-oxo-4,5-dihydro-1,3,4-oxadiazol-2-yl)pyridin-3-yl)furan-2-carboxamide

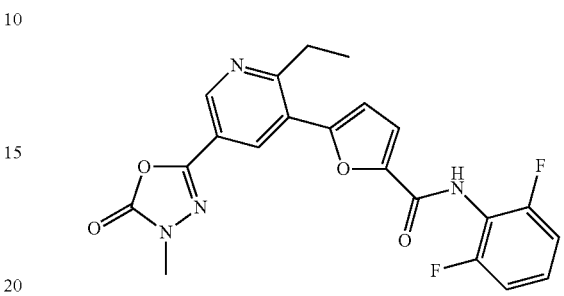

The title compound was prepared by following the similar procedure as described in general procedure of Method-C by using Intermediate-1c and Intermediate-32. $^1$HNMR (400 MHz, CDCl$_3$) δ 9.03 (d, J=2.5 Hz, 1H), 8.36 (d, J=2.5 Hz, 1H), 7.67 (s, D$_2$O exchangeable, 1H), 7.53 (d, J=3.5 Hz, 1H), 7.32-7.27 (m, 1H), 7.03 (t, J=8.0 Hz, 2H), 6.88 (d, J=3.5 Hz, 1H), 3.55 (s, 3H), 3.14 (q, J=7.5 Hz, 2H), 1.45 (t, J=7.5 Hz, 3H); ESI-MS (m/z) 427 (MH)$^+$.

Example-45

5-(2-Cyclopropyl-5-(4-methyl-5-oxo-4,5-dihydro-1,3,4-oxadiazol-2-yl)pyridin-3-yl)-N-(2,6-difluorophenyl)furan-2-carboxamide

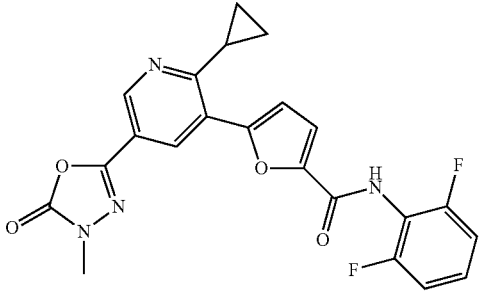 [SMILES: Cn1nc(-c2cnc(C3CC3)c(-c3ccc(C(=O)Nc4c(F)cccc4F)o3)c2)oc1=O]

The title compound was prepared by following the similar procedure as described in general procedure of Method C by using Intermediate-3c and Intermediate-32. $^1$HNMR (400 MHz, CDCl$_3$) δ 8.90 (d, J=2.5 Hz, 1H), 8.27 (d, J=2.5 Hz, 1H), 7.73 (s, D$_2$O exchangeable, 1H), 7.44 (d, J=3.5 Hz, 1H), 7.33-7.26 (m, 1H), 7.04 (t, J=8.0 Hz 2H) 7.01 (d, J=2.5 Hz, 1H), 3.54 (s, 3H), 2.49-2.43 (m, 1H), 1.36-1.32 (m, 2H), 1.17-1.13 (m, 2H); ESI-MS (m/z) 439 (MH)$^+$.

Example-46

N-(4-(2-Ethyl-5-(4-methyl-5-oxo-4,5-dihydro-1,3,4-oxadiazol-2-yl)pyridin-3-yl)phenyl)-3,5-difluoroisonicotinamide

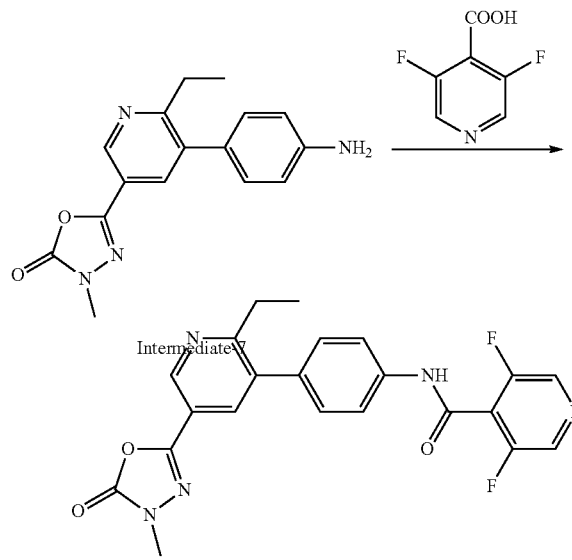

Example 46

To a solution of Intermediate-7 (200 mg, 0.67 mmol, 1.2 eq) and 3,5-difluoroisonicotinic acid (161 mg, 1.01 mmol, 1.5 eq) in DCM (20 mL) at RT was sequentially added EDC.HCl (194 mg, 1.01 mmol, 1.5 eq), HOBT (155 mg, 1.01 mmol, 1.5 eq) and triethylamine (0.18 mL, 1.35 mmol, 2.0 eq). The resulting solution was stirred at the same temperature for 24 h. Water (30 mL) was added to the reaction mixture followed by DCM (30 mL). The layers were separated and the aqueous layer was extracted with DCM (3×20 mL). The combined organic layers were washed with saturated sodium bicarbonate solution (20 mL), brine (20 mL) dried ($Na_2SO_4$) and filtered. The filtrate was concentrated under vacuum and the crude product was purified by flash column chromatography (silica gel, ethylacetate-hexanes system as eluent) to afford 40 mg (14%) of the desired product as a white solid. $^1$HNMR (400 MHz, $CDCl_3$) δ 9.00 (d, J=2.0 Hz, 1H), 8.53 (s, 2H), 8.00 (s, 1H), 7.92 (d, J=2.0 Hz, 1H), 7.76 (d, J=8.5 Hz, 2H), 7.38 (d, J=8.5 Hz, 2H), 3.52 (s, 3H), 2.86 (q, J=7.5 Hz, 2H), 1.24 (t, J=7.5 Hz, 3H); ESI-MS (m/z) 438 (MH)$^+$ The below Examples-47 to 52 given in Table-5 were prepared by following the similar procedure as described in Example-46 by using Intermediate-7 and appropriate acid intermediate.

TABLE 5

| Example No: IUPAC name | Structure | $^1$HNMR/ESI-MS |
|---|---|---|
| Example-47: N-(4-(2-Ethyl-5-(4-methyl-5-oxo-4,5-dihydro-1,3,4-oxadiazol-2-yl)pyridin-3-yl)phenyl)-2-fluoro-6-methylbenzamide | 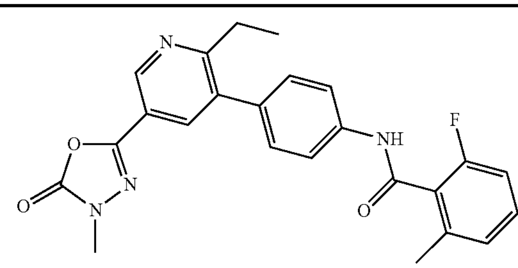 | $^1$HNMR (400 MHz, $CDCl_3$) δ 9.00 (d, J = 2.5 Hz, 1H), 7.92 (d, J = 2.5 Hz, 1H), 7.7 (d, J = 8.5 Hz, 2H), 7.69 (s, 1H), 7.35 (d, J = 8.5 Hz, 2H), 7.32-7.31 (m, 1H), 7.10 (d, J = 8.5 Hz, 1H), 7.02 (t, J = 8.0 Hz, 1H), 3.55 (s, 3H), 2.87 (q, J = 7.5 Hz, 2H), 2.52 (s, 3H), 1.25 (t, J = 7.5 Hz, 3H); ESI-MS (m/z) 433 (MH)$^+$ |
| Example-48: 2-Chloro-N-(4-(2-ethyl-5-(4-methyl-5-oxo-4,5-dihydro-1,3,4-oxadiazol-2-yl)pyridin-3-yl)phenyl)-6-fluorobenzamide | 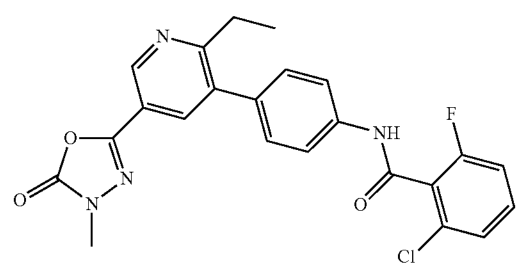 [SMILES: CCc1ncc(-c2nn(C)c(=O)o2)cc1-c1ccc(NC(=O)c2c(F)cccc2Cl)cc1] | $^1$HNMR (400 MHz, $CDCl_3$) δ 9.00 (d, J = 2.5 Hz, 1H), 7.92 (d, J = 2.5 Hz, 1H), 7.78 (d, J = 8.5 Hz, 1H), 7.68 (s, $D_2O$ exchangeable, 1H), 7.43-7.39 (m, 1H), 7.36 (d, J = 8.5 Hz, 2H), 7.31 (d, J = 8.0 Hz, 1H), 7.16-7.12 (m, 1H), 3.53 (s, 3H), 2.87 (q, J = 7.5 Hz, 2H), 1.26 (t, J = 7.5 Hz, 3H); ESI-MS (m/z) 453, 455 [(MH)$^+$, $Cl^{35,37}$] |
| Example-49: N-(4-(2-Ethyl-5-(4-methyl-5-oxo-4,5-dihydro-1,3,4-oxadiazol-2-yl)pyridin-3-yl)phenyl)-4-methyl-1,2,3-thiadiazole-5-carboxamide | 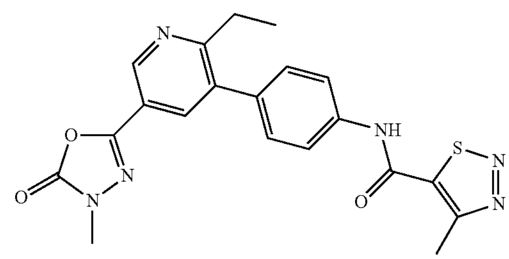 [SMILES: CCc1ncc(-c2nn(C)c(=O)o2)cc1-c1ccc(NC(=O)c2snnc2C)cc1] | $^1$HNMR (400 MHz, $CDCl_3$) δ 9.02 (d, J = 2.0 Hz, 1H), 7.92 (d, J = 2.0 Hz, 1H), 7.75 (s, $D_2O$ exchangeable, 1H), 7.72 (d, J = 8.5 Hz, 2H), 7.39 (d, J = 8.5 Hz, 2H), 3.53 (s, 3H), 3.02 (s, 3H), 2.86 (q, J = 7.5 Hz, 2H), 1.25 (t, J = 7.5 Hz, 3H); ESI-MS (m/z) 423(MH)$^+$ |

TABLE 5-continued

| Example No: IUPAC name | Structure | ¹HNMR/ESI-MS |
|---|---|---|
| Example-50: N-(4-(2-Ethyl-5-(4-methyl-5-oxo-4,5-dihydro-1,3,4-oxadiazol-2-yl)pyridin-3-yl)phenyl)-3,5-dimethylisoxazole-4-carboxamide | 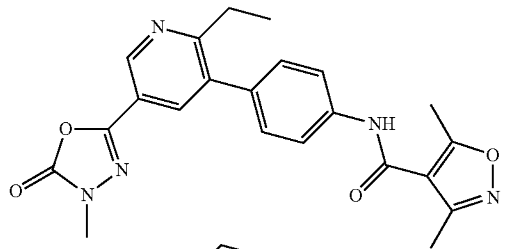 [SMILES: CCc1ncc(-c2nn(C)c(=O)o2)cc1-c1ccc(NC(=O)c2c(C)noc2C)cc1] | ¹HNMR (400 MHz, CDCl₃) δ 9.00 (d, J = 2.5 Hz, 1H), 7.91 (d, J = 2.5 Hz, 1H), 7.68 (d, J = 8.5 Hz, 2H), 7.43 (s, 1H), 7.35 (d, J = 8.5 Hz, 2H), 3.52 (s, 3H), 2.86 (q, J = 7.5 Hz, 2H), 2.72 (s, 3H), 2.55 (s, 3H), 1.24 (t, J = 7.5 Hz, 3H); ESI-MS (m/z) 420(MH)⁺ |
| Example-51: N-(4-(2-Ethyl-5-(4-methyl-5-oxo-4,5-dihydro-1,3,4-oxadiazol-2-yl)pyridin-3-yl) phenyl)-3-methylisonicotinamide | 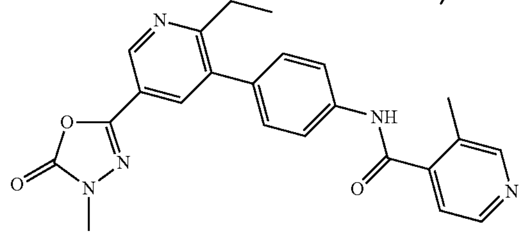 [SMILES: CCc1ncc(-c2nn(C)c(=O)o2)cc1-c1ccc(NC(=O)c2ccncc2C)cc1] | ¹HNMR (400 MHz, CDCl₃) δ 9.01 (d, J = 2.0 Hz, 1H), 8.59-8.57 (m, 2H), 7.92 (d, J = 2.0 Hz, 1H), 7.82 (s, 1H), 7.75 (d, J = 8.5 Hz, 2H), 7.40-7.38 (m, 3H), 3.53 (s, 3H), 2.87 (q, J = 7.5 Hz, 2H), 2.53 (s, 3H), 1.25 (t, J = 7.5 Hz, 3H); ESI-MS (m/z) 416 (MH)⁺ |

Example-52

N-(4-(5-(4,4-Dimethyl-5-oxo-4,5-dihydroisoxazol-3-yl)-2-ethylpyridin-3-yl)phenyl)-2,6-difluorobenzamide

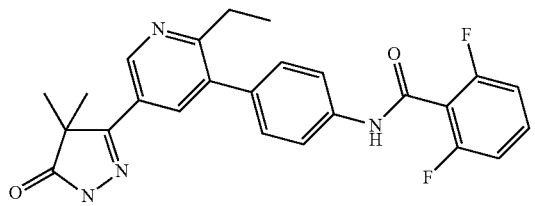 [SMILES: CCc1ncc(C2=NNC(=O)C2(C)C)cc1-c1ccc(NC(=O)c2c(F)cccc2F)cc1]

The title compound was prepared by the reaction of Intermediate-33 with Intermediate-16 by following the similar procedure as described in method B. ¹HNMR (400 MHz, DMSO-d₆) δ 10.99 (s, 1H, D₂O exchangeable), 8.96 (d, J=2.0 Hz, 1H), 7.92 (d, J=2.0 Hz, 1H), 7.83 (d, J=8.0 Hz, 2H), 7.64-7.59 (m, 1H), 7.46 (d, J=8.0 Hz, 2H), 7.28 (t, J=8.0 Hz, 2H), 2.82 (q, J=7.0 Hz, 2H), 1.58 (s, 6H), 1.20 (t, J=7.0 Hz, 3H); ESI-MS (m/z) 450 (MH)⁺

Example-53

2,6-Difluoro-N-(5-(2-ethyl-5-(4-methyl-5-oxo-4,5-dihydro-1,3,4-oxadiazol-2-yl)pyridin-3-yl)pyrazin-2-yl)benzamide

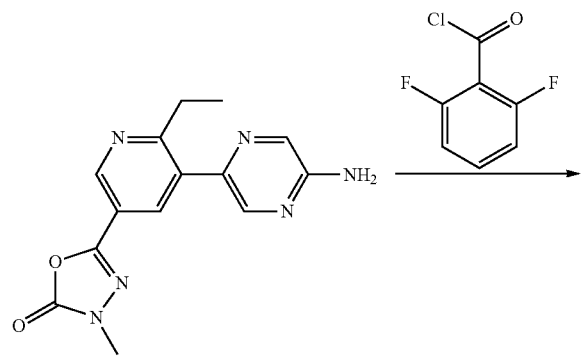

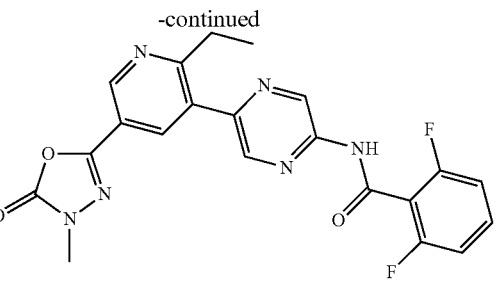

Example 53

To a 0° C. cooled and stirred solution of 2,6-difluorobenzoyl chloride (118 mg, 0.67 mmol, 1.0 eq) in DCM (2 mL) was added drop-wise a solution of Intermediate-1b, (200 mg, 0.67 mmol, 1.0 eq) in DCM (2 mL) followed by pyridine (63.6 mg, 0.80 mmol, 1.2 eq). The resulting mixture was stirred at RT overnight. The reaction was diluted with DCM (10 mL), and washed with water (5 mL), brine (5 mL), dried (Na₂SO₄) and filtered. The filtrate was concentrated under vacuum and the crude product was purified by flash column chromatography (silica gel, ethyl acetate-hexane system as eluent) to afford 45 mg (15%) of the example-53 as a white solid. ¹HNMR (400 MHz, CDCl₃) δ 9.82(d, J=2.0 Hz, 1H), 9.08 (d, J=2.0 Hz, 1H), 8.56 (s, 1H), 8.44 (d, J=2.0 Hz, 1H), 8.14 (d, J=2.0 Hz, 1H), 7.53 (m, 1H), 7.09 (t, J=8.0 Hz, 2H), 3.54 (s, 3H), 2.99 (q, J=7.5 Hz, 2H), 1.31 (t, J=7.5 Hz, 3H); ESI-MS (m/z) 439 (MH)⁺.

Example-54

2-Chloro-N-(5-(2-ethyl-5-(4-methyl-5-oxo-4,5-dihydro-1,3,4-oxadiazol-2-yl)pyridin-3-yl)pyrazin-2-yl)-6-fluorobenzamide

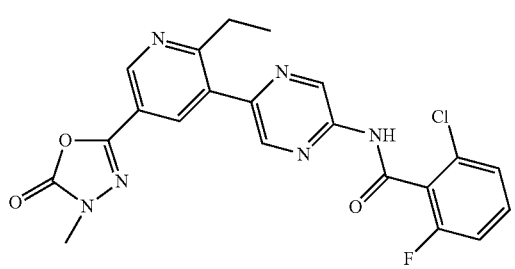 [SMILES: CCc1ncc(-c2nn(C)c(=O)o2)cc1-c1cnc(NC(=O)c2c(F)cccc2Cl)cn1]

The title compound was prepared by following the similar procedure as described in Example-53 by using Intermediate-1b and 2-chloro-6-fluorobenzoyl chloride. ¹HNMR (400 MHz, CDCl₃) δ 9.83 (s, 1H), 9.08 (s, 1H), 8.62 (s, D₂O exchangeable, 1H), 8.35 (s, 1H), 8.11 (s, 1H), 7.45 (m, 1H) 7.33 (d, J=8.0 Hz, 1H), 7.16 (t, J=8.0 Hz, 1H), 3.55 (s, 3H), 3.00 (q, J=7.5 Hz, 2H), 1.31 (t, J=7.5 Hz, 3H); ESI-MS (m/z) 455, 457 [(MH)⁺, Cl³⁵,³⁷]

Example-55

2,6-Difluoro-N-(5-(2-methyl-5-(4-methyl-5-oxo-4,5-dihydro-1,3,4-oxadiazol-2-yl)pyridin-3-yl)pyrazin-2-yl)benzamide

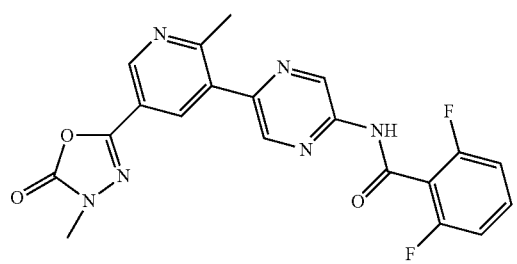 [SMILES: Cc1ncc(-c2nn(C)c(=O)o2)cc1-c1cnc(NC(=O)c2c(F)cccc2F)cn1]

The title compound was prepared by following the similar procedure as described in Example-53 by using Intermediate-2 band 2,6-difluorobenzoyl chloride followed by Boc deprotection using trifluoroacitic acid. ¹HNMR (400 MHz, CDCl₃) δ 9.82 (s, 1H), 9.03 (s, 1H), 8.67 (s, 1H), 8.45 (s, 1H), 8.18 (s 1H), 7.52 (m, 1H), 7.08 (t, J=8.0, 2H), 3.56 (s, 3H), 2.74 (s, 3H); ESI-MS (m/z) 425 (MH)⁺

Example-56

2,6-Difluoro-N-(5-(5-(4-methyl-5-oxo-4,5-dihydro-1,3,4-oxadiazol-2-yl)-2-(methylamino)pyridin-3-yl)pyrazin-2-yl)benzamide

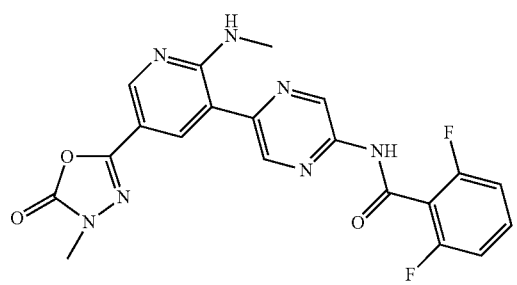 [SMILES: CNc1ncc(-c2nn(C)c(=O)o2)cc1-c1cnc(NC(=O)c2c(F)cccc2F)cn1]

The title compound was prepared by following the similar procedure as described in Example-53 by using Intermediate-6c and 2,6-difluorobenzoyl chloride.

¹HNMR (400 MHz, CDCl₃) δ 9.68 (s, 1H), 9.20 (q, J=4.5 Hz, 1H), 8.77 (d, J=2.0 Hz, 1H), 8.69 (d, J=2.0 Hz, 1H), 8.64 (s, 1H), 8.24 (s, 1H), 7.50 (m, 1H), 7.08 (t, J=8.0 Hz, 2H), 3.51 (s, 3H), 3.18 (d, J=4.5 Hz, 3H); ESI-MS (m/z) 440 (MH)⁺

General Procedure for the Synthesis of Example 57-63

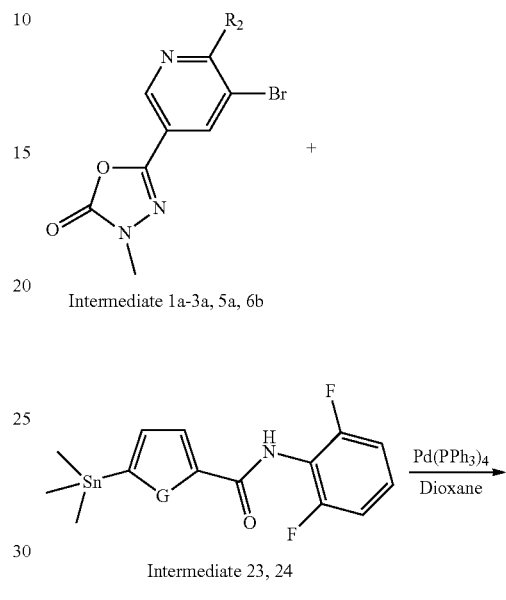

Intermediate 1a-3a, 5a, 6b

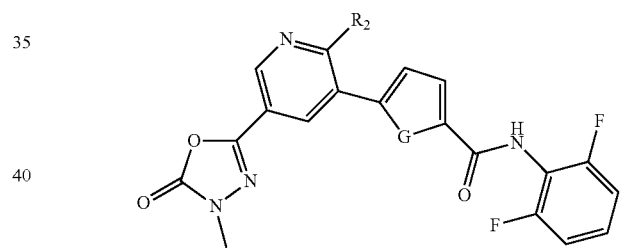

Intermediate 23, 24

Examples 57-63

G = S, NMe

To a nitrogen purged and stirred solution of any one of bromo Intermediate 1a, 2a, 3a, 5a, or 6b (1.0 eq) in dioxane (10 mL), any one of stananne derivative of Intermediate-23 or Intermediate-24 (1.0 eq) and Pd(PPh₃)₄ (0.05 eq) were sequentially added. The resulting mixture was thoroughly deoxygenated by purging nitrogen gas for 15 min and then heated to 130° C. and maintained for 30 min in microwave (Biotage). The reaction mixture was cooled to RT and filtered through celite. The filtrate was concentrated under vacuum and the crude product was purified by flash column chromatography (silica gel, ethyl acetate-hexanes system as eluent) to afford the desired product as a solid. The Examples 57-63 given in Table-6 were prepared by following this procedure using appropriate intermediates.

TABLE 6

| Example No: IUPAC name | Structure | ¹HNMR/ESI-MS |
|---|---|---|
| Example-57: N-(2,6-Difluorophenyl)-5-(2-ethyl-5-(4-methyl-5-oxo-4,5-dihydro-1,3,4-oxadiazol-2-yl)pyridin-3-yl)thiophene-2-carboxamide | 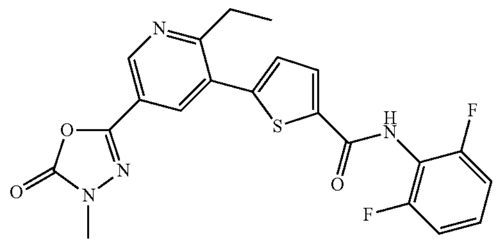 [SMILES: CCc1ncc(-c2nn(C)c(=O)o2)cc1-c1ccc(C(=O)Nc2c(F)cccc2F)s1] | ¹HNMR (400 MHz, CDCl$_3$) δ 9.03 (d, J = 2.0 Hz, 1H), 8.08 (d, J = 2.0 Hz, 1H), 7.73 (d, J = 3.5 Hz, 1H), 7.34 (s, 1H), 7.32-7.24 (m, 1H), 7.18 (d, J = 3.5 Hz, 1H), 7.03(t, J = 8.0 Hz, 2H), 3.50 (s, 3H), 3.03 (q, J = 7.0 Hz, 2H), 1.32 (t, J = 7.0 Hz, 3H); ESI-MS (m/z) 443 (MH)$^+$ |
| Example-58: N-(2,6-Difluorophenyl)-5-(2-methyl-5-(4-methyl-5-oxo-4,5-dihydro-1,3,4-oxadiazol-2-yl)pyridin-3-yl)thiophene-2-carboxamide | 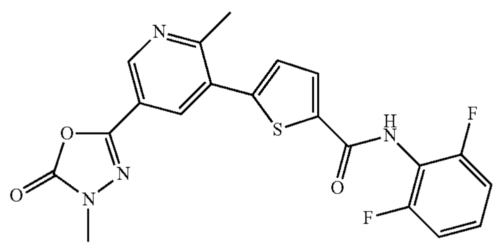 [SMILES: Cc1ncc(-c2nn(C)c(=O)o2)cc1-c1ccc(C(=O)Nc2c(F)cccc2F)s1] | ¹HNMR (400 MHz, CDCl$_3$) δ 8.98 (d, J = 2.0 Hz, 1H), 8.11 (d, J = 2.0 Hz, 1H), 7.74 (d, J = 4.0 Hz, 1H), 7.38 (s, 1H), 7.28 (m, 1H), 7.22 (d, J = 4.0 Hz, 1H), 7.03 (t, J = 8.0 Hz, 2H), 3.52 (s, 3H), 2.77 (s, 3H); ESI-MS (m/z) 429 (MH)$^+$. |
| Example-59: 5-(2-Cyclopropyl-5-(4-methyl-5-oxo-4,5-dihydro-1,3,4-oxadiazol-2-yl)pyridin-3-yl)-N-(2,6-difluorophenyl)thiophene-2-carboxamide | 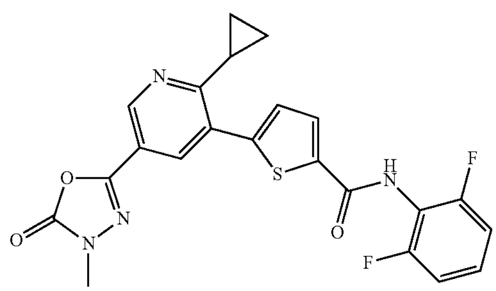 [SMILES: Cn1nc(-c2cnc(C3CC3)c(-c3ccc(C(=O)Nc4c(F)cccc4F)s3)c2)oc1=O] | ¹HNMR (400 MHz, CDCl$_3$) δ 8.89 (d, J = 2.0 Hz, 1H), 8.02 (d, J = 2.0 Hz, 1H), 7.74 (d, J = 3.5 Hz, 1H), 7.33 (s, 1H), 7.32-7.24 (m, 2H), 7.01 (t, J = 8.5 Hz, 2H), 3.53 (s, 3H), 2.41-2.35 (m, 1H), 1.32-1.26 (m, 2H), 1.10-1.06 (m, 2H); ESI-MS (m/z) 455 (MH)$^+$ |
| Example-60: N-(2,6-Difluorophenyl)-5-(5-(4-methyl-5-oxo-4,5-dihydro-1,3,4-oxadiazol-2-yl)-2-(trifluoromethyl)pyridin-3-yl)thiophene-2-carboxamide | 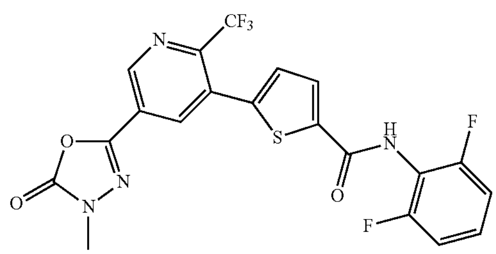 [SMILES: Cn1nc(-c2cnc(C(F)(F)F)c(-c3ccc(C(=O)Nc4c(F)cccc4F)s3)c2)oc1=O] | ¹HNMR (400 MHz, CDCl$_3$) δ 9.16 (d, J = 2.0 Hz, 1H), 8.29 (d, J = 2.0 Hz, 1H), 7.71 (d, J = 4.0 Hz, 1H), 7.39 (s, D$_2$O exchangeable, 1H), 7.29 (m, 1H), 7.26 (d, J = 4.0 Hz, 1H), 7.03 (t, J = 8.0 Hz 2H), 3.60 (s, 3H); ESI-MS (m/z) 483(MH)$^+$ |
| Example-61: N-(2,6-Difluorophenyl)-5-(5-(4-methyl-5-oxo-4,5-dihydro-1,3,4-oxadiazol-2-yl)-2-(methylamino)pyridin-3-yl)thiophene-2-carboxamide | 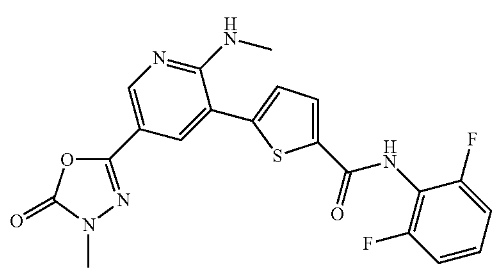 [SMILES: CNc1ncc(-c2nn(C)c(=O)o2)cc1-c1ccc(C(=O)Nc2c(F)cccc2F)s1] | ¹HNMR (400 MHz, DMSO) δ10.29 (s, D$_2$O exchangeable, 1H), 8.50 (d, J = 1.5 Hz, 1H), 8.05 (d, J = 1.5 Hz, 1H), 7.70 (s, 1H), 7.47-7.42 (m, 2H), 7.24 (t, J = 8.0 Hz, 2H), 6.97 (q, J = 4.5 Hz, D$_2$O exchangeable, 1H), 3.35 (s, 3H), 2.88 (d, J = 4.5 Hz, 3H); ESI-MS (m/z) 444 (MH)$^+$ |
| Example-62: N-(2,6-Difluorophenyl)-1-methyl-5-(2-methyl-5-(4-methyl-5-oxo-4,5-dihydro-1,3,4-oxadiazol-2-yl)pyridin-3-yl)-1H-pyrrole-2-carboxamide | 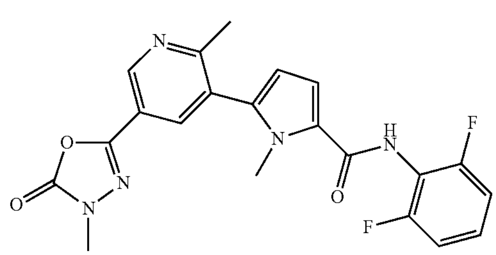 [SMILES: Cc1ncc(-c2nn(C)c(=O)o2)cc1-c1ccc(C(=O)Nc2c(F)cccc2F)n1C] | ¹HNMR (400 MHz, CDCl$_3$) δ 9.02 (d, J = 2.5 Hz, 1H), 7.97 (d, J = 2.5 Hz, 1H), 7.31 (s, D$_2$O exchangeable, 1H), 7.23 (m, 1H), 7.01 (t, J = 8.0 Hz, 2H), 6.94 (d, J = 4.5 Hz, 1H), 6.23 (d, J = 4.5 Hz, 1H), 3.73 (s, 3H), 3.53 (s, 3H), 2.51(s, 3H); ESI-MS (m/z) 426(MH)$^+$ |

TABLE 6-continued

| Example No: IUPAC name | Structure | ¹HNMR/ESI-MS |
|---|---|---|
| Example-63: N-(2,6-Difluorophenyl)-5-(2-ethyl-5-(4-methyl-5-oxo-4,5-dihydro-1,3,4-oxadiazol-2-yl)pyridin-3-yl)-1-methyl-1H-pyrrole-2-carboxamide | 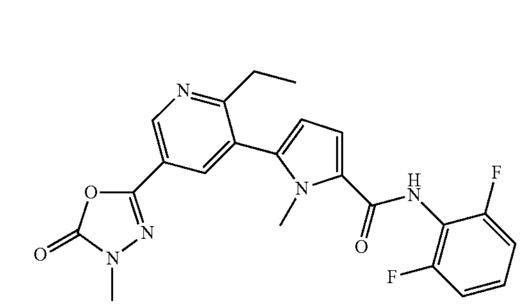 [SMILES: CCc1ncc(-c2nn(C)c(=O)o2)cc1-c1ccc(C(=O)Nc2c(F)cccc2F)n1C] | ¹HNMR (400 MHz, CDCl$_3$) δ 9.07 (d, J = 1.5 Hz, 1H), 7.96 (d, J = 1.5 Hz, 1H), 7.27 (s, 1H), 7.24-7.21 (m, 1H), 7.02 (t, J = 8.0 Hz, 2H), 6.94 (d, J = 4.0 Hz, 1H), 6.23 (d, J = 4.0 Hz, 1H), 3.72 (s, 3H), 3.53 (s, 3H), 2.77 (q, J = 7.5 Hz, 2H), 1.24 (t, J = 7.5 Hz, 3H); ESI-MS (m/z) 440 (MH)$^+$ |

Example-64

N-(4-(4-Ethyl-6-(4-methyl-5-oxo-4,5-dihydro-1,3,4-oxadiazol-2-yl)pyridin-2-yl)phenyl)-2,6-difluorobenzamide To a nitrogen purged and stirred solution of Example-24 (100 mg, 0.226 mmol) and ethylboronic acid (0.025 g, 0.339 mmol) in dioxane (5 ml) in a sealed tube, potassium carbonate (94 mg, 0.67 mmol) and Pd(Ph$_3$P)$_4$ (13 mg, 0.011 mmol) were sequentially added. The resulting mixture was thoroughly deoxygenated by nitrogen gas for 15 min and then heated to 130° C. and maintained for 16 h. The reaction mixture was cooled to RT and filtered through celite. The filtrate was concentrated under vacuum and the crude product was purified by flash column chromatography (silica gel, ethyl acetate-hexanes system as eluent) to afford 24 mg (24%) of the desired product as a white solid. ¹HNMR (400 MHz, CDCl$_3$) δ 7.90 (d, J=1.5 Hz, 1H), 7.83 (d, J=8.5 Hz, 2H), 7.79 (s, 1H), 7.73 (d, J=8.5 Hz, 2H), 7.53 (d, J=1.5 Hz, 1H), 7.51-7.43 (m, 1H), 7.05 (t, J=8.0 Hz, 2H), 3.59 (s, 3H), 3.00 (q, J=7.5 Hz, 2H), 1.40 (t, J=7.5 Hz, 3H); ESI-MS (m/z) 437 (MH)$^+$.

Example-65

N-(4-(3-Ethyl-5-(4-methyl-5-oxo-4,5-dihydro-1,3,4-oxadiazol-2-yl)pyridin-2-yl)phenyl)-2,6-difluorobenzamide -continued

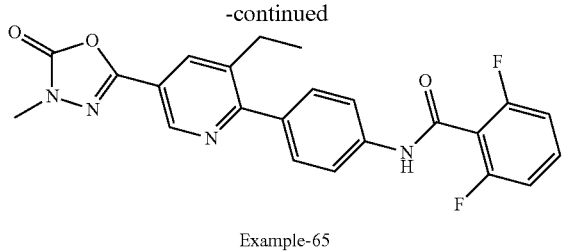

Example-65

Step-1: Ethyl-5-bromo-6-(4-(2,6-difluorobenzamido)phenyl)nicotinate: To a nitrogen gas purged solution of ethyl-5,6-dibromonicotinate (5.0 g, 16.18 mmol, prepared by following the procedure described in WO2011024004) in dioxane (50 mL), in a sealed tube was added Intermediate-16 (5.81 g, 16.18 mmol) and potassium carbonate (4.47 g, 32.4 mmol). The resulting mixture was thoroughly deoxygenated by purging nitrogen gas for 15 min and then tetrakis(triphenylphosphine)palladium(0) (0.93 g, 0.81 mmol) was added to the above mixture. The resulting mixture was then heated to 120° C. and maintained for 16 h. The reaction was cooled to RT and filtered through celite. The filtrate was concentrated under vacuum and the crude product was purified by flash column chromatography (silica gel, ethyl acetate-hexanes system as eluent) to afford 3.20 g (43%) of the title compound as white solid. $^1$HNMR (400 MHz, DMSO-$d_6$) δ 11.05 (s, $D_2O$ exchangeable, 1H), 9.11 (d, J=2.0 Hz, 1H), 8.55 (d, J=2.0 Hz, 1H), 7.84 (d, J=8.5 Hz, 2H), 7.74 (d, J=8.5 Hz, 2H), 7.62-7.59 (m, 1H), 7.28 (t, J=8.0 Hz, 2H), 4.38 (q, J=7.0 Hz, 2H), 1.35 (t, J=7.0 Hz, 3H); ESI-MS (m/z) 461, 463 [(MH)$^+$, Br$^{79,81}$].

Step-2: 5-Bromo-6-(4-(2,6-difluorobenzamido)phenyl)nicotinic acid: To a 0° C. cooled solution of step-1 intermediate (1.0 g, 2.62 mmol) in ethanol (20 mL) was added a solution of sodium hydroxide (0.315 g, 7.87 mmol) in water (10 mL) and stirred the reaction at RT for 4 h. The solvent was evaporated under vacuum and the residue was taken in water (10 mL), acidified with 10% HCl (2 mL). The precipitated solid was filtered and dried under vacuum to yield 0.88 g (93%) of the title compound as a white solid. $^1$HNMR (400 MHz, DMSO-$d_6$) δ 11.03 (s, $D_2O$ exchangeable, 1H), 9.03 (d, J=1.5 Hz, 1H), 8.45 (d, J=1.5 Hz, 1H), 7.81 (d, J=8.5 Hz, 2H), 7.72 (d, J=8.5 Hz, 2H), 7.63-7.57 (m, 1H), 7.22 (t, J=8.0 Hz, 2H); ESI-MS (m/z) 431, 432 [(MH)$^+$, Br$^{79,81}$].

Step-3: N-(4-(3-bromo-5-(hydrazinecarbonyl)pyridin-2-yl)phenyl)-2,6-difluorobenzamide: To a stirred solution of step-2 intermediate (200 mg, 0.46 mmol), in DCM (5 mL) EDC.HCl (133 mg, 0.69 mmol), HOBT (0.031 g, 0.231 mmol) and hydrazine hydrate (22 µL, 0.693 mmol) were successively added. After stirring at RT for 16 h, water (10 mL) was added to the reaction followed by DCM (20 mL). The layers were separated and aqueous layer was extracted with DCM (3×10 mL). The combined organic layers were washed with bine (20 mL), dried ($Na_2SO_4$) and filtered. The filtrate was concentrated under vacuum to afford 180 mg (87%) of the title compound as a white solid. $^1$HNMR (400 MHz, DMSO-$d_6$) δ 11.03 (s, $D_2O$ exchangeable, 1H), 10.11 (s, $D_2O$, exchangeable, 1H), 9.02 (d, J=2.0 Hz, 1H), 8.52 (d, J=2.0 Hz, 1H), 7.82 (d, J=8.5 Hz, 2H), 7.72 (d, J=8.5 Hz, 2H), 7.65-7.58 (m, 1H), 7.28 (t, J=8.0 Hz, 2H), 4.64 (brs, $D_2O$ exchangeable, 2H); ESI-MS (m/z) 446, 448 [(MH)$^+$, Br$^{79,81}$].

Step-4: N-(4-(3-Bromo-5-(4-methyl-5-oxo-4,5-dihydro-1,3,4-oxadiazol-2-yl)pyridin-2-yl)phenyl)-2,6-difluorobenzamide: The title compound was prepared from step-3 intermediate by following the similar procedure as described in step-3 and step-4 of Intermediate-1a. $^1$HNMR (400 MHz, DMSO-$d_6$) δ 11.05 (s, $D_2O$ exchangeable, 1H), 9.11 (d, J=1.5 Hz, 1H), 8.56 (d, J=1.5 Hz, 1H), 7.82 (d, J=8.0 Hz, 2H), 7.71 (d, J=8.0 Hz, 2H), 7.65-7.57 (m, 1H), 7.28 (t, J=8.0 Hz, 2H), 3.92 (s, 3H); (ESI-MS (m/z) 488, 490 [(MH)$^+$ Br$^{79,81}$].

Step-5: N-(4-(3-Ethyl-5-(4-methyl-5-oxo-4,5-dihydro-1,3,4-oxadiazol-2-yl)pyridin-2-yl)phenyl)-2,6-difluorobenzamide: To a nitrogen gas purged solution of step-4 intermediate (105 mg, 0.21 mmol) in dioxane (2 mL) in a microwave tube was added ethylboronic acid (19 mg, 0.26 mmol) and potassium carbonate (60 mg, 0.43 mmol). The resulting mixture was thoroughly deoxygenated by purging nitrogen gas for 15 min and then tetrakis(triphenylphosphine)palladium(0) (12 mg, 10.77 µmol) was added. The reaction mixture was heated at 100° C. for 2 h in a microwave reactor. The reaction mixture was cooled to RT diluted with dioxane (5 mL) and filtered through celite. The filtrate was concentrated under vacuum and the crude product was purified by flash column chromatography (silica gel, ethyl acetate-hexanes system as eluent) to afford 25 mg (26%) the title compound as a white solid. $^1$HNMR (400 MHz, CDCl$_3$) δ 8.95 (d, J=2.0 Hz, 1H), 8.06 (d, J=2.0 Hz, 1H), 7.84 (s, $D_2O$ exchangeable, 1H), 7.75 (d, J=8.0 Hz, 2H), 7.55 (d, J=8.0 Hz, 2H), 7.50-7.42 (m, 1H), 7.03 (t, J=8.0 Hz, 2H), 3.56 (s, 3H), 2.80 (q, J=7.5 Hz, 2H), 1.23 (t, J=7.5 Hz, 3H); ESI-MS (m/z) 437 (MH)$^+$ Example-66

N-(4-(3-Cyclopropyl-5-(4-methyl-5-oxo-4,5-dihydro-1,3,4-oxadiazol-2-yl)pyridin-2-yl)phenyl)-2,6-difluorobenzamide

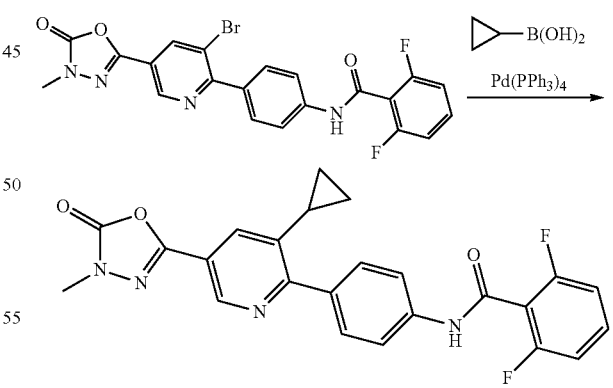

Example 66

The title compound was prepared by following the similar procedure as described in step-5 of Example-65 using step-4 intermediate of Example-65 and cyclopropylboronic acid. $^1$HNMR (400 MHz, CDCl$_3$) δ 8.93 (d, J=2.0 Hz, 1H), 7.78-7.76 (m, 4H), 7.75 (s, $D_2O$ exchangeable, 1H), 7.66 (d, J=2.0 Hz, 1H), 7.49-7.45 (m, 1H), 7.05 (t, J=8.0 Hz, 2H), 3.55 (s, 3H), 2.12-2.08 (m, 1H), 1.10-1.05 (m, 2H), 0.84-0.80 (m, 2H); ESI-MS (m/z) 449 (MH)+

Example-67

N-(4-(5-Cyclopropyl-3-(4-methyl-5-oxo-4,5-dihydro-1,3,4-oxadiazol-2-yl)pyridin-2-yl)phenyl)-2,6-difluorobenzamide

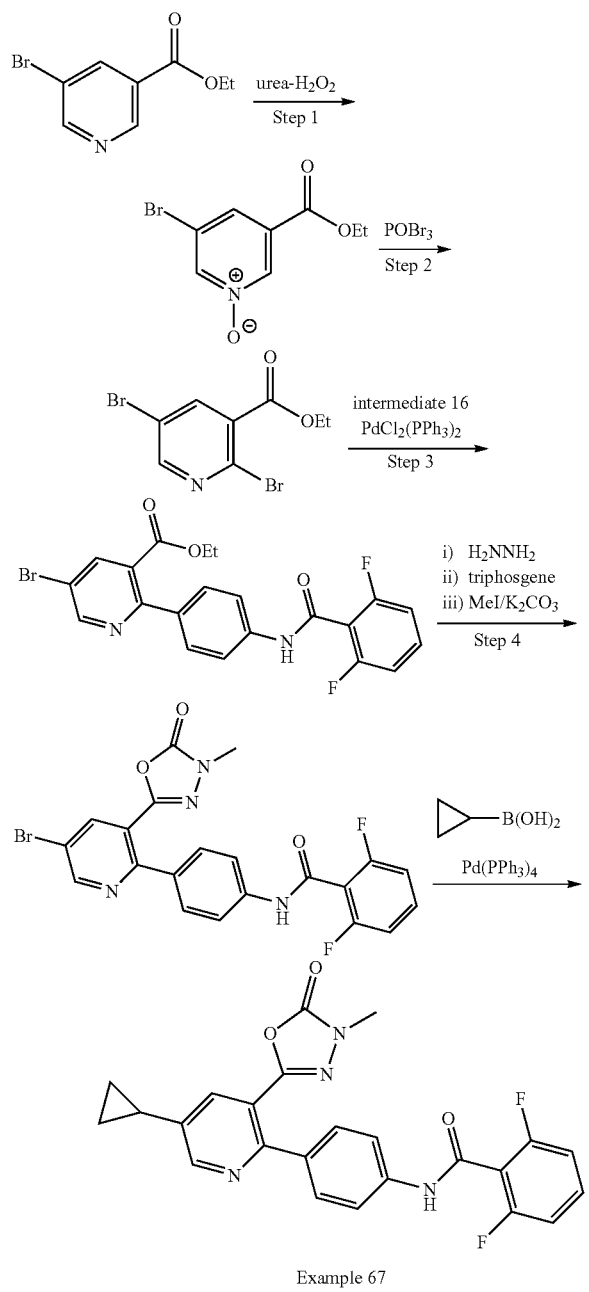

Example 67

Step-1:3-Bromo-5-(ethoxycarbonyl)pyridine-1-oxide: To a stirred solution of ethyl 5-bromonicotinate (2.0 g, 8.69 mmol) in acetic acid (50 mL) was added urea hydrogen peroxide (4.09 g, 43.5 mmol) at 0° C. After that the reaction mixture was heated to 80° C. and further maintained for 18 h. The reaction was cooled to 0° C. and basified with solid sodium carbonate (till whole acetic acid layer was covered) and diluted with DCM (50 mL). The resulting suspension was then filtered and the filtrate was evaporated. The crude product was triturated with hexane (10 mL) to afford 2.0 g (93%) of the desired product as a white solid. GC-MS (m/z) 245, 247 [M+, Br$^{79,81}$].

Step-2: Ethyl-2,5-dibromonicotinate: To a 0° C. cooled solution of step-1 intermediate (12.0 g, 48.8 mmol) in toluene (150 mL) was added phosphorous oxybromide (13.9 g, 48.8 mmol) drop-wise. The resulting mixture was heated to 65° C. and maintained for 2 h, then cooled to 0° C., poured into crushed ice followed by the addition of ethyl acetate (50 mL). The mixture was basified (pH 8) using aqueous 10% sodium carbonate solution. The layers were separated and the aqueous layer was extracted with ethyl acetate (2×100 mL). The combined organic layers were washed with brine (100 mL), dried (Na$_2$SO$_4$) and filtered. The filtrate was evaporated and the crude product was purified by flash column chromatography (silica gel, EtOAc-Hexane as eluent) to afford 7.0 g (46%) of the desired product as a white solid. $^1$HNMR (400 MHz, CDCl$_3$) δ 8.56 (d, J=2.5 Hz, 1H), δ 8.19 (d, J=2.5 Hz, 1H), 4.44 (q, J=7.0 Hz, 2H), 1.44 (t, J=7.0 Hz, 3H); ESI-MS (m/z) 308, 312 [(MH)+, Br$^{79,81}$].

Step-3: Ethyl-5-bromo-2-(4-(2,6-difluorobenzamido)phenyl)nicotinate: The title compound was prepared by following the general procedure described in Method B using ethyl 2,5-dibromonicotinate (6.40 g, 20.7 mmol) and Intermediate-16 (7.44 g, 20.7 mmol) to afford 4.30 g (45%) of the desired product as a white solid. $^1$HNMR (400 MHz, CDCl$_3$) δ 8.77 (d, J=2.5 Hz, 1H), 8.58 (d, J=2.5 Hz, 1H), 8.02 (s, D$_2$O exchangeable, 1H) 7.69 (d, J=8.5 Hz, 2H), 7.52 (d, J=8.5 Hz, 2H), 7.48-7.41 (m, 1H), 7.02 (t, J=8.0 Hz, 2H), 4.25 (q, J=7.0 Hz, 2H), 1.20 (t, J=7.0 Hz, 3H); ESI-MS (m/z) 461, 463 [(MH)+, Br$^{79,81}$].

Step-4: N-(4-(5-Bromo-3-(4-methyl-5-oxo-4,5-dihydro-1,3,4-oxadiazol-2-yl)pyridin-2-yl)phenyl)-2,6-difluorobenzamide: The title compound was prepared from ethyl-5-bromo-2-(4-(2,6-difluorobenzamido)phenyl)nicotinate by following the similar procedure sequentially as described in step-2, step-3, and step-4 of Intermediate-1a. ESI-MS (m/z) 487, 489 [(MH)+, Br$^{79,81}$].

Step-5: N-(4-(5-Cyclopropyl-3-(4-methyl-5-oxo-4,5-dihydro-1,3,4-oxadiazol-2-yl)pyridin-2-yl)phenyl)-2,6-difluorobenzamide: To a nitrogen gas purged solution of ethyl N-(4-(5-bromo-3-(4-methyl-5-oxo-4,5-dihydro-1,3,4-oxadiazol-2-yl)pyridin-2-yl)phenyl)-2,6-difluorobenzamide (60 mg, 0.12 mmol), in dioxane (4 mL) in a sealed tube was added cyclopropylboronic acid (16 mg, 0.18 mmol) followed by sodium carbonate (34 mg, 0.24 mmol). The resulting mixture was thoroughly deoxygenated by purging nitrogen gas for 15 min and then tetrakis(triphenylphosphine)palladium(0) (14 mg, 0.012 mmol) was added to the above mixture. The reaction was heated to 100° C. and maintained for 18 h. The reaction mixture was then cooled to RT, diluted with EtOAc (5 mL) and filtered through celite. The filtrate was concentrated under reduced pressure. The crude product was purified by flash column chromatography (silica gel, 20% ethyl acetate-hexane system) to afford 15 mg (27%) of the title compound as a white solid. $^1$HNMR (400 MHz, CDCl$_3$) δ 8.61 (d, J=2.5 Hz, 1H), 7.77 (s, D$_2$O exchangeable, 1H) 7.71 (d, J=8.5 Hz, 2H), 7.65 (d, J=2.5 Hz, 1H), 7.51 (d, J=8.0 Hz, 2H), 7.47-7.43 (m, 1H), 7.03 (t, J=8.0 Hz, 2H), 3.45 (s, 3H), 2.03-1.99 (m, 1H), 1.17-1.12 (m, 2H), 0.85-0.82 (m, 2H); ESI-MS (m/z) 449 (MH)$^+$

Example-68

N-(4-(6-Ethyl-5-(4-methyl-5-oxo-4,5-dihydro-1,3,4-oxadiazol-2-yl)pyridin-3-yl)phenyl)-2,6-difluorobenzamide

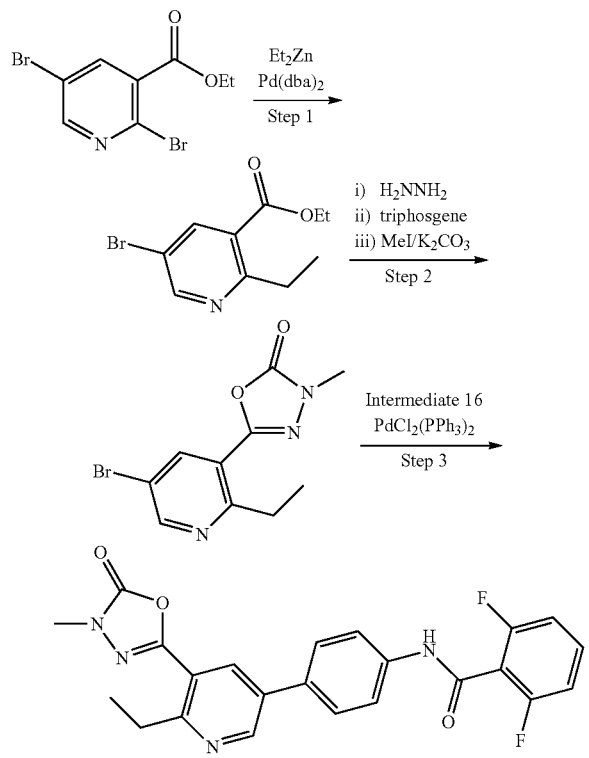

Example 68

Step-1: Ethyl-5-bromo-2-ethylnicotinate: A nitrogen purged and stirred solution of ethyl 2,5-dibromonicotinate (2.5 g, 8.09 mmol) and Pd(dba)$_2$(233 mg, 0.405 mmol) in THF (10 mL), cooled in ice bath (0° C.) was added a solution of diethylzinc (1M in THF 9.71 mL, 9.71 mmol) drop-wise for 15 min. The resulting mixture was warmed to RT and then stirred for 10 min. Reaction mixture was again cooled to 0° C. and then quenched with 0.5 mL cold methanol. Reaction content was diluted with ethyl acetate (20 mL) and filtered through celite. The filtrate was rotary evaporated and the crude product was purified by flash column chromatography (silica gel, 3% EtOAc-hexanes as eluent) to afford 0.5 g (24%) of the title product as a white solid. $^1$HNMR (400 MHz, CDCl$_3$) δ 8.71 (d, J=2.0 Hz, 1H), 8.28 (d, J=2.0 Hz, 1H), 4.41 (q, J=7.0 Hz, 2H), 3.14 (q, J=7.5 Hz, 2H), 1.43 (t, J=7.0 Hz, 3H), 1.26 (t, J=7.5 Hz, 3H); ESI-MS (m/z) 258, 260 [(MH)$^+$ Br$^{79,81}$].

Step-2: 5-(5-Bromo-2-ethylpyridin-3-yl)-3-methyl-1,3,4-oxadiazol-2(3H)-one: The title compound was prepared from ethyl-5-bromo-2-ethylnicotinate by following the procedure sequentially as described in step 2, step-3 and step-4 of Intermediate-1a. $^1$HNMR (400 MHz, DMSO-d$_6$) δ 8.80 (d, J=2.5 Hz, 1H), 8.22 (d, J=2.5 Hz, 1H), 3.44 (s, 3H) 3.05 (q, J=7.5 Hz, 2H), 1.23 (t, J=7.5 Hz, 3H); ESI-MS (m/z) 284, 286 [(MH)$^+$, Br$^{79,81}$]

Step-3: N-(4-(6-Ethyl-5-(4-methyl-5-oxo-4,5-dihydro-1,3,4-oxadiazol-2-yl)pyridin-3-yl)phenyl)-2,6-difluorobenzamide: The title compound was prepared by reacting 5-(5-bromo-2-ethylpyridin-3-yl)-3-methyl-1,3,4-oxadiazol-2 (3H)-one and Intermediate-16 by following the general procedure for coupling reaction as described in Method A. $^1$HNMR (400 MHz, DMSO-d$_6$) δ 10.98 (s, D$_2$O exchangeable, 1H), 9.00 (d, J=2.5 Hz, 1H), 8.26 (d, J=2.5 Hz, 1H), 7.85-7.80 (m, 4H), 7.63-7.59 (m, 1H), 7.28 (t, J=8.0 Hz, 2H), 3.46 (s, 3H), 3.13 (q, J=7.5 Hz, 2H), 1.28 (t, J=7.5 Hz, 3H); ESI-MS (m/z) 437 (MH)$^+$ Biological Assays and Utility:

The CRAC channel modulatory activity of the compounds were thus evaluated by measuring the secretion of IL-2 by antigen stimulated T-cells in vitro. Alternatively, such activity can also be evaluated by assay methods known to one skilled in the art.

In Vitro Assay

Example-69

Inhibition of IL-2 secretion: Jurkat T cells were seeded at a density of 0.5 to 1 million cells per well in RPMI medium. Test compounds from this invention were added to the cells at different concentrations. This was followed by the addition of PHA, a T cell mitogen after 10 minutes. The cells were then incubated for 20 to 24 hours in a CO$_2$ incubator at 37° C. After incubation with the compounds, cells were centrifuged, the supernatant was collected and processed for ELISA to quantitate the amount of IL-2 secreted. A commercial ELISA kit (R&D Systems, Inc. Minneapolis, Minn., USA) was used to estimate the IL-2 concentrations. Amount of IL-2 secreted by cells stimulated with PHA was considered as a 100% maximal signal and the decrease in amount of IL-2 secreted by cells treated with the test compounds was expressed as percent inhibition of the maximal signal. The dose response data was analyzed using 4-parametric sigmoidal dose response (variable slope) curve—fit.

In the above IL-2 assay, compounds of the invention were found to have IC$_{50}$ (nM) values as shown below:

| IC$_{50}$ (nM) | Examples |
| --- | --- |
| <100 nM | 2, 4, 6, 7, 10, 11, 12, 15, 29, 30, 32, 33, 35, 36, 37, 41, 42, 43, 54, 57, 59, 60, 61, |
| 100 nM-1000 nM | 1, 3, 5, 8, 9, 13, 16, 27, 28, 31, 34, 38, 39, 40, 46, 47, 48, 49, 53, 55, 58, 62, 41B, 66, |
| >1000 nM | 14, 17, 18, 19, 20, 21, 22, 23, 24, 25, 26, 44, 45, 50, 51, 56, 63, 41A, 64, 65, 67, 68 |

Thus, compounds of the invention are shown to inhibit IL-2 secretion.

Example-70

SOCE inhibition: Jurkat E6.1 cells were seeded at a density of 1-2×10$^5$ cells per well in calcium-4 dye prepared in calcium free HBSS (Sigma, USA). Test compounds from this invention were added to the cells at different concentrations. This was followed by the addition of thapsigargin (TG), a SERCA inhibitor, to empty the stores of calcium. Calcium chloride was added to the cells after 10-30 min to induce calcium influx and the fluorescence was measured for 10 min using the FLIPR-Tetra detection system. Fluorescence was also measured using a plate reader at 485 nm excitation and 520 nm emission (Synergy2, Biotek, USA) after 30-90 minutes of calcium addition. Fluorescence observed in cells treated with Thapsigargin and calcium chloride solution was considered 100% maximal signal and the reduced fluorescent signal observed in the presence of test compounds was expressed as percent inhibition of the maximal signal. The dose response data was analyzed using 4-parametric sigmoidal dose response (variable slope) curve—fit.

In the above SOCE inhibition assay, compounds of the present invention showed activity less than <1000 nM against SOCE. Thus, compounds of the invention are shown to have CRAC channel modulation activity by inhibition of SOCE.

Example-71

NFAT Transcriptional Activity: HEK 293 cells were stably co-transfected with a NFAT-FireflyLuciferase and Tk-Renilla Luciferase reporter genes 30,000-80,000 cells were seeded per well. Test compounds from this invention were added to the cells at different concentrations. Thapsigargin (TG) was added after 10 mins and the cells were incubated for 4-8 h. The NFAT-Firefly luciferase and Tk-*Renilla* luciferase activity was measured using Dual-Glo reagent (Promega USA). The *Renilla* luciferase activity was used for protein normalization. Luminescence observed in cells treated with thapsigargin was considered 100% maximal signal and the reduced fluorescent signal observed in the presence of test compounds was expressed as percent inhibition of the maximal signal. The data was analyzed using 4-parametric sigmoidal dose response (variable slope) curve-fit.

In the above NFAT transcriptional activity assay, compounds of the present invention showed activity less than <1000 nM. Thus, compounds of the invention are shown to inhibit NFAT transcription activity.

Thus, the in vitro screening assays showed that the compounds of invention inhibit CRAC channel activity.

As mentioned hereinbefore, the CRAC channel is involved with numerous biological responses through various $Ca^{2+}$ signaling pathways. The compounds of the present invention are therefore useful for the treatment and/or prophylaxis of, although not limited to, inflammatory conditions, cancer, rheumatoid arthritis, allergic disorders, immune disorders, cardiovascular diseases, thrombocytopathies and all related conditions which can be benefitted by the CRAC channel modulatory properties of the compounds described herein.

The compounds of the present invention can be administered to a warm-blooded animal, including human being, for the treatment and/or prophylaxis of one or many diseases or disorders mentioned hereinabove which can be benefitted by the CRAC channel modulatory properties of the compounds described herein. The compounds may be Formulated according to the methods known in the art as well as by new methods and may be administered to the body system via gastro-intestinal tract as well as via other routes known to a person skilled in the art. Thus, administration of the compounds of the present invention via oral route, parenteral route, inhalation and/or topical applications are within the scope of this application. Any combination of a compound of the present invention with excipients and/or other therapeutic agents known in the art for the said conditions, diseases and/or disorders are also encompassed by the present invention. All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

We claim:
1. A compound having the Formula (I):

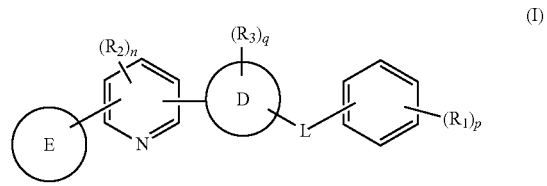

wherein,
ring E is a 5-membered non aromatic heterocyclic ring

X is —NR—;
Y is —C(O)—;
R is substituted or unsubstituted alkyl or haloalkyl;
L is selected from —C(O)NR$_{11}$—, —NR$_{11}$C(O)— and —NR$_{11}$CH$_2$—;
ring D is

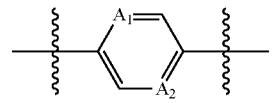

wherein A$_1$ and A$_2$ are CR$_3$;
R$_1$, which may be same or different at each occurrence, is independently selected from halogen, cyano, nitro, hydroxyl, substituted or unsubstituted alkyl, haloalkyl, substituted or unsubstituted alkoxy, haloalkoxy and substituted or unsubstituted cycloalkyl;
R$_2$, which may be same or different at each occurrence, is independently selected from halogen, hydroxyl, cyano, nitro, substituted or unsubstituted alkyl, haloalkyl, substituted or unsubstituted alkenyl, substituted or unsubstituted alkynyl, substituted or unsubstituted alkoxy, haloalkoxy, substituted or unsubstituted cycloalkyl, substituted or unsubstituted cycloalkoxy, —NR$_6$R$_7$ and —NHC(O)R$_9$;
R$_3$, which may be same or different at each occurrence, is independently selected from hydrogen, halogen, substituted or unsubstituted alkyl, substituted or unsubstituted alkoxy, haloalkyl, haloalkoxy, substituted or unsubstituted cycloalkyl, —NR$_6$R$_7$, —C(O)NR$_6$R$_7$ and —C(O)OR$_8$;
R$_6$ and R$_7$, which may be same or different at each occurrence, are independently selected from hydrogen, substituted or unsubstituted alkyl and substituted or unsubstituted cycloalkyl;

$R_8$, which may be same or different at each occurrence, is independently hydrogen, substituted or unsubstituted alkyl;

$R_9$, which may be same or different at each occurrence, is independently selected from substituted or unsubstituted alkyl and substituted or unsubstituted cycloalkyl;

$R_{11}$ is hydrogen;

'n' is an integer ranging from 0 to 2, both inclusive;

'p' is an integer ranging from 0 to 3, both inclusive;

'q' is an integer ranging from 1 to 2, both inclusive; and where the substituents on alkyl, cycloalkyl, alkoxy, cycloalkoxy are independently selected from hydroxy, halogen, carboxyl, cyano, nitro, alkyl, haloalkyl, aryl, cycloalkyl, —C(O)OR$^x$, —C(O)R$^x$, —C(O)NR$^x$R$^y$, —NR$^x$C(O)NR$^y$R$^z$, —NR$^x$R$^y$, —NR$^x$C(O)R$^y$, —S(O)$_2$NR$^x$R$^y$, —OR$^x$, —SR$^x$, and —S(O)$_2$R$^x$; wherein each occurrence of R$^x$, R$^y$ and R$^z$ are independently selected from hydrogen, halogen, alkyl, haloalkyl, and cycloalkyl;

or a pharmaceutically acceptable salt thereof.

2. The compound of claim 1 having the Formula (II)

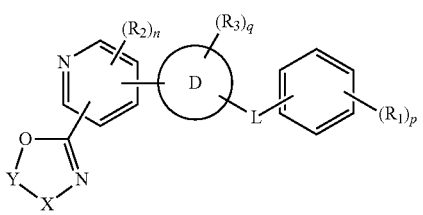

(II)

or a pharmaceutically acceptable salt thereof, wherein, L is selected from —C(O)NH—, —NHC(O)— and —NHCH$_2$—;

ring D, X, Y, $R_1$, $R_2$, $R_3$, 'n', 'p', and 'q' are as defined in claim 1.

3. The compound of claim 1, wherein ring

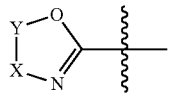

is

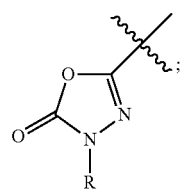

(ii)

wherein R is substituted or unsubstituted alkyl.

4. The compound of claim 1, wherein L is —C(O)NR$_{11}$—, —NR$_{11}$C(O)— or —NR$_{11}$CH$_2$—; wherein R$_{11}$ is hydrogen.

5. The compound of claim 1, wherein $R_1$ is selected from halogen, cyano, nitro, hydroxyl, substituted or unsubstituted alkyl, haloalkyl, substituted or unsubstituted alkoxy, haloalkoxy and substituted or unsubstituted cycloalkyl; and 'p' is 0, 1, 2, or 3.

6. The compound of claim 1, wherein ring D is

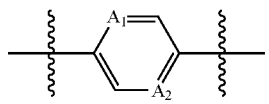

wherein $A_1$ and $A_2$ are CR$_3$; $R_3$ is hydrogen, halogen, substituted or unsubstituted alkyl, haloalkyl and substituted or unsubstituted cycloalkyl; and 'q' is 1 or 2.

7. The compound of claim 1, wherein $R_3$ is hydrogen, halogen, substituted or unsubstituted alkyl, haloalkyl and substituted or unsubstituted cycloalkyl; and 'q' is 1 or 2.

8. The compound of claim 1, wherein $R_2$ is selected from halogen, hydroxyl, cyano, nitro, substituted or unsubstituted alkyl, haloalkyl, substituted or unsubstituted alkoxy, haloalkoxy, substituted or unsubstituted cycloalkyl, and —NR$_6$R$_7$ where R$_6$ and R$_7$ are independently a hydrogen or substituted or unsubstituted alkyl; and 'n' is 0, 1 or 2.

9. The compound of claim 1, having the Formula (IV):

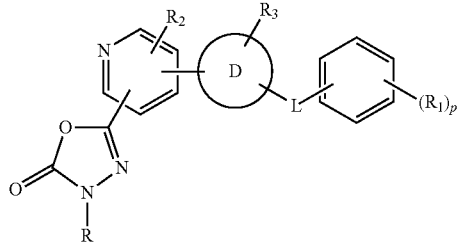

(IV)

wherein R is substituted or unsubstituted alkyl; L is —C(O)NH—, —NHC(O)—, or —NHCH$_2$—; R$_1$ may be same or different and are independently a halogen, substituted or unsubstituted alkyl, haloalkyl or substituted or unsubstituted cycloalkyl; 'p' is 1, 2, or 3; ring D is

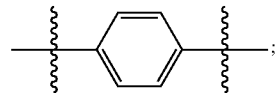

$R_3$ is hydrogen, halogen, substituted or unsubstituted alkyl; $R_2$ is halogen, substituted or unsubstituted alkyl, haloalkyl, substituted or unsubstituted alkoxy, haloalkoxy, substituted or unsubstituted cycloalkyl, and —NR$_6$R$_7$ where R$_6$ and R$_7$ are independently a hydrogen or substituted or unsubstituted alkyl; and 'n' is 0, 1 or 2.

10. A compound which is selected from:

2,6-Difluoro-N-(4-(2-methyl-5-(4-methyl-5-oxo-4,5-dihydro-1,3,4-oxadiazol-2-yl)pyridin-3-yl)phenyl)benzamide;

N-(4-(2-ethyl-5-(4-methyl-5-oxo-4,5-dihydro-1,3,4-oxadiazol-2-yl)pyridin-3-yl) phenyl)-2,6-difluorobenzamide;

N-(2,6-Difluorophenyl)-4-(2-ethyl-5-(4-methyl-5-oxo-4,5-dihydro-1,3,4-oxadiazol-2-yl)pyridin-3-yl)benzamide;

N-(4-(2-Cyclopropyl-5-(4-methyl-5-oxo-4,5-dihydro-1,3,4-oxadiazol-2-yl)pyridin-3-yl)phenyl)-2,6-difluorobenzamide;

4-(2-cyclopropyl-5-(4-methyl-5-oxo-4,5-dihydro-1,3,4-oxadiazol-2-yl)pyridin-3-yl)-N-(2,6-difluorophenyl)benzamide;

2,6-Difluoro-N-(4-(2-methoxy-5-(4-methyl-5-oxo-4,5-dihydro-1,3,4-oxadiazol-2-yl)pyridin-3-yl)phenyl)benzamide;

2,6-difluoro-N-(4-(5-(4-methyl-5-oxo-4,5-dihydro-1,3,4-oxadiazol-2-yl)-2-(trifluoromethyl)pyridin-3-yl)phenyl) benzamide;

2,6-difluoro-N-(3-methyl-4-(5-(4-methyl-5-oxo-4,5-dihydro-1,3,4-oxadiazol-2-yl)-2-(trifluoromethyl)pyridin-3-yl)phenyl) benzamide;

2-Chloro-6-fluoro-N-(4-(5-(4-methyl-5-oxo-4,5-dihydro-1,3,4-oxadiazol-2-yl)-2-(trifluoromethyl)pyridin-3-yl)phenyl)benzamide;

2,6-Difluoro-N-(4-(5-(4-methyl-5-oxo-4,5-dihydro-1,3,4-oxadiazol-2-yl)-2-(methylamino)pyridin-3-yl)phenyl)benzamide;

2-Chloro-6-fluoro-N-(4-(5-(4-methyl-5-oxo-4,5-dihydro-1,3,4-oxadiazol-2-yl)-2-(methylamino)pyridin-3-yl)phenyl)benzamide;

2-Fluoro-6-methyl-N-(4-(5-(4-methyl-5-oxo-4,5-dihydro-1,3,4-oxadiazol-2-yl)-2-(methylamino)pyridin-3-yl)phenyl)benzamide;

2,6-Difluoro-N-(3-methyl-4-(5-(4-methyl-5-oxo-4,5-dihydro-1,3,4-oxadiazol-2-yl)-2-(methylamino)pyridin-3-yl)phenyl)benzamide;

2,6-Difluoro-N-(4-(5-(4-methyl-5-oxo-4,5-dihydro-1,3,4-oxadiazol-2-yl)pyridin-3-yl)phenyl)benzamide;

2,6-Difluoro-N-(3-methyl-4-(5-(4-methyl-5-oxo-4,5-dihydro-1,3,4-oxadiazol-2-yl)pyridin-3-yl)phenyl)benzamide;

N-(4-(4-Ethyl-5-(4-methyl-5-oxo-4,5-dihydro-1,3,4-oxadiazol-2-yl)pyridin-3-yl)phenyl)-2,6-difluorobenzamide;

N-(2,6-Difluorophenyl)-4-(4-ethyl-5-(4-methyl-5-oxo-4,5-dihydro-1,3,4-oxadiazol-2-yl)pyridin-3-yl)benzamide;

N-(4-(3-Ethyl-4-(4-methyl-5-oxo-4,5-dihydro-1,3,4-oxadiazol-2-yl)pyridin-2-yl)phenyl)-2,6-difluorobenzamide;

N-(2,6-Difluorophenyl)-4-(3-ethyl-4-(4-methyl-5-oxo-4,5-dihydro-1,3,4-oxadiazol-2-yl)pyridin-2-yl)benzamide;

2,6-Difluoro-N-(4-(3-methyl-4-(4-methyl-5-oxo-4,5-dihydro-1,3,4-oxadiazol-2-yl)pyridin-2-yl)phenyl)benzamide;

N-(4-(5-Ethyl-4-(4-methyl-5-oxo-4,5-dihydro-1,3,4-oxadiazol-2-yl)pyridin-2-yl)phenyl)-2,6-difluorobenzamide;

N-(2,6-Difluorophenyl)-4-(5-ethyl-4-(4-methyl-5-oxo-4,5-dihydro-1,3,4-oxadiazol-2-yl)pyridin-2-yl)benzamide;

2,6-Difluoro-N-(4-(6-methyl-4-(4-methyl-5-oxo-4,5-dihydro-1,3,4-oxadiazol-2-yl)pyridin-2-yl)phenyl)benzamide;

N-(4-(4-Chloro-6-(4-methyl-5-oxo-4,5-dihydro-1,3,4-oxadiazol-2-yl)pyridin-2-yl)phenyl)-2, 6-difluorobenzamide;

N-(4-(4-Ethoxy-6-(4-methyl-5-oxo-4,5-dihydro-1,3,4-oxadiazol-2-yl)pyridin-2-yl)phenyl)-2,6-difluorobenzamide;

2,6-Difluoro-N-(4-(2-(4-methyl-5-oxo-4,5-dihydro-1,3,4-oxadiazol-2-yl)pyridin-4-yl)phenyl)benzamide;

2,6-Difluoro-N-(4-(4-methyl-6-(4-methyl-5-oxo-4,5-dihydro-1,3,4-oxadiazol-2-yl)pyridin-2-yl)phenyl)benzamide;

N-(4-(2-Ethyl-5-(4-methyl-5-oxo-4,5-dihydro-1,3,4-oxadiazol-2-yl)pyridin-3-yl)-3-methylphenyl)-2,6-difluorobenzamide; N-(4-(2-Cyclopropyl-5-(4-methyl-5-oxo-4,5-dihydro-1,3,4-oxadiazol-2-yl)pyridin-3-yl)-3-methylphenyl)-2,6-difluorobenzamide;

N-(4-(2-Ethyl-5-(4-methyl-5-oxo-4,5-dihydro-1,3,4-oxadiazol-2-yl)pyridin-3-yl)phenyl)-2-fluoro-6-methylbenzamide;

2-Chloro-N-(4-(2-ethyl-5-(4-methyl-5-oxo-4,5-dihydro-1,3,4-oxadiazol-2-yl) pyridin-3-yl)phenyl)-6-fluorobenzamide;

N-(4-(4-Ethyl-6-(4-methyl-5-oxo-4,5-dihydro-1,3,4-oxadiazol-2-yl)pyridin-2-yl)phenyl)-2,6-difluorobenzamide;

N-(4-(3-Ethyl-5-(4-methyl-5-oxo-4,5-dihydro-1,3,4-oxadiazol-2-yl)pyridin-2-yl)phenyl)-2,6-difluorobenzamide;

N-(4-(3-Cyclopropyl-5-(4-methyl-5-oxo-4,5-dihydro-1,3,4-oxadiazol-2-yl) pyridin-2-yl)phenyl)-2,6-difluorobenzamide;

N-(4-(5-Cyclopropyl-3-(4-methyl-5-oxo-4,5-dihydro-1,3,4-oxadiazol-2-yl) pyridin-2-yl)phenyl)-2,6-difluorobenzamide and N-(4-(6-Ethyl-5-(4-methyl-5-oxo-4,5-dihydro-1,3,4-oxadiazol-2-yl)pyridin-3-yl)phenyl)-2,6-difluorobenzamide or pharmaceutically acceptable salt thereof.

11. A pharmaceutical composition comprising one or more compounds of Formula (I) according to claim 1, and one or more pharmaceutically acceptable excipients.

* * * * *